(12) United States Patent
Connelly et al.

(10) Patent No.: US 7,244,232 B2
(45) Date of Patent: Jul. 17, 2007

(54) PROCESS FOR IDENTIFYING CANCEROUS AND/OR METASTATIC CELLS OF A LIVING ORGANISM

(75) Inventors: Patrick R. Connelly, Rochester, NY (US); Thomas H. Foster, Rochester, NY (US); Michael L. Weiner, Webster, NY (US); Andrew W. Custer, Rochester, NY (US)

(73) Assignee: Biomed Solutions, LLC, Pittsford, NY (US)

( * ) Notice: Subject to any disclaimer, the term of this patent is extended or adjusted under 35 U.S.C. 154(b) by 266 days.

(21) Appl. No.: 10/131,361

(22) Filed: Apr. 24, 2002

(65) Prior Publication Data

US 2005/0221270 A1 Oct. 6, 2005

Related U.S. Application Data

(63) Continuation-in-part of application No. 09/918,076, filed on Jul. 30, 2001, now Pat. No. 6,793,642, and a continuation-in-part of application No. 09/918,078, filed on Jul. 30, 2001, now Pat. No. 6,743,190, and a continuation-in-part of application No. 09/852,876, filed on May 10, 2001, now abandoned, and a continuation-in-part of application No. 09/850,250, filed on May 7, 2001, now Pat. No. 6,488,704, and a continuation-in-part of application No. 09/800,823, filed on Mar. 7, 2001, now Pat. No. 6,750,055.

(60) Provisional application No. 60/308,628, filed on Jul. 30, 2001.

(51) Int. Cl.
*A61B 5/1455* (2006.01)

(52) U.S. Cl. ............. 600/309; 600/310; 600/317; 600/322; 600/341; 436/63; 424/9.6

(58) Field of Classification Search ............... 424/9.6; 604/4.01, 6.1, 6.15; 600/309, 310, 317, 322, 600/341; 436/63; 422/44; 606/12; 435/8
See application file for complete search history.

(56) References Cited

U.S. PATENT DOCUMENTS

| | | | |
|---|---|---|---|
| 4,839,292 A | | 6/1989 | Cremonese |
| 4,915,683 A | * | 4/1990 | Sieber .................. 604/5.02 |
| 5,188,633 A | * | 2/1993 | Kratzer et al. ............. 606/12 |
| 5,587,458 A | * | 12/1996 | King et al. ............. 530/387.3 |
| 5,721,135 A | | 2/1998 | Thastrup et al. |
| 5,763,266 A | | 6/1998 | Palsson et al. |
| 5,856,174 A | | 1/1999 | Lipshutz et al. |
| 5,888,807 A | | 3/1999 | Palsson et al. |
| 5,958,762 A | | 9/1999 | Stopini et al. |

(Continued)

OTHER PUBLICATIONS

Kimball, J, "Fluorescence-Activated Cell Sorter," Feb. 2003, accessed Jul. 27, 2004 http://users.rcn.com/jkimball.ma.ultranet/BiologyPages/F/FACS.html.*

*Primary Examiner*—Leon B Lankford, Jr.
*Assistant Examiner*—Allison M. Ford
(74) *Attorney, Agent, or Firm*—Buchanan Ingersoll & Rooney PC

(57) ABSTRACT

A process for identifying and treating cells in a living organism. The cells are labeled, circulated within the organism, detected with an implanted detector, and then either isolated or ablated.

12 Claims, 35 Drawing Sheets

U.S. PATENT DOCUMENTS

| | | |
|---|---|---|
| 5,976,813 A | 11/1999 | Beutel et al. |
| 6,001,585 A | 12/1999 | Gramer |
| 6,046,002 A | 4/2000 | Davis et al. |
| 6,097,485 A * | 8/2000 | Lievan ....................... 356/338 |
| 6,099,803 A | 8/2000 | Ackley et al. |
| 6,122,536 A * | 9/2000 | Sun et al. ................... 600/341 |
| 6,197,575 B1 | 3/2001 | Griffith et al. |
| 6,232,107 B1 * | 5/2001 | Bryan et al. ................. 435/189 |
| 6,251,384 B1 | 6/2001 | Tan et al. |
| 6,416,952 B1 | 7/2002 | Pirrung et al. |
| 6,488,704 B1 * | 12/2002 | Connelly et al. .......... 623/1.15 |
| 6,653,124 B1 | 11/2003 | Freeman |
| 6,743,190 B2 * | 6/2004 | Connelly et al. .......... 604/4.01 |
| 2001/0019715 A1 | 9/2001 | Hanna et al. |

* cited by examiner

| | state three | |
|---|---|---|
| | $\rho_{c1}$ $\theta_{c1}$ $\phi_{c1}$ | |
| | $\rho_{c2}$ $\theta_{c2}$ $\phi_{c2}$ | |
| | $\rho_{c3}$ $\theta_{c3}$ $\phi_{c3}$ | |
| | $\rho_{c4}$ $\theta_{c4}$ $\phi_{c4}$ | |
| | . . . . . . . | |
| | $\rho_{n-1}$ $\theta_{n-1}$ $\phi_{n-1}$ | |
| | $\rho_{n-1}$ $\theta_{n-1}$ $\phi_{n-1}$ | |

| | state two | |
|---|---|---|
| | $\rho_{0b}$ $\theta_{0b}$ $\phi_{0b}$ | |
| | $\rho_{1b}$ $\theta_{1b}$ $\phi_{1b}$ | |
| | $\rho_{2b}$ $\theta_{2b}$ $\phi_{2b}$ | |
| | $\rho_{3b}$ $\theta_{3b}$ $\phi_{3b}$ | |
| | . . . . . . . | |
| | $\rho_n$ $\theta_n$ $\phi_n$ | |
| | $\rho_{n-1}$ $\theta_{n-1}$ $\phi_{n-1}$ | |

| | state one | |
|---|---|---|
| $t_0$ | $\rho_0$ $\theta_0$ $\phi_0$ | |
| $t_1$ | $\rho_1$ $\theta_1$ $\phi_1$ | |
| $t_2$ | $\rho_2$ $\theta_2$ $\phi_2$ | |
| $t_3$ | $\rho_3$ $\theta_3$ $\phi_3$ | |
| $t_4$ | $\rho_4$ $\theta_4$ $\phi_4$ | |
| . . . | . . . . . . . | |
| $t_{n-1}$ | $\rho_{n-1}$ $\theta_{n-1}$ $\phi_{n-1}$ | |
| | $\rho_{n-1}$ $\theta_{n-1}$ $\phi_{n-1}$ | |

Figure 33

PROCESS FOR IDENTIFYING CANCEROUS AND/OR METASTATIC CELLS OF A LIVING ORGANISM

CROSS-REFERENCE TO RELATED PATENT APPLICATIONS

This application is a continuation-in-part of applicants' patent applications U.S. Ser. No. 09/800,823 (filed on Mar. 7, 2001) now U.S. Pat. No. 6,750,055, U.S. Ser. No. 09/850,250 (filed on May 7, 2001) now U.S. Pat. No. 6,488,704, U.S. Ser. No. 09/852,876 (filed on May 10, 2001) now abandoned, and U.S. Ser. Nos. 09/918,076 now U.S. Pat. No. 6,793,642 and 09/918,078 now U.S. Pat. No. 6,743,190, both of which were filed on Jul. 30, 2001.

This application is also based, in part, upon provisional patent application 60/308,628, filed on Jul. 30, 2001.

FIELD OF THE INVENTION

A process and a device for the detection and treatment of biological material within an organism.

BACKGROUND OF THE INVENTION

Cancer is the leading cause of death in modern societies. Billions of dollars are spent upon clinical diagnosis and treatment of this disease. In addition to these expenditures, a substantial amount of money is spent on the quest for a cancer cure.

Treatment for a variety of cancers often is more debilitating than the disease itself.

One attempt to address this problem is described in U.S. Pat. No. 6,251,384, which describes a method for following the progression of metastasis of a primary tumor in which organ tissues are removed from a vertebrate subject that has been modified to contain tumor cells that express GFP; the excised tissues are observed for the presence of fluorescence. The problem with the method of this patent is that, every time an analysis is desired of a living organism, surgery must be performed.

In published United States patent application 20010019715A1, a process is described in which a combination of a cytotoxic T-lymphocyte inducing composition and an agent which is capable of neutralizing or down regulating the activity of tumor secreted immunosuppressive factors is administered. The process of this application does not involve detection of malignant cells within a living organism and their subsequent treatment therein.

It is an object of this invention to provide a process for identifying, labeling, isolating, and treating diseased cells within an organism, such as cancer cells.

SUMMARY OF THE INVENTION

In accordance with this invention, there is provided a process for identifying and treating diseased cells. In the first step of this process, cells within a living organism are labeled with a fluorescent marker in an implanted reservoir. Thereafter, the labeled cells are allowed to circulate within the organism and thereafter are detected with the use of an implanted detector and either isolated or ablated.

BRIEF DESCRIPTION OF THE DRAWINGS

The invention will be described by reference to the following drawings, in which like numerals refer to like elements, and in which:

FIGS. 26 through 33 schematically illustrate a preferred process for estimating the position of one or more cells within a flowing bodily fluid.

DESCRIPTION OF THE PREFERRED EMBODIMENTS

Figure 1:
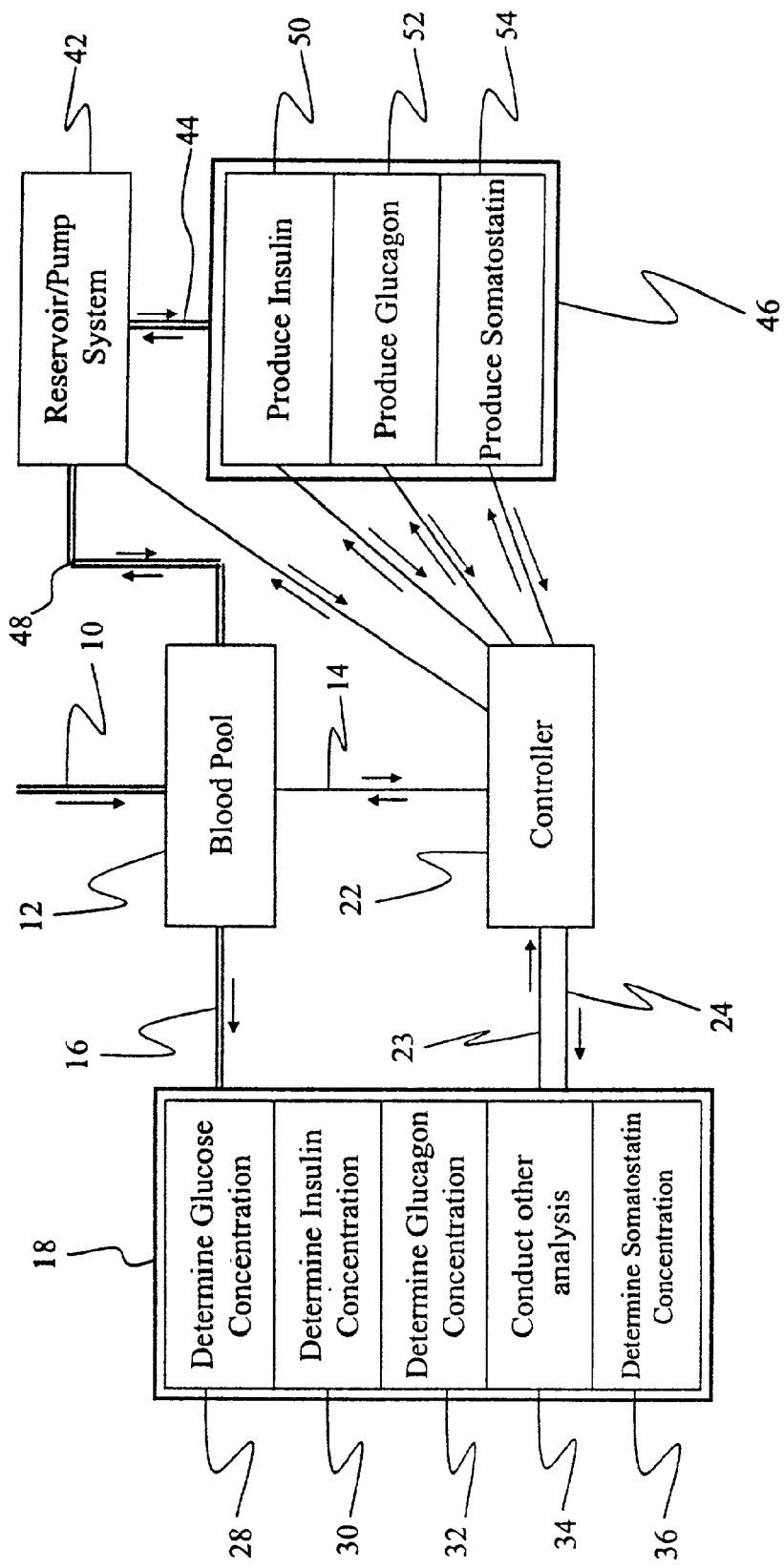
FIG. 1 is a schematic representation of one preferred embodiment of the process of the invention.

FIG. 1 is a flow diagram of one preferred process of the present invention. In the first step of the process depicted, the blood of a living organism is fed via fluid conduit 10 to blood pool 12.

In one embodiment, the living organism is a human being. In this embodiment, the blood may be supplied to the blood pool 12 by any one of several means. As is known to those skilled in the art, and as used in this specification, the term blood pool refers to a reservoir for blood.

Thus, e.g., one may withdraw blood from a human body by means of a hypodermic needle; in this case, the process of the invention may be practiced outside the living organism, except to the extent that blood is returned to the organism. Thus, e.g., one may implant a device, such as the device depicted in FIG. 2, within the living organism and collect blood from such organism within an in vivo reservoir (e.g., see blood pool 12 of FIG. 2); in this case, the process of the invention may be practiced entirely in the body. Thus, e.g., one may sample blood by one or more of the procedures and devices described in U.S. Pat. No. 6,159,164 (blood supply system), U.S. Pat. Nos. 5,902,253, 5,759,160 (hybrid portal), U.S. Pat. Nos. 5,387,192, 4,871,351 (implantable medication infusing system), U.S. Pat. No. 4,832,034, and the like; the entire disclosure of each of these United States patents is hereby incorporated by reference into this specification.

Referring again to FIG. 1, a portion of the blood in the blood pool 12 is fed via fluid conduit 16 to analyzer 18. In analyzer 18, one or more blood parameters may be analyzed in response to a signal from controller 22 fed via communication line 24 (which may be an optical communications line, and/or a radio frequency communications line) with analyzer 18. The information obtained by such analyses is returned to the controller 22 via communication line 23; and the controller, in response to such information, may activate an artificial organ function (see, e.g., culture assembly 46 of FIG. 1) and/or may take or cause to be taken one or more other actions.

In one embodiment, illustrated in FIG. 1, the controller 22 causes the analyzer 18 to determine the concentration of glucose within the blood sample; this is preferably done in operation 28. The analysis of the glucose concentration in the blood may be conducted by conventional means such as, e.g., by a glucose sensor assembly. By way of illustration and not limitation, one may use the processes and devices described in U.S. Pat. No. 5,660,163 (implantable glucose monitoring system comprised of a glucose sensor inserted into a patient's venous system), U.S. Pat. No. 5,448,992 (non-invasive phase sensitive measurement of blood glucose concentration), U.S. Pat. No. 5,995,860 (implantable device for sensing in vivo the level of a blood constituent), U.S. Pat. No. 6,175,752 (in vivo monitoring of glucose), U.S. Pat. No. 6,162,611 (subcutaneous glucose electrode), U.S. Pat. No. 6,143,164 (in vitro glucose sensor), and the like. The entire disclosure of each of these United States patents is hereby incorporated by reference into this specification.

In operation 30 of the process depicted in FIG. 1, the insulin concentration of the blood sample is determined. In operation 32 of the process, the glucagon concentration of the blood sample is determined. The determinations may be made in accordance with prior art procedures and devices. Thus, e.g., one may use one or more of the procedures and devices described, e.g., in U.S. Pat. Nos. 4,792,597, 5,070, 025, 6,180,336, 6,002,000 (chemiluminescent compound and method of use), U.S. Pat. No. 59,365,070, and the like. The disclosure of each of these United States patents is hereby incorporated by reference into this specification.

Referring again to FIG. 1, other analysis or analyses may optionally be conducted in operation 34 of the process. Thus, by way of illustration and not limitation, one can analyze the expression of certain blood factors which are known or believed to cause disease. In operation 36 of the process, which is optional, the concentration of somatostatin is determined. As is known to those skilled in the art, somatostatin inhibits the secretion of both insulin and glucagon, as well as growth hormone and thyroid-stimulating hormone. See, e.g., page 765 of John B. West's "Best and Taylor's Physiological Basis of Medical Practice," Twelfth Edition (Williams and Wilkins, Baltimore, Md., 1991). Reference may also be had to U.S. Pat. Nos. 6,011,008, 5,531,925, 5,491,131, 5,260,275, and the like. The disclosure of West and of each of these United States patents is hereby incorporated by reference into this specification.

As will be apparent to those skilled in the art, for proper homeostatic regulation of glucose and insulin within a living organism, glucose, insulin, glucagon, and somatostatin all must be present in specified concentrations and ratios. The process of one embodiment of this invention allows one to produce the conditions necessary for ideal homeostatic regulation of such analytes.

The information produced in analyzer 18 is fed to controller 22 via communication line 23, which produces a computer-readable profile representing the identity and relative abundance of the glucose, insulin, glucagon, and somatostatin in the blood. The controller is preferably equipped with an algorithm with which it can determine the ideal concentration of each such analyte and can thereafter cause additional insulin and/or glucagon and/or somatostatin and/ or other analyte to be added to the blood pool 12.

Controllers for analyzing and regulating the composition of a biological fluid are known. Thus, e.g., in U.S. Pat. No. 6,064,754, computer-assisted methods and devices for identifying, selecting, and characterizing biomolecules in a biological sample are disclosed. Thus, for example, one may use one or more of the processes or devices described in U.S. Pat. Nos. 6,185,455, 6,122,536 (implantable sensor for measurement and control of blood constituent levels), U.S. Pat. Nos. 5,995,960, 5,978,713, 5,971,931, 5,967,986, and the like. The disclosure of each of these United States patents is hereby incorporated by reference into this specification.

In one embodiment, the controller contains a processing system utilizing an application specific integrated circuit ("ASIC"). These ASIC controllers are well known and are described, e.g., in U.S. Pat. Nos. 5,937,202, 6,041,257, 6,165,155, and the like. The entire disclosure of each of these United States patents is hereby incorporated by reference into this specification.

In one embodiment, the controller comprises a processor complex for processing data from at least one input, comprising at least a first and second processor, each having a data input and a data output, a data input of the second processor receiving data from the data output of the first processor; each processor being programmed with a respective algorithm for processing data received from a respective data input; said first processor being configured to receive raw data and process the raw data according to the respective algorithm programmed therein, and configured to receive other raw data and pass said other raw data to said second processor; and said second processor being configured to receive said other raw data passed from said first processor and process the other raw data according to the algorithm programmed in said second processor, and said second processor is configured to receive processed data from said first processor and pass the processed data from the data input to the data output of said second processor.

Based upon the analyses of the analytes found in the blood sample, the controller 22 will cause either insulin and/or glucagon and/or somatostatin to be withdrawn from blood pool 12 via reservoir/pump system 42 and fed via fluid conduit 44 to cell culture assembly 46. Alternatively, or additionally, reservoir/pump system 42 can pump insulin-containing material and/or glucagon-containing material and/or somatostatin-containing material via fluid conduit 48 and send it to blood pool 12. The reservoir/pump system is equipped with various filtration and separation devices so that it is capable of separating the insulin and/or glucagon and/or somatostatin from blood with which it may be admixed and returning the blood so separated to blood pool 12.

One may use any of the implantable pumps and/or fluid delivery devices known to those skilled in the art. Thus, by way of illustration and not limitation, one may use the implantable medical delivery system described in an article by Li Cao et al. entitled "Design and simulation of an implantable medical drug delivery system using microelectromechanical systems technology," (Sensors and Actuators A 94[2001], pages 117–125). Thus, e.g., one may use the microvalves described in an article by Po Ki Yuen et al. entitled "Semi-disposable microvalves for use with microfabricated devices or microchips," (J. Micromech. Microeng. 10[2000], pages 401–409). Thus, e.g., one may use one or more of the micropumps disclosed in an article by Shulin Zeng et al. entitled "Fabrication and characterization of electoosmotic micropumps" (Sensors and Actuators B 79 [2001], pages 107–114).

In one embodiment, the implantable fluid delivery device of U.S. Pat. No. 6,149,870 ("Apparatus for in situ concentration and/or dilution of materials in microfluidic systems") is used. This patent claims "A microfluidic system for diluting a material in a microfluidic device, the system comprising: a microfluidic device having at least a first main channel disposed therein, said main channel having at least one microscale cross-sectional dimension; at least a first source of said material in fluid communication with said main channel at a first point along a length of said main channel; at least a first diluent source in fluid communication with said main channel at a second point along said length of said main channel; at least a first reservoir in fluid communication with said main channel at a third point along said length of said main channel; and a fluid direction system for delivering diluent and material to said main channel, and combining said diluent with said material to form first diluted material, and for transporting a portion of said first diluted material along said main channel." The entire disclosure of this United States patent is hereby incorporated by reference into this specification.

By way of further illustration, one may use the fluid-delivery device described in U.S. Pat. No. 6,123,861, the entire disclosure of which is hereby incorporated by reference into this specification.

Referring again to FIG. 1, and in another embodiment, the reservoir/pump system 42 is comprised of an insulin pump. Such insulin pumps are well known to those skilled in the art and are described, e.g., in U.S. Pat. Nos. 6,181,957, 6,168, 575, 6,165,155, 6,162,611, 6,135,978, 6,124,134, 6,123,668, and the like. The entire disclosure of each of these United States patents is hereby incorporated by reference into this specification.

In yet another embodiment, the reservoir/pump system is comprised of a pump for pumping or withdrawing analytes such as insulin, glucagon, and somatostatin. The reservoir/pump system can be used for storing and pumping any analyte(s), proteins, cells, polynucleotides, viruses, capsids and the like. One may use for this purpose conventional implantable drug delivery devices. Thus, by way of illustration and not limitation, one may use the devices disclosed in U.S. Pat. No. 5,836,985 (a refillable, rate-controlled drug delivery device with a hollow reservoir), U.S. Pat. No. 5,607,418 (implantable drug delivery apparatus), and the like; the entire disclosure of each of these United States patents is hereby incorporated by reference into this specification. Regardless of the device used, the analyte is added to or withdrawn from the blood pool as dictated by the analyses performed by the controller 22.

Artificial organ 46 preferably includes a reservoir (not shown in FIG. 1) which, in operation 50 of the process, results in the production and accumulation of insulin preferably via a cell/tissue culture. As is known to those skilled in the art, one can grow Islet of Langerhans cells with genetically manipulated beta, alpha, delta and acinar cells of the pancreas in vitro. These form a pseudo organ that can produce insulin. Different environmental conditions can be applied to culture these samples, which will differentiate into functional in vitro pancreata. Reference may be had to U.S. Pat. No. 6,110,743 (the creation of genetically engineered cells and their use in transplant therapy). The entire disclosure of this United States patent is hereby incorporated by reference into this specification.

Reference may also be had to U.S. Pat. No. R.E. 036,844, for a "Cellular attachment to trans-epithelial appliances." This patent describes a method of forming three-dimensional epithelial cellular structures with components normally derived in developing organs, and the use of 804G cells [rat bladder carcinoma cells] for the production of hemi-desmosome components that are responsible for attachment of epithelial cells to the basement membrane). In a preferred embodiment of the patent, an implantable device that is a biocompatible object (i.e., stainless steel mesh) which can be molded to any shape. The material is coated with the soluble factor from 804G cells responsible for producing ectopic hemi-desmosome formation through the attachment of any number of cells. Epithelial cell interaction with the basement membrane is a strict requirement for proper functionality of a variety of epithelial and mesenchymal cell types.

Referring again to FIG. 1, and in the preferred embodiment depicted therein, glucagon is produced by a cell culture in a reservoir (not shown) in operation 52; and somatostatin is produced by a cell culture in a reservoir (not shown) in operation 54. One may produce glucagon in a cell culture, and/or another hormone in a cell culture (somatostatin) by a process which comprises culturing pancreatic cells from a mammalian species in a basal nutrient medium supplemented with normal serum at below about 0.5% and glucose at below about 1 millimolar, allowing said insulin producing stem cells to grow for at least about 3 weeks, and initiating cellular differentiation into mature islet cells by re-feeding the insulin producing stem cells in culture with a nutrient medium supplemented with normal serum at about 0.5–10% and glucose at about 2.5 to about 10 millimolar; see, e.g., U.S. Pat. No. 6,001,647, the entire disclosure of which is hereby incorporated by reference into this specification.

One Preferred Artificial Organ of this Invention

Figure 2:
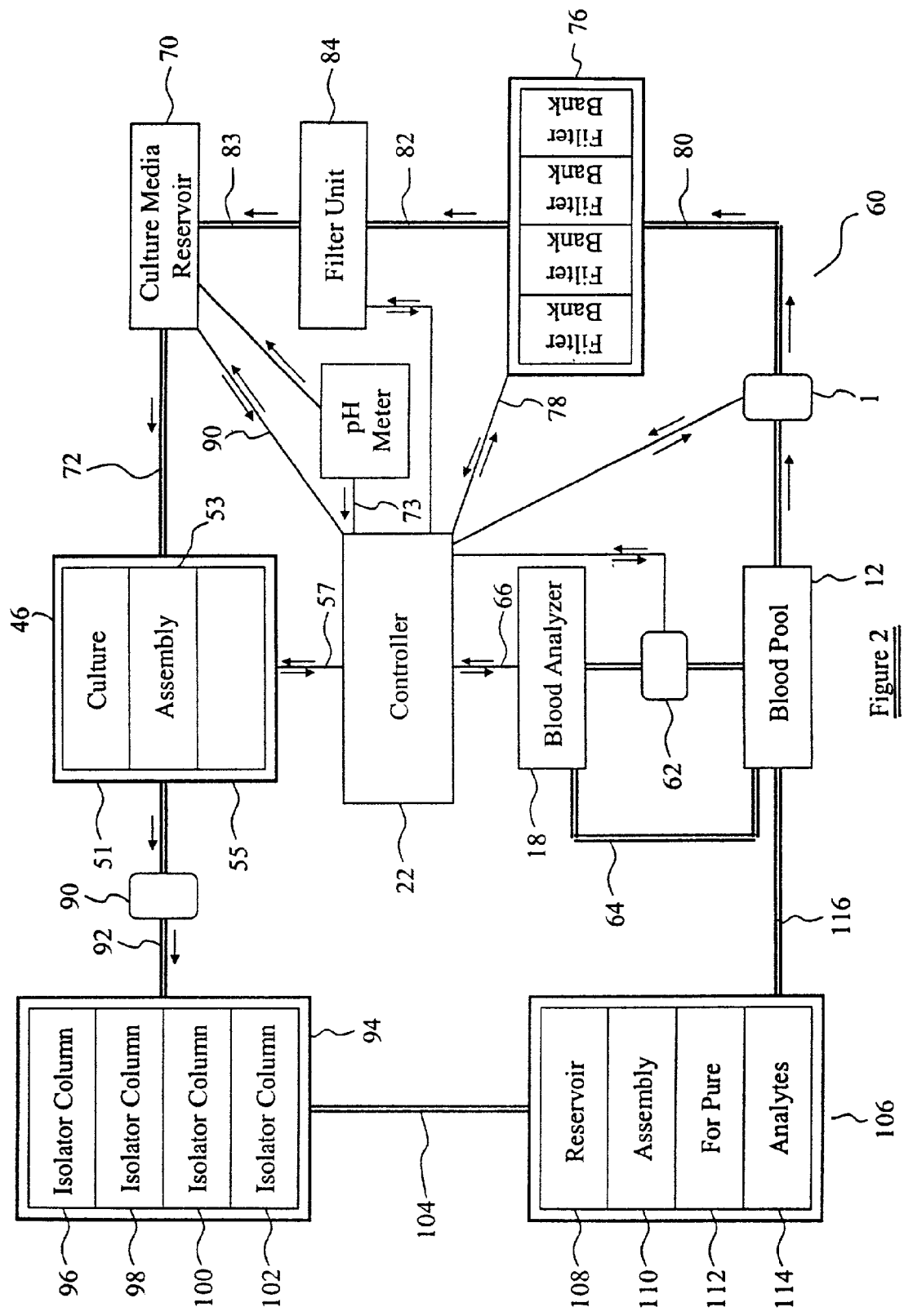
FIG. 2 is a schematic representation of one preferred assembly of this invention.

FIG. 2 is a schematic diagram of one preferred artificial organ 60 which, preferably, is implantable within a living organism (not shown). Referring to FIG. 2, a source of venous blood is supplied from blood pool 12 to the organ 60. The blood may be supplied from a source external to the body, such as via a blood transfusion. In one preferred embodiment, the blood is supplied by a living human body.

Means for withdrawing or segregating or channeling blood from a living organism are well known and are described in, e.g., U.S. Pat. No. 5,902,336 (an implantable device and method for removing fluids from the blood of a patient). This patent discloses a method for the surgical implantation of a filtering device using filters of specified pore size and with the passage of specified flow rates.

By way of further illustration, U.S. Pat. No. 6,123,861 discloses the fabrication of miniaturized drug delivery systems using similar fabrication processes as those used in integrated circuit (IC) production. The devices disclosed in this patent may be used in conjunction with a source of venous blood to supply analytes (such as drugs, hormones, blood constituents, mixtures thereof, etc.) to a system.

A major hurdle in the development of artificial organ systems or in transplant therapy regimes is in the host immune response. Attempts have been made to implant in vitro organ cultures in various anatomical regions of the body in an attempt to replace loss of physiologic function.

By way of further illustration, U.S. Pat. No. 6,001,647 discloses in vitro culture systems, which are manipulated (with, e.g., recombinant genetic techniques) to produce functional Islets of Langerhans. The implantable in vitro systems discussed in this U.S. Pat. No. 6,001,647, and the entire disclosure of this patent, are hereby incorporated by reference into this specification. The in vitro culture system of this patent may be used as the precursor for the implantable in vitro capsule described herein. This is only one example of organ type which can be utilized for the present invention. Additional organ and cellular structures may require much different culture conditions.

Referring again to FIG. 2, and in the preferred embodiment depicted therein, blood is withdrawn via a catheter (not shown) from venous blood supply 12 to blood analyzer 18 via pump 62. After such blood is analyzed, it is returned to blood pool 12 via line 64. In one embodiment, this process is continuous.

The information obtained from the blood analyses is fed via communications line 66 to ASIC controller 22. In one embodiment, in addition to analyzing the hormone levels in the venous blood supply 12, and controlling the amount of analyte released from culture assembly 46 (see also FIG. 1), the controller 22 preferably controls the type and concentrations of constituents fed into the cell culture system of culture assembly 46 which are necessary for the in vitro production of the desired analytes. These constituents/reagents are fed to a culture media reservoir 70 which, in response to signals from controller 22, feeds some or all of these reagents via fluid conduit 72 to culture assembly 46 in response to signals from controller 22, which is in communication with culture assembly 46 via communication line 74.

The constituents/reagents, which are fed from culture media reservoir 70 are preferably initially collected in culture media collector 76. The controller 22 furnishes information to collector 76 via communication line 78 as to the type and concentration of the various analytes which are required for the maintenance of the in vitro culture assembly 46. These analytes are initially fed to collector 76 via fluid conduit 80 and, thereafter, it is passed via fluid conduit 82 to filter 84, in which the analytes are sterilized and purified. Then the purified constituents are fed via fluid conduit 83 to reservoir 70.

The filter 84 preferably removes bacteria, pathogens, and other agents which are not conducive for the desired in vitro cell culture processes.

In one embodiment, the pH of the material in the cell culture media reservoir 70 is monitored to insure that it is preferably is between 7.1 to 7.4 by means of pH meter 71; pH meter 71 is operatively connected to the controller 22 by means of communication line 73. If the pH measured in reservoir 70 is lower than pH 7.1, controller 22 will signal culture media collector 76 to extract carbonic anhydride (carbonic acid minus a hydrogen ion) from venous blood supply 12 to feed it to filter 84 and thence to culture media reservoir 70, where its presence will increase the pH. Conversely, if the pH in reservoir 70 is higher than the desired range, carbonic anhydride may be withdrawn from the reservoir 70.

In a similar manner, not shown, the pH within the culture assembly 46, and within each of the operating components 51, 53, and 55 thereof, may also be adjusted by the addition or removal of the carbonic anhydride, in response to signals from the controller 22 (see line 57). In the embodiment depicted, cell culture operation 51 produces insulin, cell culture operation 53 produces glucagon, and cell culture operation 55 produces somatostatin.

Referring again to FIG. 2, and in the preferred embodiment depicted therein, the carbonic anhydride is fed via fluid conduit 72 to culture assembly 46 and/or any component thereof, such as cell culture operation 51, 53, and/or 55.

In one embodiment, there are several information streams communicated to the controller 22, including streams of information about the pH in both reservoir 70 and the culture assembly 46. The controller 22 evaluates all of these factors (using microprocessor algorithms) and then determines the precise combination of reagents needed to be delivered via fluid conduits 80, 82, and 72 to obtain the desired pH range (and analytes) in both culture reservoir 70 and cell culture assembly 46. In addition to the carbonic anhydride, the controller 22 may cause the delivery of other pH-modifying analytes to adjust the pH. Thus, e.g., one may use a salt, which is basic when it hydrolyzes such as, e.g., calcium carbonate.

Referring again to FIG. 2, the analytes required by the body to maintain the desired homeostatic condition(s) are withdrawn, as needed, from culture assembly 46 by a pump 90 and fed via fluid conduit 92 to isolator assembly 94.

Isolator assembly 94 is comprised of a multiplicity of isolation filter columns 96, 98, 100 and 102, which, by appropriate purification and elution techniques, isolate one or more purified for each of columns 96, 98, 100, and 102 et seq. The purified analytes are then delivered, as needed, via fluid conduit 104 to reservoir assembly 106, in which one or more of the purified analytes may be separately stored in reservoir chambers 108, 110, 112, 114 et seq. Based upon the directions received from controller 22, these purified analytes may be delivered into venous blood supply 12 via fluid conduit 116.

In one embodiment, the analyte(s) in each of reservoir chambers 108, 110, 112, and 114 are diluted in a separate dilution chamber (not shown) disposed within each such reservoir. It is preferred that the analyte(s) be diluted with blood plasma, which contains neither red blood cells nor white blood cells.

Figure 3:
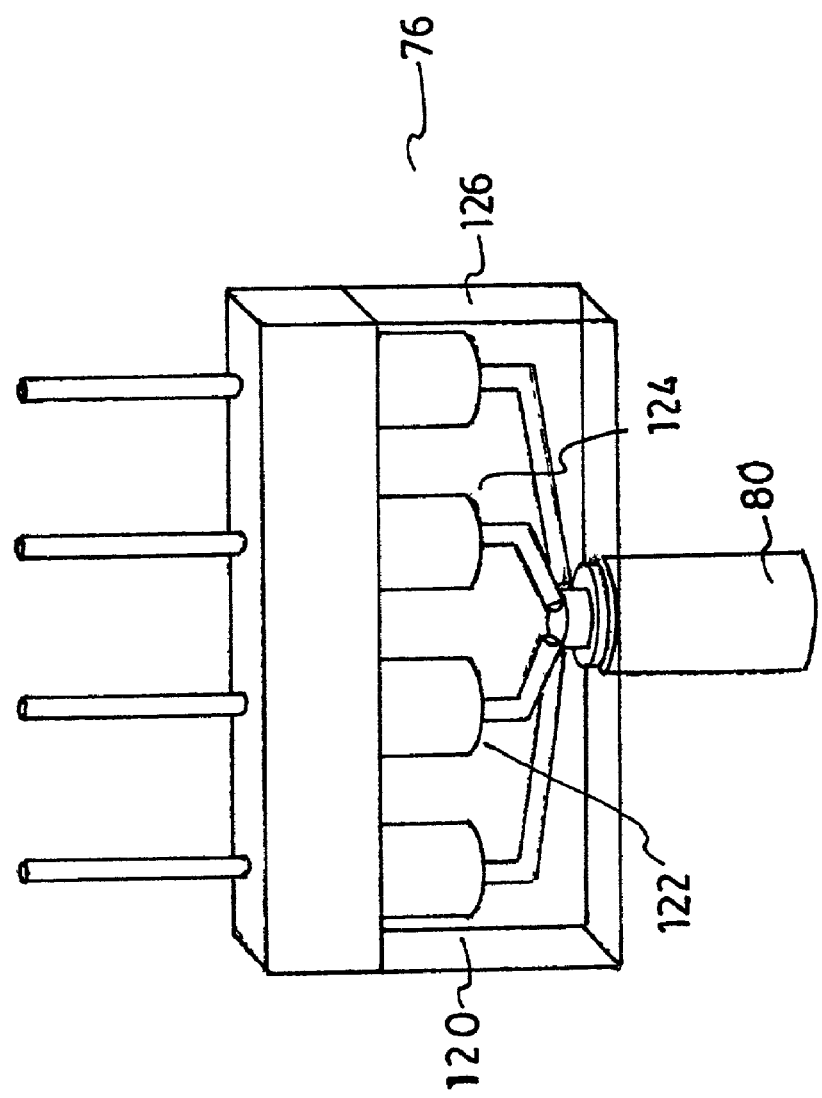
FIG. 3 is a schematic representation of another preferred assembly of one component of this invention.

FIG. 3 is schematic view of a preferred embodiment of culture media collector 76. Referring to FIG. 3, it will be seen that collector 76 is comprised of input port 80, which communicates with filter banks 120, 122, 124, and 126. Although only four such filter banks, and associated lines, are illustrated in FIG. 3, it will be apparent that many more (or fewer) filter banks can be used, depending upon the number of analytes involved.

In one embodiment, the filter banks 120 et seq. are immunoisolation chambers or columns. In another embodiment, one or more of the purification techniques disclosed in Terry M. Phillips et al.'s "Affinity and Immunoaffinity" (Eaton Publishing, 2000) may be used.

The purified outputs from banks 120 et seq. are then fed to filter 84 and thence to culture media reservoir 70 (see FIG. 2).

The device 76, in addition to being used as culture media collector 76, may also be used as the isolator bank 91 and/or as a component of the blood analyzer 18 (see FIG. 2).

The processes and devices disclosed in this specification may be used with a multiplicity of different organ systems. Thus, by way of illustration, it may be used as an implantable dialysis device in the manner discussed in U.S. Pat. No. 5,902,336. Thus, e.g., it may be used as an implantable liver, an implantable bladder (see U.S. Pat. No. 4,961,747), an implantable thymus, an implantable adrenal medulla, and like. By way of further illustration, the devices and processes of this application may be used for the enhancement of T-cell production in immune disorders, for the enhancement of Hepatic function for various liver, disorders, for the enhancement of renal function for various kidney disorders, for the enhancement of digestive function in any number of digestive system disorders, for the enhancement of reproductive function in any number of reproductive system disorders, for the enhancement of cardiac function in any number of cardiac disorders, etc.

In one embodiment, the artificial organ of this invention is hermetically sealed entirely to prevent corrosion. It preferred to seal the artificial organ with a biocompatible coating.

In an additional embodiment, the enclosed invention may also be used for the early stage detection of tumorigenic and/or metastatic conditions.

In yet another embodiment of this invention the detection of the reduction in specific enzymes required for an efficient and homeostatic physiological condition. Enzymes, which are responsible for and/or a product of any and all combinations of efficient physiological function.

Referring again to FIG. 1, one preferred analyzer 18 may be the particle analyzer described in the patent pending U.S. Ser. No. 09/850,250. Flow cytometry (FC) is used to detect variations in cell types and/or particles by use of fluorescent labeling and endogenous cellular optical properties. Originally flow cytometric systems were used solely to rapidly count cells. The cells were traditionally isolated from tissue or blood and labeled with fluorescent markers or antibodies conjugated with fluorescent tags. A variety of cell types have been analyzed using these methods. Cell volume and type could also be characterized by the intensity and angular component of scattered light. Following isolation, cells were then fed through a flow chamber of specified dimensions.

Optical FC systems are based on either the detection of intrinsic scattering properties of cells (which include the cellular membrane structure, organelle concentration and structure, cytoplasmic structure, and DNA/chromatin structure) and/or of detection of emitted light from fluorescently labeled cells. The cells are usually labeled with fluorescent conjugated antibodies to cell surface receptors or cytoplasmic proteins. A source for the emission of a specified frequency of energy (i.e., a light source) is directed toward the stream of flowing cells through a narrow flow cell. It is possible to detect with a photomultiplier tube array the scattering of light through the cell ("forward light scattering"), the scattered light which is reflected orthogonal to the direction of the flow ("side light scattering"), and the fluorescence emission from fluorescently conjugated antibodies to a variety of factors within and on the cell surface.

In the process of the present invention, a particle analyzer is provided that is also capable of being used as a stent. As is known to those skilled in the art, and as is disclosed in U.S. Pat. No. 6,190,393 (the entire disclosure of which is hereby incorporated herein by reference), a stent is a flexible cylinder or scaffold made of metal or polymer; and it may be permanently implanted into a blood vessel following an angioplasty procedure. The stent tends to hold the lumen open longer, to reinforce the vessel wall, and to improve blood flow.

To improve efficiency and reduce time required for the vascular procedure, it is desirable to combine these angioplasty and stent deployments. This combined procedure may be referred to as "primary stenting" or "direct stenting."

During a primary stenting procedure, an initial angioplasty is not performed. Rather, a modified stent delivery system is used to cross or traverse a lesion or stenosis, to expand the desired site in a fashion similar to angioplasty and deploy a stent. In this direct stenting procedure, the stent delivery system is first advanced within the patient's body until the stent is located within the desired site where the lesion or stenosis is present.

The particle analyzer of this invention may be inserted into a living organism in the same manner as is commonly done with primary stenting. One preferred embodiment of such particle analyzer is illustrated in FIG. 4.

Figure 4:
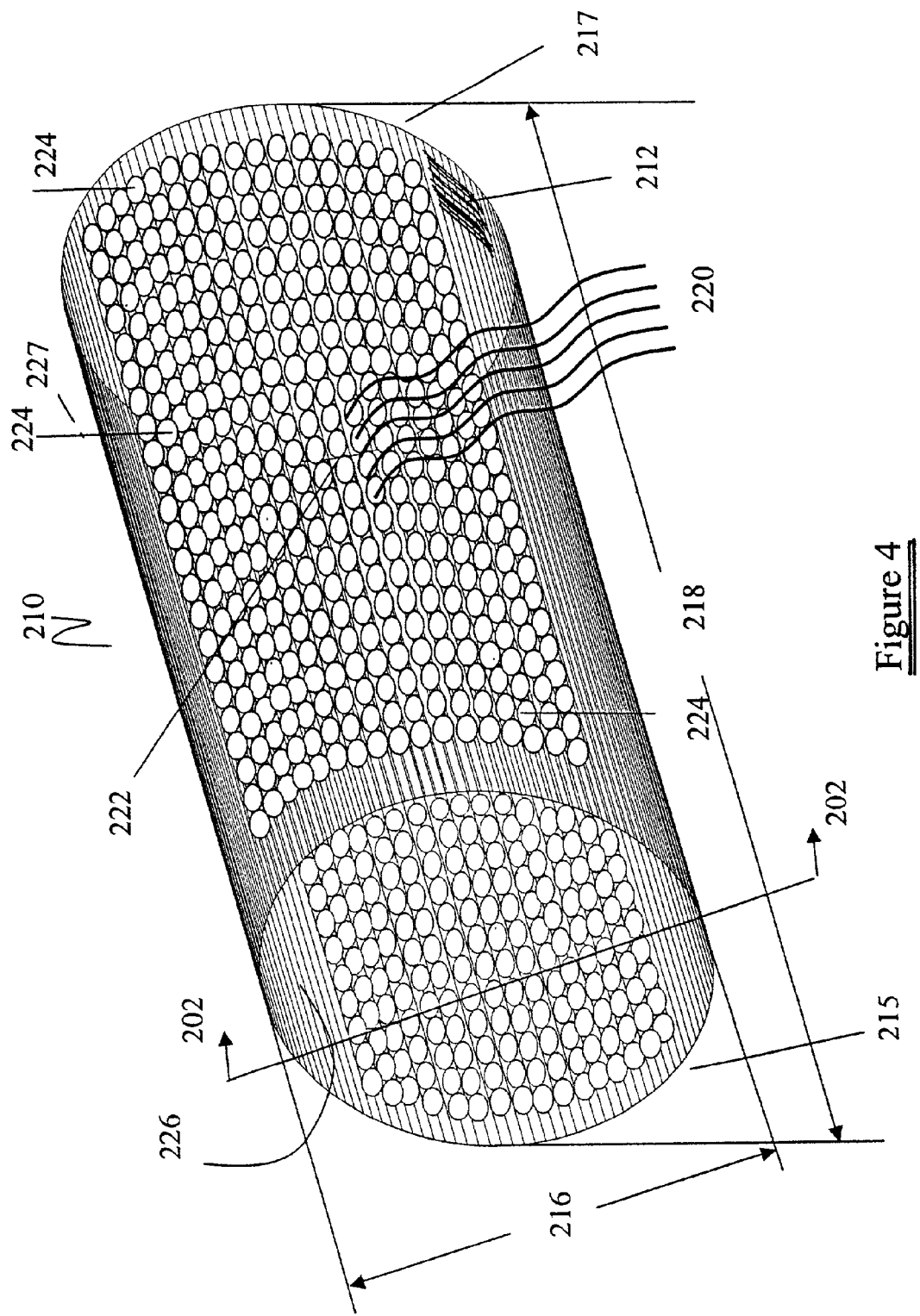
FIG. 4 is a perspective view of one preferred particle analyzer sub-assembly of the entire assembly of FIG. 1.

FIG. 4 is a perspective view of one preferred particle analyzer 210 of this invention. Referring to FIG. 4, it will be seen that particle analyzer 210 is comprised of a casing (not shown in FIG. 4) and an interior surface 226.

In the preferred embodiment depicted in FIG. 4, particle analyzer 210 has an external diameter 216 of from 100 micrometers to about 3 millimeters and, preferably, from about 250 to about 700 microns. Additionally, particle analyzer 210 has a length 218 of from about 500 microns to about 5 centimeters and, preferably, from about 1 centimeter to about 3 centimeter. The particle analyzer 210 is flexible and deformable. It has relatively thin walls. Thus, e.g., the difference between its internal diameter and its external diameter is generally from about 50 microns to about 3 millimeters and, more preferably, from about 50 microns to about 500 microns.

When radiation 220 impacts the outer surface 222 particle analyzer 210, less than 0.5 percent of such radiation is transmitted through the particle analyzer 210, and less than about 0.5 percent of such light rays are absorbed. As will be apparent, this property of optical impermeability insures that the sensing function of particle analyzer 210 is not affected by radiation emanating from outside of such particle analyzer 210.

In order to effect such optical impermeability, it is preferred that the casing 212 be made from an optically impermeable material which, additionally, is biocompatible with the living organism. Thus, e.g., casing 212 may be made, e.g., from a polymer composite material. One may use, e.g., any of the biocompatible optical shields with the required transmittance and absorbance properties.

In one embodiment, the casing 212 is comprised of a flexible biocompatible material with the ability to inhibit the transmission of optical energies into the lumen of the stent. Thus, for example, one may use one or more of the biocompatible materials disclosed in U.S. Pat. No. 6,124,523. This patent discloses an encapsulated stent including a stent or structural support layer sandwiched between two biocompatible flexible layers. One preferred embodiment has a stent cover which includes a tubular shaped stent that is concentrically retained between two tubular shaped grafts of expanded polytetrafluoroethylene. Another preferred embodiment has a stent graft which includes at least one stent sandwiched between the ends of two tubular shaped grafts wherein at least a portion of the grafts are unsupported by the stent.

In one embodiment, casing 212 is comprised of or consists essentially of polytetrafluorethylene. In additional embodiments, other biocompatible fluoroplastic materials may be used for casing 212.

Referring again to FIG. 4, the particle analyzer 210 is comprised of means for delivering one or more anticoagulants and/or proteinases or to bodily fluid flowing within the particle analyzer 210 at a controlled delivery rate. In one preferred embodiment, the process described in U.S. Pat. No. 5,865,814 (the entire disclosure of which is hereby incorporated by reference into this specification) is used to deliver anticoagulant and/or proteinase at a specified rate. This patent discloses a medical device for use in contact with circulating blood comprising: (a) a medical device having a blood-contacting surface; (b) a first coating layer on the blood-contacting surface consisting essentially of water soluble heparin; and (c) a second coating layer comprising a porous polymer overlaying the first coating layer such that heparin is elutable from the medical device through the second coating layer.

Referring again to FIG. 4, and in the preferred embodiment depicted therein, it will be seen that particle analyzer 210 is comprised of a multiplicity of optical assemblies 224. In the preferred embodiment depicted in FIG. 4, these optical assemblies 224 are preferably each equipped with an emitter (not shown in FIG. 4) and a photodetector (not shown in FIG. 4) in a monolithic configuration.

Referring again to FIG. 4, it will be seen that the optical assemblies 224 are present on the interior surface 226 of the particle analyzer 210 at a density of from about 3 to about 10 such optical assemblies 224 per square millimeter of interior surface 226 and, more preferably, at a density of from about 4 to about 7 such optical assemblies 224 per square millimeter of interior surface 226.

In one preferred embodiment, the optical assemblies 224 are uniformly distributed on the interior surface 226 of the particle analyzer 210. In another embodiment, illustrated in FIG. 4, the light emitting systems are recessed from each end edge 215 and 217 by a distance of at least about 2 millimeters to minimize the opportunity for spurious radiation entering the ends of particle analyzer 210 and causing false readings.

Each optical assembly 224 is preferably comprised of means for both emitting light and sensing light. The light emitter (not shown in FIG. 4) is preferably adapted to emit light across the electromagnetic spectrum, from a wavelength of from about 30 nanometers to about 30 microns (far infrared), and more preferably a wavelength of from about 350 (ultraviolet and argon lasers) to about 900 nanometers.

In general, the light emitting system may emit any electromagnetic radiation. It is preferred, however, that at least one of the forms of electromagnetic radiation emitted is optical radiation.

In one embodiment, the optical spectra emitted by any particular optical assembly 224 may differ from the optical spectra emitted by another such optical assembly 224. As will be discussed elsewhere in this specification, periodic arrays of such optical assembly 224 with differing optical outputs may be used.

In addition to containing means for emitting light, the optical assemblies 224 also preferably contain means for detecting light of specified optical properties, as will be discussed in more detail elsewhere in this specification.

Figure 5:
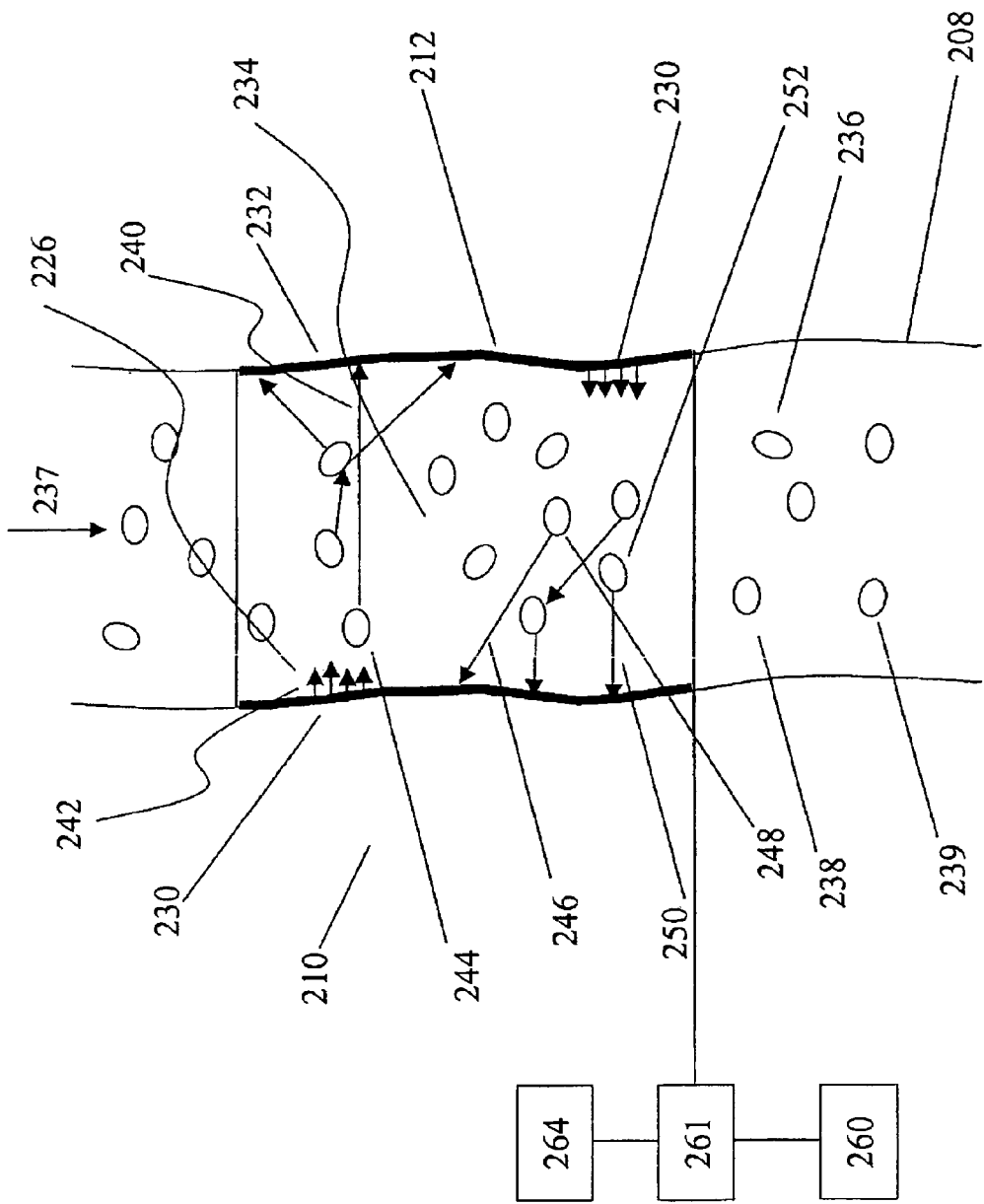
FIG. 5 is a sectional view of the particle analyzer sub-assembly of FIG. 4 inserted within a living organism.

FIG. 5 is a partial sectional view of the particle analyzer 210, taken through lines 202—202 of FIG. 4. For the purposes of illustration, the various components and cells depicted in FIG. 5 are not drawn to scale.

Referring to FIG. 5, it will be seen that casing/flexible substrate 212 has disposed on its interior surface 226 (see FIG. 4) light emitting devices 230 and light sensing devices 232. Although, in the embodiment depicted in FIG. 5, devices 230 and 232 are shown separately disposed within casing 212 for the sake of simplicity of representation, it should be understood that the devices 230 and 232 are preferably part of one monolithic construct of optical assembly 224. Reference may be had, e.g., to FIG. 7.

In one embodiment, the preferred light emitting device 230 is a "vertical cavity surface emitting laser" (VCSEL). A VCSEL emits light perpendicular to the wafer as the name implies. An advantage of VCSELs is that they are capable of being modulated at high speeds with much lower electrical power than in-plane lasers. In addition, the geometry of VCSELs makes them particularly suitable for making two-dimensional arrays, and for on-wafer testing. These characteristics can reduce the cost of packaging (which dominates the cost of manufacturing) and costs of the driver circuitry required.

Referring again to FIG. 5, and in the embodiment depicted therein, a bodily fluid 234 is flowing in the direction of arrow 237. In one embodiment, the bodily fluid 234 is blood, and it is caused to flow by the action of a heart.

In another embodiment, the bodily fluid may be a non-hematologic fluid such as, e.g., lymph, urine, cerebrospinal fluid, and the like.

In one embodiment, the bodily fluid 234 is comprised of plasma. In another embodiment, the bodily fluid 234 is comprised of red blood cells 236, and/or leukocytes 238, and/or neutrophils 239, and/or other cells or cellular material. The bodily fluid can also comprise any cell type which may begin to circulate within the blood/lymph/urine. Each of these components will have a different optical response to a specified optical input.

Thus, referring again to FIG. 5, the cells preferably have either endogenous optical properties, and/or they are labeled to provide optical properties. Thus, e.g., the cells may be labeled with flourescently-conjugated antibodies. Thus, e.g., in one embodiment the particle analyzer 210 will utilize either injected fluorescent contrast or emitted light energies intrinsic to specific cells themselves. As is known to those skilled in the art, antibodies may be conjugated with polymeric dies with fluorescent emission moieties such as aminostyryl pyridinium (see, e.g., U.S. Pat. No. 5,994,143, the entire disclosure of which is hereby incorporated by reference into this specification).

As is apparent, and in one preferred embodiment, the function of particle analyzer 210 is to determine which, if any, of four antigens are carried by blood cells. To this end, respective antibodies for the antigens are derivatized with respective fluorochromes allophycocyanin (APC), peridinin chlorophyl protein (PerCP), fluorescein isothiocyanate (FITC), and R-phycoerythrin (RPE). Reference may be had, e.g., to U.S. Pat. No. 5,682,038 for "Fluorescent-particle analyzer with timing alignment for analog pulse subtraction of fluorescent pulses arising from different excitation locations," the entire disclosure of which is hereby incorporated by reference into this specification.

By way of further illustration, U.S. Pat. No. 5,994,143 ("Polymeric fluorophores enhanced by moieties providing a hydrophobic and conformationally restrictive microenvironment") discloses another process for fluorescent antibody conjugation; the entire disclosure of this United States patent is hereby incorporated by reference into this specification. In this patent, it is disclosed that the first of two closely positioned fluorophores may be excited by light of a given wavelength. Then, instead of emitting light of a longer wavelength, the excited fluorophore transfers energy to the second fluorophore. That transferred energy excites the second fluorophore, which then emits light of an even longer wavelength than would have been emitted by the first fluorophore. An example of such an energy transfer arrangement involves phycobiliprotein-cyanine dye conjugates. Subjecting these conjugates to an about 488 nm laser light excites the phycobiliprotein. The phycobiliprotein will then, without itself irradiating, transfer energy to the cyanine fluorophore at the excitation wavelength of the cyanine, which is coincident with the emission wavelength of the phycobiliprotein, about 580 nm. Consequently, the cyanine fluorophore is thereby excited and subsequently emits light of its emission wavelength of about 680 nm. This type of energy transfer system in often referred to as a "tandem energy transfer system."

In one embodiment, not shown, fluorescent dyes are injected upstream of the particle analyzer 210, preferably into a venous blood supply. The dyes may be injected in a manner similar to that used to inject contrast agents for medical ultrasound techniques. See, e.g., U.S. Pat. Nos. 6,177,062 ("Agents and methods for enhancing contrast in ultrasound imaging"), the entire disclosure of each of which is hereby incorporated by reference into this specification. The fluorescent dyes preferably are not toxic to the living body and care must be taken in preparation of the fluorescent dyes. The combination of different wavelength fluorochromes conjugated to antibodies to different cells along with the endogenous optical properties of the cells will provide a complex multiparameter data set where differing signals from different cells will be discernable.

In one embodiment, depicted in FIG. 5, the particle analyzer 210 detects the intrinsic scattering properties of cells (which are influenced by the cellular membrane structure, organelle concentration and structure, cytoplasmic structure, and DNA/chromatin structure) and/or emitted light from fluorescently labeled cells.

Referring again to FIG. 5, the particle analyzer 210 is contacting the bodily fluid 234 with a multiplicity of different optical radiations 242, and a multiplicity of different phenomena are occurring which are sensed by the particle analyzer 210.

Thus, by way of illustration, light emitting device 230 emits optical radiation 242 that contacts cell 244, which is transmitted directly through the cell 244, and which emerges as radiation 240. The emitted radiation 240 is detected by light sensing device 232. As will be apparent to those skilled in the art, this process is often referred to as "forward light scattering."

In addition to detecting forward light scattering, the particle analyzer 210 is also capable of detecting the scattered light that is reflected orthogonal to the direction of the flow ("side light scattering"). Reference may be had to radiation 246 scattered by cell 248.

Furthermore, the particle analyzer 210 may also detect the fluorescence emission from fluorescently conjugated antibodies to a variety of factors within and on the cell surface. Reference may be had, e.g., to radiation 250 emitted by cell 252.

In one embodiment, and referring again to FIG. 5, the particle analyzer 210 is comprised of a telemetry device 260, such as a transceiver 260, which may be disposed within or without a person's body. One may use any of the implantable telemetry devices known to those skilled in the art. Reference may be had, e.g., to an article by Z. Hamici entitled "A high-efficiency power and data transmission system for biomedical implanted electronic devices," published in Measurement Science Technology 7 (1996), at pages 192–201. The authors of this article described a new system energizing an implanted micro-telemeter that transmits internal digital data to a remote receiver.

By way of further illustration, one may use the transceiver disclosed in U.S. Pat. No. 5,972,029 ("Remotely operable stent"). In the process of this patent, the diameter of the stent is varied mechanically using strut mechanisms that are operatively connected to the transceiver. The transceiver of this patent utilizes electromagnetic radiation in the infrared region.

Similarly, one may use the telemetry system disclosed in U.S. Pat. No. 5,843,139 ("adaptive, performance-optimizing communication system for communicating with an implanted medical device").

Regardless of the telemetry system used, it is also understood that the telemetric device may not only use radio frequency energy for telemetric functions but also may utilize acoustic energy. Reference may be had, e.g., to U.S. Pat. No. 6,170,488 ("Acoustic-based remotely interrogated diagnostic implant device and system"), the entire disclosure of which is hereby incorporated by reference into this specification.

Referring again to FIG. 5, it will be apparent that, for any particular bodily fluid sample at any particular point in time, there will be a multiplicity of radiations emitted by the particle analyzer 210, and a multiplicity of radiations sensed by the particle analyzer 210. Thus, the particle analyzer 210 is capable of detecting a myriad of different conditions and/or phenomena. The data so detected will be processed by a controller 264, which is preferably operatively connected to both telemetry device 260, light emitting devices 230, and a waveguide layer (see, e.g., layer 272 in FIGS. 7a and 7b).

Referring again to FIG. 5, the controller 264 and/or the telemetry device 260 are powered by power supply 261. One may use conventional power supplies. Thus, by way of illustration, one may use a lithium-iodine battery, and/or a battery that is chemically equivalent thereto. The battery used may, e.g., have an anode of lithium or carbon and a cathode of iodine, carbon monofluoride, or of silver vanadium oxide, and the like.

By way of further illustration, one may use one or more of the batteries disclosed in U.S. Pat. No. 5,658,688 ("lithium-silver oxide battery and lithium-mercuric oxide battery"), U.S. Pat. No. 4,117,212 ("lithium-iodine battery"), and the like. The entire disclosure of each of these United States patents is hereby incorporated by reference into this specification.

Figure 10:
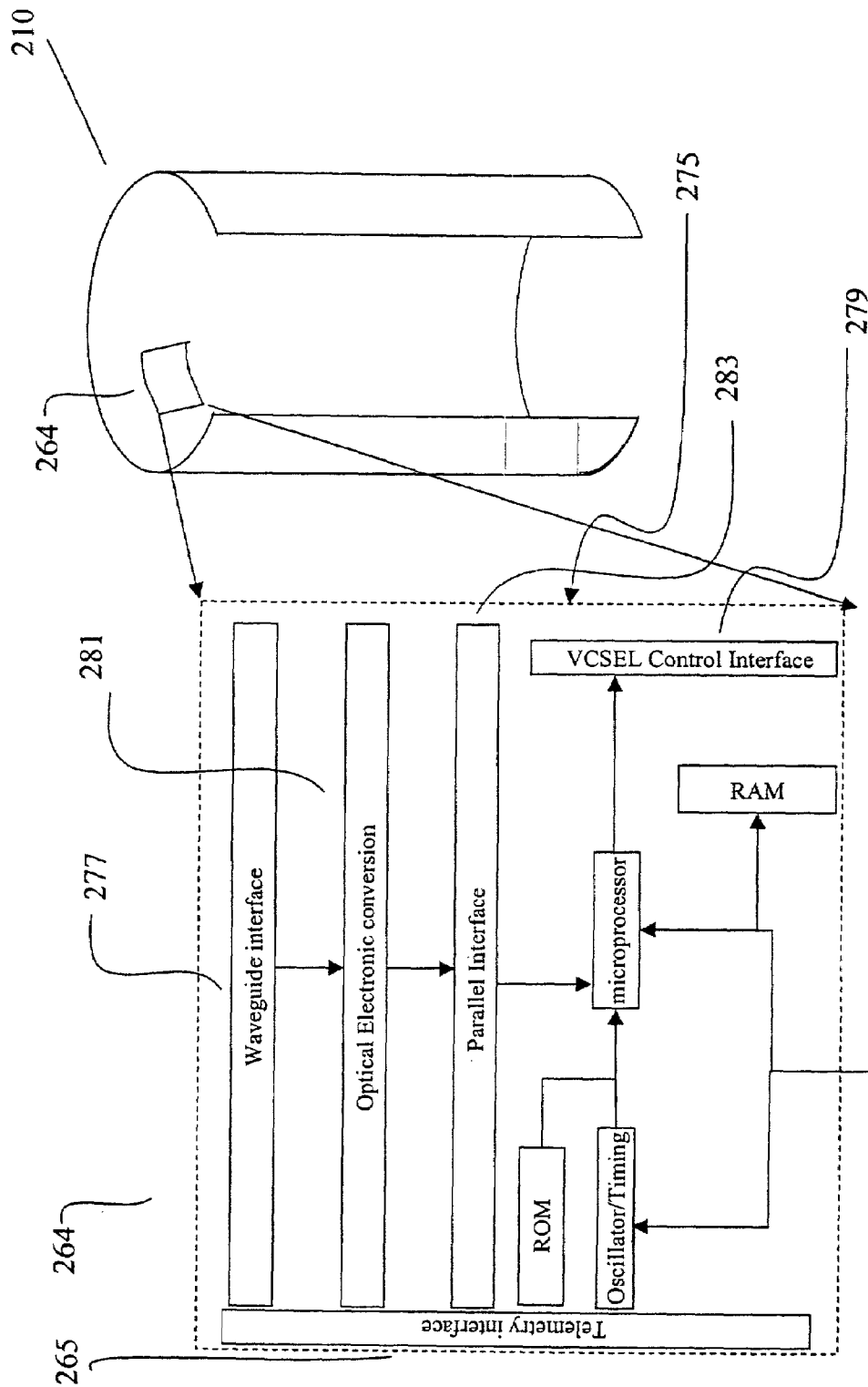
FIG. 10 is a partial exploded view of the particle analyzer sub-assembly of FIG. 4 illustrating a preferred controller/signal processor used therein.

In one embodiment, illustrated in FIG. 10, the power supply 261 is incorporated into the housing of the controller/processor 264.

The telemetry device 260 and the controller 264 may be used with the other components of applicant's particle analyzer 210 to evaluate, process, store, and utilize the information detected from the bodily fluid.

Because many different types of data are analyzed for any particular bodily fluid sample, the particle analyzer 210 is capable of accurately analyzing many different conditions.

By way of illustration, and by reference to the process depicted in U.S. Pat. No. 6,014,904, one may analyze the bodily fluid and its constituents. This patent discloses a method for automatically classifying multi-parameter data into cluster groups for the purpose of defining different populations of particles in a sample by automatically defining a position of at least one variable position, geometric boundary surface on a two-dimensional scatter plot so as to enclose a group of the displayed particles in a data cluster, with the boundary surface having a polygonal shape defined by a plurality of vertices about at least one cell cluster created by building at least one histogram from cross sections of the two-dimensional gate. The method is particularly useful in the field of cellular analysis using, for example, flow cytometers wherein multi-parameter data is recorded for each cell that passes through an illumination and sensing region. The entire disclosure of this United States patent is hereby incorporated by reference into this specification.

By way of further illustration, multiparameter data sets acquired from the various photo-detectors may be processed with algorithms such as that taught in U.S. Pat. No. 5,627,040. The entire disclosure of this United States patent is hereby incorporated by reference into this specification.

By way of yet further illustration, one may use the technology of one or more of the patents described below for analyses of the many different signals to be received by the array of photodetectors. U.S. Pat. No. 5,880,474 ("Multi-illumination-source flow particle analyzer with inter-location emissions crosstalk cancellation") describes a process in which the photodetector output signals are processed by analog signal processor, which includes a crosstalk cancellation integrated circuit, a transit delay circuit, an amplifier bank, a pulse processor, a peak holder, and an analog-to-digital converter (ADC).

U.S. Pat. No. 5,602,647, for "Apparatus and method for optically measuring concentrations of components," discloses an apparatus and method for optically measuring concentrations of components which allows enhancement in measurement accuracy of concentration. In the process of this patent, and in one embodiment of the process of applicant's patent, an array of photodetectors is arranged in parallel to the surface of a multiplicity of cells, so that it can detect intensity of rays of transmitted light and/or fluorescent emissions that have traveled over different optical path lengths at positions of an equal distance from the cell. The arithmetic unit, receiving a signal from the individual photodetectors, calculates concentrations of components in the sample based on optimum optical path lengths for different wavelengths and values of transmitted light at positions of the optimum optical path lengths, and further outputs calculation results. The entire disclosure of this patent is hereby incorporated by reference into this specification.

By way of further illustration, in U.S. Pat. No. 5,682,038, for "Fluorescent-particle analyzer with timing alignment for analog pulse subtraction of fluorescent pulses arising from different excitation locations," additional methods are described to alleviate crosstalk. it will be apparent that, with regard to applicants' process, the number of distinguishable fluorochromes can be increased by using more than one excitation wavelength. This approach takes advantage of the fact that fluorochromes differ not only in their emissions spectra, but also in their excitation spectra. In an ideal case, two fluorochromes with non-overlapping excitation spectra could be distinguished even where the emissions spectra were identical. The distinction could be achieved by illuminating the fluorochromes at different times with two lasers, each selected to excite only a respective one of the fluorochromes. The resulting emissions would appear as two distinct pulses in the output of a single photodetector.

The U.S. Pat. No. 5,682,538 patent discloses an approach that is implemented in the context of a flow cytometry system by illuminating different locations along a flow tube with different laser wavelengths, each of which preferentially excites a respective fluorochrome. As is disclosed in such patent, tagged cells are made to flow serially past the two locations. When a cell is at the first location, a photodetector pulse corresponds to the first fluorochrome; when later the cell is at a second location, a photodetector pulse corresponds to the second fluorochrome. The pulses are routed and at least minimally processed in the analog domain; they are then converted to digital data that can then be manipulated in the digital domain to provide the desired information about the cells.

As is disclosed in U.S. Pat. No. 5,682,538, in such a flow cytometry system, each pulse generated corresponds predominantly to a respective fluorochrome. Because of overlapping emissions and excitation spectra, each pulse can include contributions, i.e., "crosstalk", from other fluorochromes. Two types of crosstalk can be distinguished: "intrabeam" crosstalk results from overlap in the emissions spectra of fluorochromes excited by a common laser beam; "interbeam" crosstalk results from the overlap in the excitation spectra of fluorochromes excited by different laser beams. There are optical techniques for reducing both types of crosstalk, but they are incomplete. Accordingly, post-detection correction of crosstalk is required.

By way of further illustration, U.S. Pat. No. 5,632,538 discloses that the mathematics of crosstalk reduction is well understood. In general, crosstalk can be removed from a measurement primarily corresponding to one fluorochrome by subtracting a crosstalk term that is a function of measurements primarily corresponding to the other fluorochromes. More specifically, the crosstalk term can be a sum of product terms; each product term is a fluorochrome measurement multiplied by a coefficient. The coefficients can be determined empirically during a calibration run.

Figure 6:
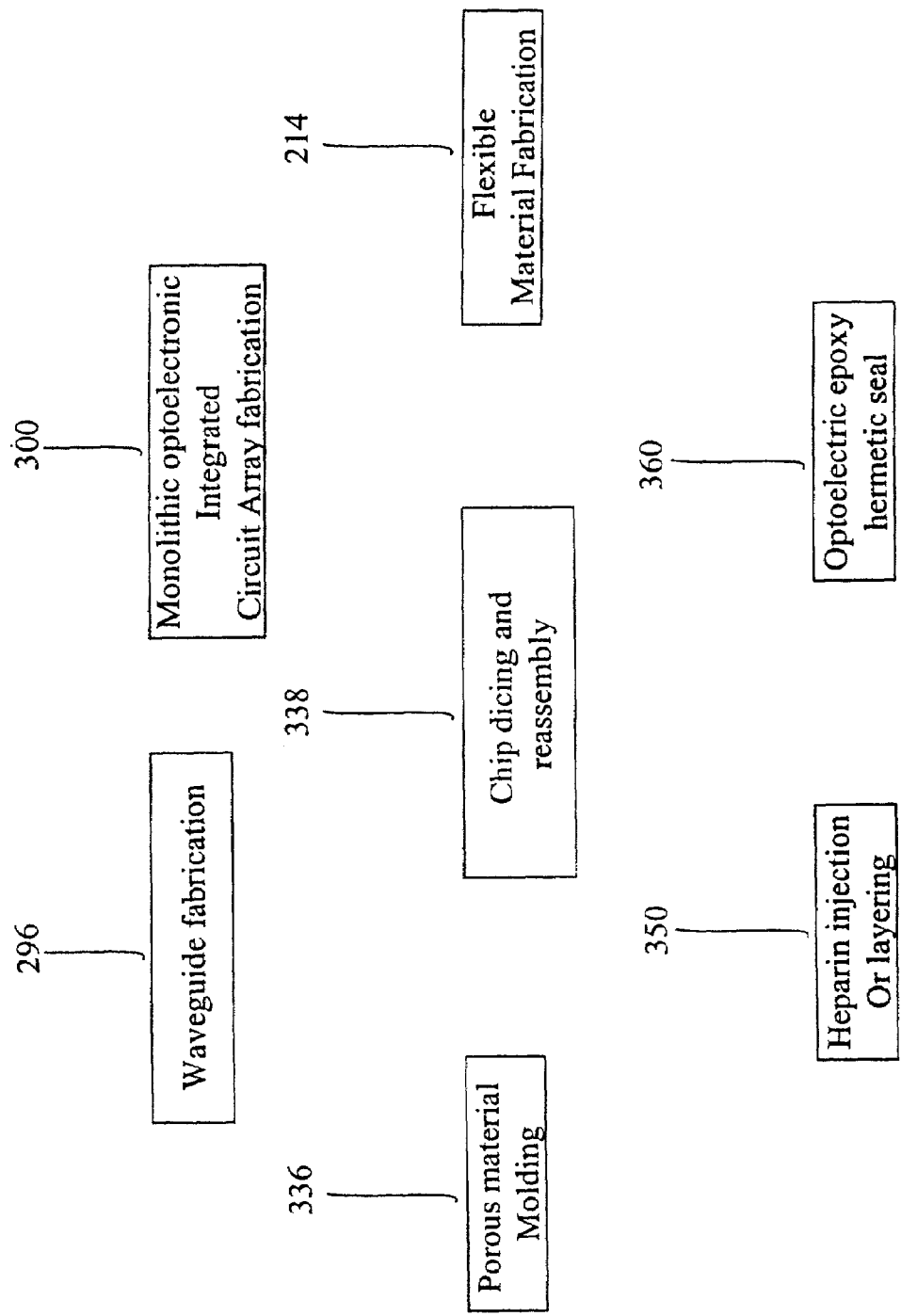
FIG. 6 is a flow diagram illustrating one preferred process for producing the particle analyzer sub-assembly of FIG. 4.
Figure 7A:
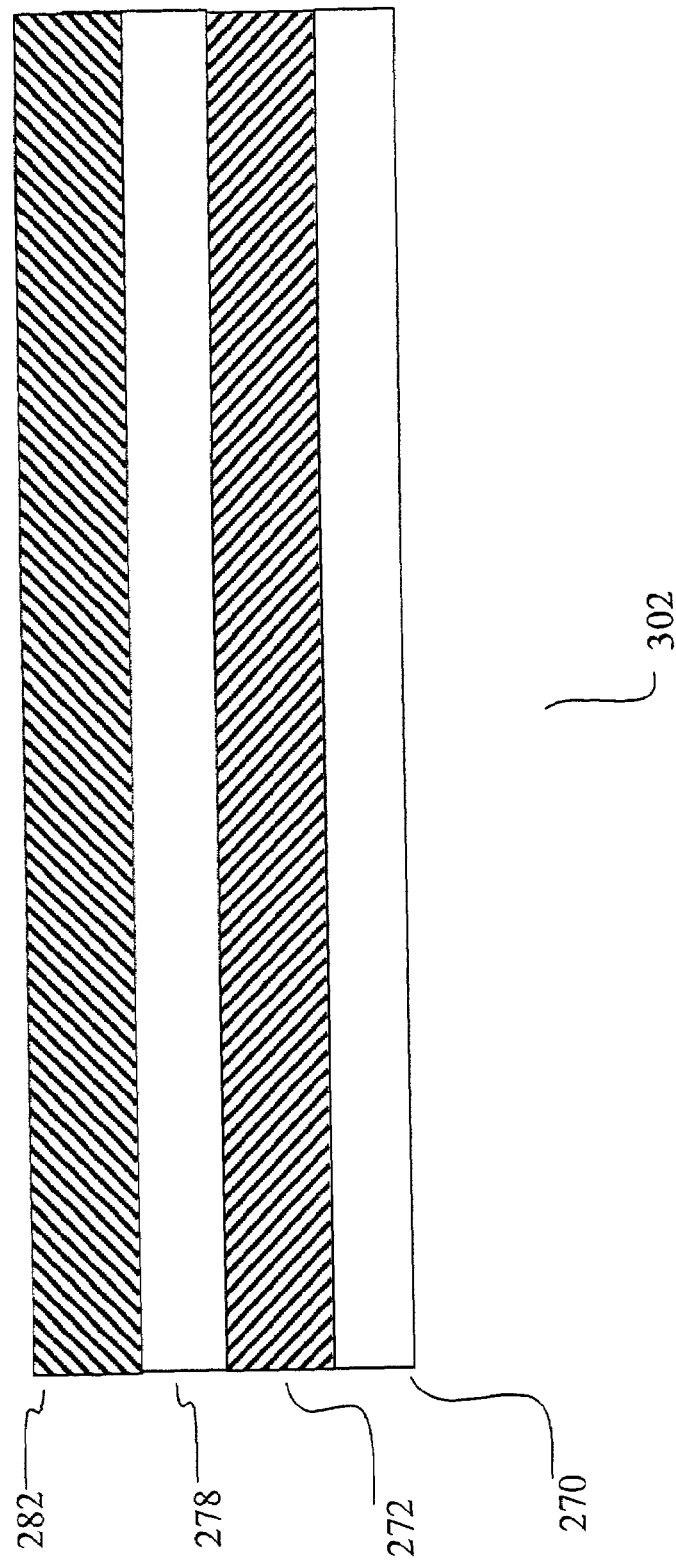
FIG. 7a is a schematic of one preferred epitaxial structure during fabrication of one preferred monolithic integrated circuit chip that is used in the sub-assembly of FIG. 4.

FIG. 6 is a flowchart illustrating one preferred fabrication process of the instant sub-assembly. Referring to FIG. 6, and in the preferred embodiment depicted therein, in step 300 an optoelectronic integrated circuit is fabricated onto a substrate. One preferred embodiment for an epitaxial structure 302 to eventually become the integrated circuit fabricated in step 300 is illustrated in FIG. 7a. The embodiment depicted in FIG. 7a may be produced in substantial accordance with the procedure described in U.S. Pat. No. 6,148,016 ("Integrated semiconductor lasers and photodetectors"), the entire disclosure of which is hereby incorporated by reference into this specification. This patent discloses and claims a method for fabricating a vertical cavity laser adjacent to a vertical cavity photodetector, through the fabrication of an epitaxial structure comprising a substrate, a first mirror, a second mirror, and an emission/absorption cavity between said first and second mirrors.

Figure 7B:
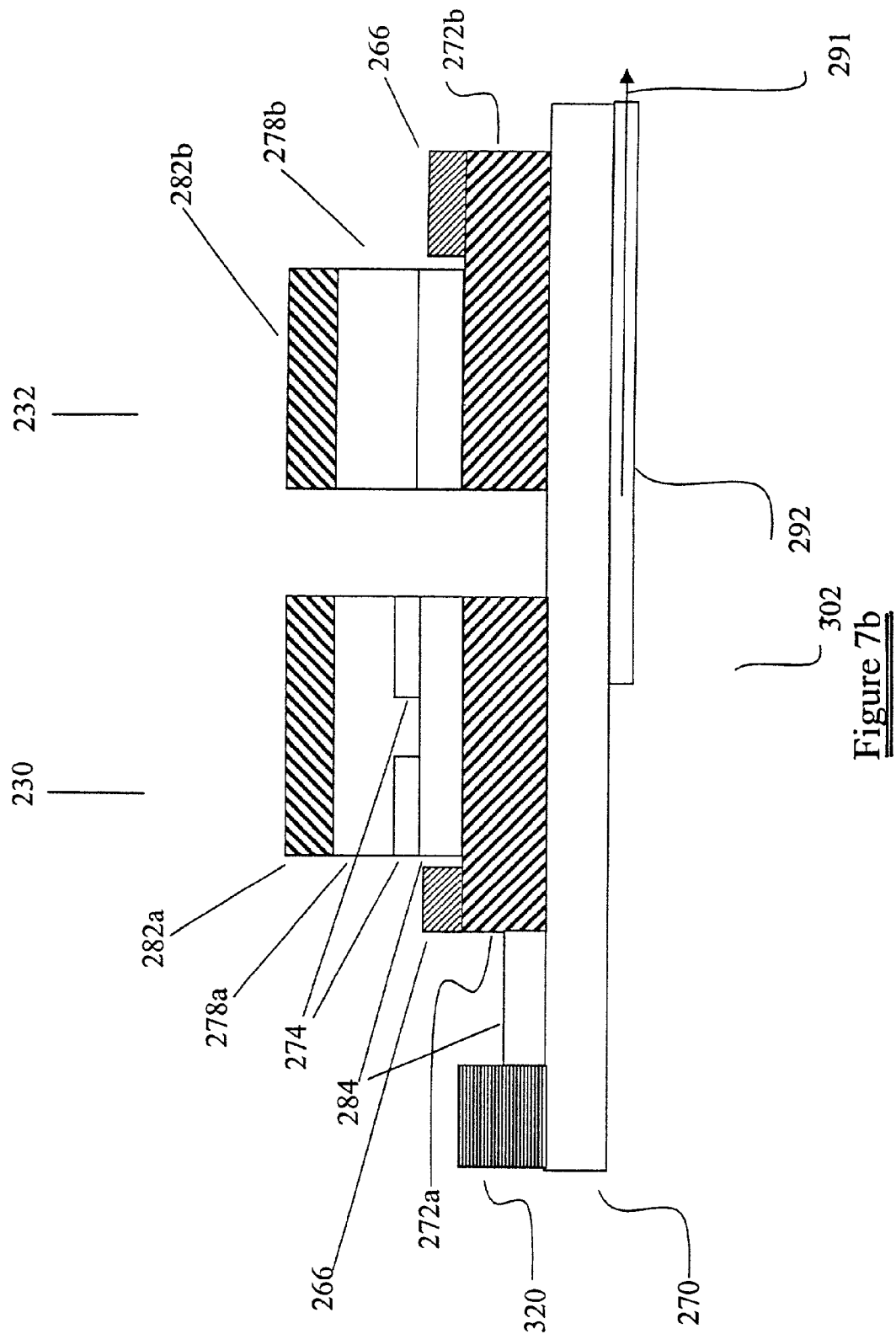
FIG. 7b is a schematic of one preferred monolithic integrated circuit chip which is used in the sub-assembly of FIG. 4.

In the embodiment depicted in FIGS. 7A and 7B, unnecessary and/or conventional detail has been omitted for the sake of simplicity of representation.

As will be apparent, and by means of further illustration, the device depicted in FIGS. 7a and 7b may be constructed by conventional means such as, e.g., the procedure disclosed in U.S. Pat. No. 6,097,748 ("Vertical cavity surface emitting laser semiconductor chip with integrated drivers and photodetectors and method of fabrication"), the entire disclosure of which is hereby incorporated by reference into this specification. This patent discloses and claims a vertical cavity surface emitting laser semiconductor chip comprising: (a) a vertical cavity surface emitting laser formed on a substrate; (b) a photodetector, integrated with the vertical cavity surface emitting laser for automatic power control of the vertical cavity surface emitting laser; and (c) a laterally integrated driver circuit, formed on the substrate, and about a periphery of the substrate, the driver circuit characterized as receiving feedback from the photodetector and adjusting an output power of the vertical cavity surface emitting laser in response to the feedback. Each of these elements is present in applicants' device.

Referring again to FIG. 7a, and in the preferred embodiment depicted, substrate 270 preferably consists essentially of ceramic semiconductor material such as, e.g., such as gallium arsenide, silicon, sapphire, mixtures thereof, and the like. Other suitable semiconductor materials will be apparent to those skilled in the art.

Referring again to FIG. 7b, and in one embodiment, one device of this invention comprises an integrated vertical cavity laser/photodetector for optical assembly 224. As is known to those skilled in the art, the vertical cavity laser comprises a substrate, a bottom mirror, a top mirror and a cavity with a gain medium between the top and bottom mirrors. The gain medium typically comprises quantum wells which, when electrically or optically pumped, will emit light. The mirrors typically comprise distributed bragg reflectors (DBRs) formed from alternating high/low index quarter-wave thick layers. Multilayer stacks are generally used for the mirrors instead of metal due to the high reflectivity (>99%) needed to achieve lasing because the gain medium is so thin. Bottom-emitting or top-emitting VCSELs have a partially transmissive bottom or top mirror, respectively. Because of the highly reflectivity mirrors and short cavity used in VCSELs, the lasing wavelength is controlled by the resonant wavelength of the cavity, rather than the peak of the gain as in in-plane lasers.

Referring again to FIG. 7a, disposed on substrate 270 is a distributed multi-layered bottom bragg reflector (DBR) 272; and, deposited onto the DBR 272 is an emission/absorption cavity 278. Thereafter, a second, multilayered top DBR 282 is deposited onto the emission/absorption cavity 278.

The multi-layered bottom and top DBRs 272 and 282, as well as emission/absorption cavity 278 generally are preferably made of layers of aluminum gallium arsenide. These layers of the bottom and top DBRs 272 and 282 are fabricated so that an aluminum concentrations of these layers vary alternately in concentration. The reflectivity of a particular layer is a function of, e.g., its aluminum concentration. It is preferred that the bottom DBR layer 272 have a lower aluminum concentration than the top DBR layer 282.

Additionally, the bottom and top DBRs 272 and 282 are preferably alternately doped with either a p-type dopant or an n-type dopant. For example, the top DBR 282 can be doped with the n-type dopant, whereas the bottom DBR 272 can be doped with the p-type dopant.

Emission/absorption cavity 278 is also made of a variety of layers. Emission/absorption cavity 278 is typically made of a quantum well with barrier regions on either side of the quantum well using any suitable materials. Generally, the barrier regions and the quantum well are made of undoped aluminum gallium arsenide, and gallium arsenide, respectively, each having a thickness of approximately 100 Angstroms. It should be understood by one of ordinary skill in the art that additional barrier layers and quantum wells can be added to improve performance of the emission/absorption cavity 278.

Referring to both FIGS. 7a and 7b, the bottom and top DBRs 272 and 282, emission/absorption cavity 278, and contacts 266 may be disposed or grown on substrate 270 by any suitable epitaxial method or technique, such as "Metal Organic Chemical Vapor Deposition" (MOCVD), "Molecular Beam Epitaxy" (MBE), "Chemical Beam Epitaxy" (CBE), or the like. Referring again to FIG. 7a, the DBR/cavity/DBR layers of the light emitting device 230 and light sensing device 232 are separated using conventional etching.

Most VCSELs are "top emitting" devices, that is, light is emitted outward or away from the top surface of the device. However, bottom-emitting devices, where light is emitted through the substrate, are advantageous for systems with arrays of vertical cavity lasers, because the driver circuitry can then be "flip-chip bonded" to the array instead of making individual wire bonds. Referring again to FIG. 7b, the placement of the driver circuitry 320 on the substrate 270 is depicted. Reference to such driver circuitry can be found in U.S. Pat. No. 6,097,748 ("Vertical cavity surface emitting laser semiconductor chip with integrated drivers and photodetectors and method of fabrication"), the entire disclosure of which is hereby incorporated by reference into this specification.

Disposed on substrate 270 are air/oxide isolators 274, which isolate electromagnetic radiation and prevent spurious radiation leakage out of the emission cavity region 278a within the VCSEL. As is known to those skilled in the art, these air/oxide isolators are often made of any suitable dielectric material, such as silicon dioxide ($SiO_2$), silicon nitride ($Si_3N_4$), or the like.

Referring again to FIG. 7b, the conductive layer 284 and contacts 266 are preferably made of any suitable conductive material, such as a metal (e.g., gold, silver, copper, aluminum, tungsten, an alloy (e.g., aluminum/copper (Al/Cu), titanium tungsten (TiW)), or the like. Deposition of the conductive layer 284 and the contacts 266 can be achieved by conventional means such as, e.g., sputtering, evaporation, and the like.

The specific thickness of conductive layer 284 will change with specific applications and designs. Such thickness of conductive layer 284 can range from 2,000 to 10,000 Angstroms, with a preferred range from about 3,000 to about 8,000 Angstroms, and having a nominal thickness of 4,000 Angstroms.

As is apparent, a masking layer can be patterned to make openings that expose portions of the surface to be masked. The masking layer can be made by any suitable lithographic process, such as photolithography, X-ray lithography, or the like. Generally, lithographic processes are well known in the art; however, by way of example, a brief explanation of a positive photolithographic process is provide herein below.

In such a process, a photolithographic material, such as photoresist, or the like, is applied to a surface. The photolithographic material is exposed with a pattern of light and developed, thereby providing open areas as well as covered areas. The pattern that is used to expose the photolithographic material can form any number of geometric patterns and designs, such as rings, ovals, lines, squares, or the like.

After the exposing and developing processes of the masking layer, the substrate or surface is ready to be etched. The surface of substrate 270 is etched in any suitable etch system that provides an anisotropic etch profile. Further, any suitable etch chemistry is used for etching substrate 270/surface, such as a fluorine based chemistry, a chlorine based chemistry, or the like. Generally, fluorine based chemistry is used to etch or remove a variety of materials, such as nitride, silicon dioxide, tungsten, titanium tungsten, and the like; whereas the chlorine based chemistry also is used to remove a variety of material, such as semiconductor materials, e.g., silicon, gallium arsenide, aluminum gallium arsenide, as well as conductive materials, such as aluminum, e.g., copper, aluminum, and the like. Additionally, it should be understood that these chemistries can be used in the same etching system, thereby enabling a multitude of layers or different materials to be etched in one etching system. Thus, the process of manufacturing a vertical cavity surface emitting laser is more manufacturable.

Referring again to FIG. 7b, an optical waveguide 292 is contiguous with porous layer 334 (see FIG. 11 for more detail) and is adapted to transmit light in directions of arrow 291. It is preferred that the optical waveguide 292 be fabricated of glass and that the substrate be silicon. See U.S. Pat. No. 6,167,168.

In one preferred embodiment, optical waveguide layer 292 has a geometry adapted to transmit visible light at a high efficiency. Reference may be had to, e.g. U.S. Pat. No. 6,167,168 ("Arrangement of optical waveguides"), the entire disclosure of each of which is hereby incorporated by reference into this specification. The optical waveguide(s) 292 may be coupled, one to another, or to light sensing device 232, by conventional waveguide coupling means. See, e.g., U.S. Pat. No. 5,805,751 ("Wavelength selective optical couplers"). The entire description of each of these United States patents is hereby incorporated by reference into this specification.

In one embodiment, depicted in FIG. 7b, the optical waveguide 292 is positioned under only the light sensing device 232 region and is not so positioned under light emitting device 230.

In one embodiment, not shown, the epitaxial structure 302 comprises at least two optical waveguides 292 of which each comprises an input-side end for coupling an optical waveguide into the waveguides, a respective output-side end for coupling out the optical waveguides conducted in the waveguide, and a determined optical length between the two ends. In one aspect of this embodiment, the epitaxial structure 302 contains first means for producing a modification of the optical length of the waveguide so that in a waveguide, the produced modification of the optical length is smaller than in another waveguide.

In one embodiment, not shown, the waveguides are arranged next to one another at a spatial distance small enough that the optical waves coupled out from these ends are superposed coherently on one another and that at least two of the waveguides are dimensioned so that their optical length is different from one another and that the optical length is modified to increase from wavelength to wavelength. Preferably, two means are provided, with the first means causing different amounts of increase of wavelength in one direction, while the second means causes decreasing amounts of change in wavelength the one direction.

In one embodiment, not shown, there is utilized a phased array with several optical waveguides with optical lengths that increase from waveguide to waveguide. This phased array has a first arrangement for modifying the optical length of waveguides, with the modification increasing from waveguide to waveguide in one direction, and a second arrangement for producing a modification of the optical length, with the modification decreasing from waveguide to waveguide in the one direction.

The aforementioned discussion regarding waveguides is known to those skilled in the art. Thus, for example, in U.S. Pat. No. 6,091,874 ("Flexible optical waveguide device and process for the production thereof") there is disclosed a flexible optical waveguide device obtained by forming a refractive index distribution in a light-permeable polymer film to obtain an optical wave-guide film and forming a cured resin layer on at least one surface of the optical wave-guide film, the cured resin layer(s) comprising, as main components, a polyamide resin, and at least one member selected from the group consisting of an epoxy resin and a phenolic resin; and the flexible waveguide used in applicants' device may be made in accordance with the process of such patent. The entire disclosure of which is hereby incorporated by reference into this specification.

In one embodiment, when fabrication of the optoelectronic devices and waveguides is completed the individual optical assemblies 224 are to be diced in the manner known to those skilled in the art.

Figure 8:
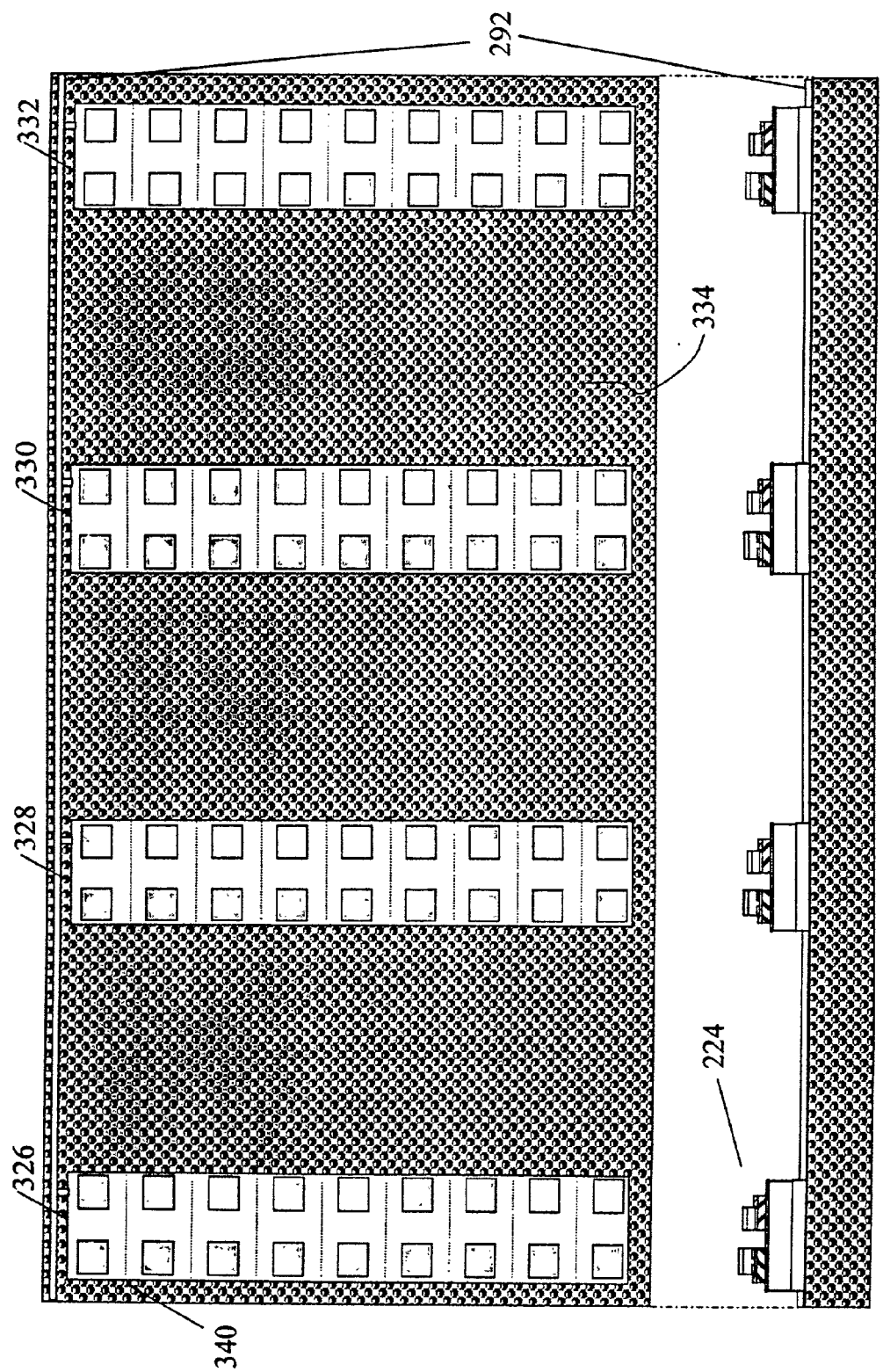
FIG. 8 is a schematic of a multiplicity of the monolithic integrated circuit chips of FIG. 7b disposed on a porous substrate and waveguide array.

The optical assemblies 224 are then assembled forming opto-electronic circuit arrays 326/328/330/332 (see FIG. 8). Each individual optical assembly 224 may be coupled to a flexible waveguide and linked by any suitable means (via, e.g., link 340) to the next device.

At temperatures required for the fabrication of the optical assembly 224 and the optical waveguide 292 (see FIG. 8), the stent portion of the device may be fabricated separately. In one preferred embodiment, the stent can be initially constructed as a flat layered sheet where a flexible biocompatible layer for outer casing 212 will then be coated with a solution of heparin and water. The outer edges of casing 212 can be seamed for when the device is formed into a cylinder. With regard to the application of heparin, and/or other anticoagulant, the heparin may be applied to the surface simply from aqueous solution or dispersion. For example, heparin can be applied from aqueous solution onto a stent body and allowed to dry. A heparin/water solution may be applied to the stent body in successive thin coats with drying and weighing of the stent between coats. When the total weight of coating on the stent indicates that the target dosage has been achieved, no additional heparin solution is applied. The overall coating should be thin enough so that it will not significantly increase the profile of the stent for intravascular delivery by catheter. It is therefore preferably less than about 0.002 inch thick and most preferably less than 0.001 inch thick. The porous polymeric overlayer can then be applied to the heparin coated stent body such that it controls the release of heparin from the coating.

FIG. 8 is a partial view of the interior surface 226 of particle analyzer 210 (see FIG. 4), showing it in a flat configuration to better illustrate its components. Referring to FIG. 8, it will be seen that opto-electronic circuit arrays 326, 328, 330, and 332 are bonded to porous layer 334. This bonding may be affected by conventional means such as, e.g., by the use of epoxy adhesive. Thus, e.g., one may use as an adhesive Emerson & Cuming Stycase® 1267 or 1269 transparent, high-impact casting resins or Epoxy Technology, Inc. Epo-tek® 301; these are spectrally transparent epoxies which have appropriate transmissions between 900 and 350 nanometers.

The structure depicted in FIG. 8 has several features in common with the structure claimed and disclosed in U.S. Pat. No. 5,865,814 ("Blood contacting medical device and method") the entire disclosure of which is hereby incorporated by reference into this specification. This patent claims a medical device for use in contact with circulating blood comprising: (a) a medical device having a blood-contacting surface; (b) a first coating layer on the blood-contacting surface consisting essentially of water soluble heparin; and (c) a second coating layer comprising a porous polymer overlaying the first coating layer such that heparin is elutable from the medical device through the second coating layer.

The porous layer 334 may be similar to or identical to the porous layer described in such patent. Thus, e.g., it may be comprised of a polymer selected from the group consisting of poly(lactic acid), poly(lactide-co-glycolide) and poly (hydroxybutyrate-co-valerate), and mixtures thereof. Thus, e.g., it may be comprised of a polymer selected from the group consisting of silicones, polyurethanes, polyesters, vinyl homopolymers and copolymers, acrylate homopolymers and copolymers, polyethers and cellulosics. Thus, e.g., it may have an average pore diameter in the range of about 0.5–10 microns.

The porous layer 334 may, but need not, comprise materials such as biomolecules, including, e.g., fibrin, fibrinogen, cellulose, starch, collagen and hyaluronic acid. Also, biostable polymers with a relatively low chronic tissue response such as polyurethanes, silicones, and polyesters could be used, and other polymers could also be used if they can be dissolved and cured or polymerized on the stent. Such polymers include, e.g., polyolefins, polyisobutylene and ethylene-alphaolefin copolymers; acrylic polymers and copolymers; vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile, polyvinyl ketones; polyvinyl aromatics, such as polystyrene, polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

A suitable porous coating can be provided, for example, by phase inversion precipitation of the polymer in the overlayer. According to this technique, a solution of a polymer is prepared in a mixture of two miscible solvents, one of which being a poorer solvent for this polymer and less volatile than the other solvent. When the solution is allowed to dry, there becomes a moment when the good solvent has sufficiently evaporated for causing the polymer to slowly precipitate which results, after complete drying, in an opened porous structure. For example, when using poly(L-lactic acid) as the polymer, a suitable solvent composition can include about a 40/60% (w/w) isooctane/chloroform solution. This solution should be mixed carefully to avoid precipitation during the mixing process. The better solvent for the polymer should dissolve the polymer first (i.e. a solution of poly(L-lactic acid) and chloroform should be made first). A mixture of the solvents should then be added to the polymer solution to bring the ingredients to the desired concentration (i.e. a mixture of isooctane and chloroform is added to the poly[L-lactic acid] solution). This mixture is then applied to the stent in the same manner as set forth above. It will be appreciated by those skilled in the art that the nature of the ingredients and the relative concentrations of the ingredients will determine the size of pores. Pores in the range of about 0.5 to 10 microns in diameter may be suitable. Phase inversion precipitation techniques are well known in the manufacture of porous polymeric membranes.

Figure 9:
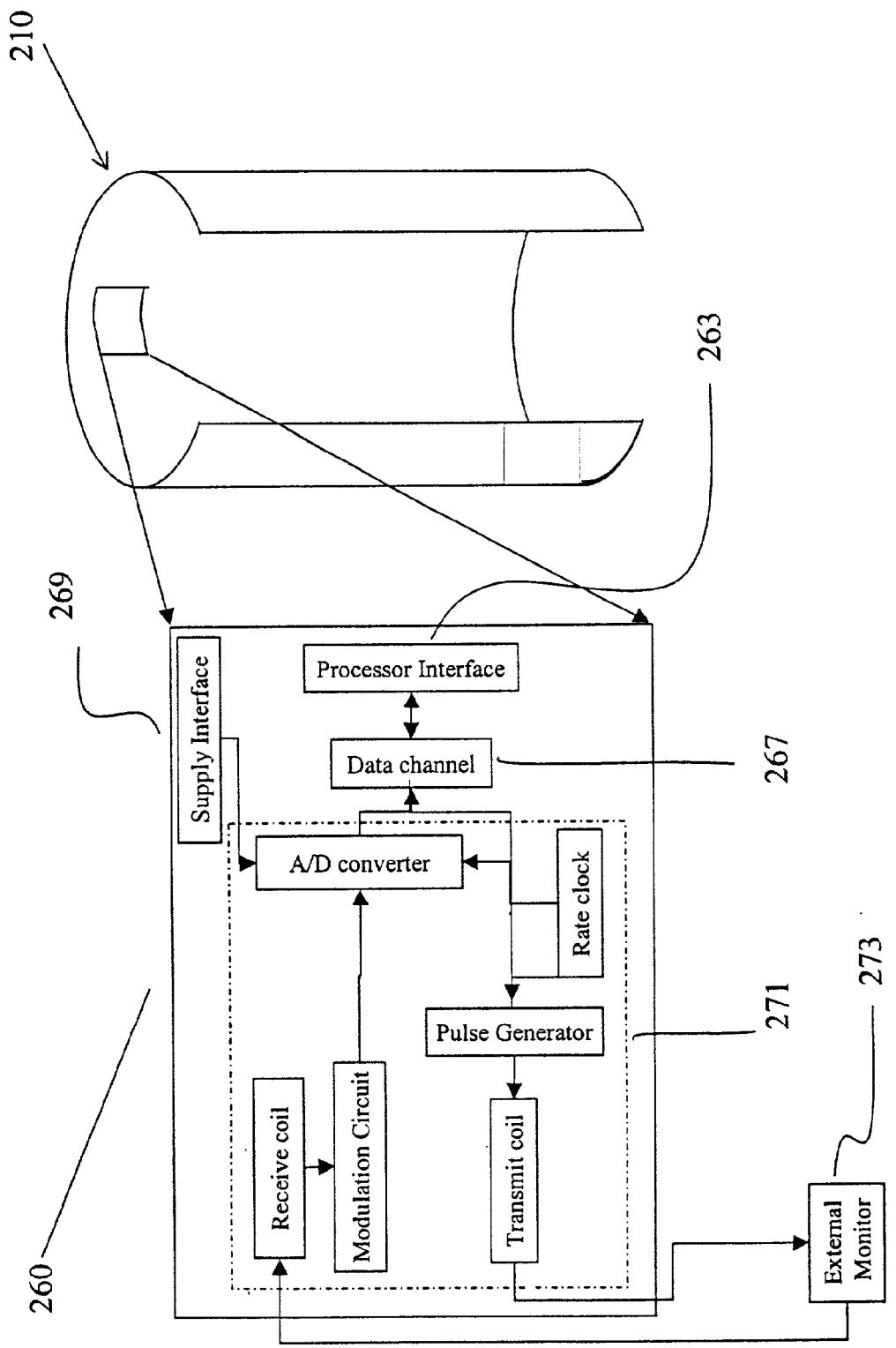
FIG. 9 is a partial exploded view of the particle analyzer sub-assembly of FIG. 4 illustrating a preferred telemetric device used therein.

FIG. 9 is a schematic of a preferred embodiment of a telemetry device 260 which, in the embodiment depicted, is affixed to the interior surface 226 of the particle analyzer 210 (see FIG. 4). In another embodiment, not shown, the telemetry device 260 is sealed within the outer casing 212 of particle analyzer 210, near the exterior surface of such particle analyzer 210.

Referring to FIG. 9, and in the preferred embodiment depicted therein, telemetry device 260 is in the form of an electronic circuit module which has a substantially rectangular cross-sectional shape. In one embodiment, the telemetry device 260 has a thickness of from about 0.01 to about 0.05 inches.

In the embodiment depicted, telemetry device 260 is comprised of a means for transmitting data from the telemetry interface 265 of processing/controlling device 264 (see FIG. 10) to the processor interface 263 (see FIG. 9) of telemetry device 260. In the embodiment depicted, input and output data are coordinated through a data channel 267. A power supply interface 269 transfers power from supply 261 (see FIG. 10) to one or more of the active devices within telemetry device 260.

Referring again to FIG. 9, it will be seen that various active devices are enclosed within the dotted line structure 271. It will be apparent to those skilled in the art how each such device functions and is powered.

By way of illustration and not limitation, one may use the device disclosed in U.S. Pat. No. 5,683,432 ("Adaptive, performance-optimizing communication system for communicating with an implanted medical device".). This patent claims a system comprising an implantable medical device and an associated device, each provided with a transmitter/receiver, wherein the system is further provided with means for optimizing communication between said implanted device and said associated device, said optimizing means comprising: means associated with said transmitter/receivers for defining a plurality of telemetry transmission types and for defining in conjunction with each of said telemetry types a prioritized set of a plurality of performance goals which vary depending upon telemetry transmission type; means associated with said transmitter/receivers for controllably altering a plurality of operational parameters of said transmitter/receivers; means associated with said transmitter/receivers for determining whether a transmission between said transmitter/receivers meets said performance goals; and means associated with said transmitter/receivers for selecting among said operational parameters and adjusting said selected operational parameters based upon said prioritized set of performance goals to achieve said performance goals in order of their priority. The entire disclosure of this United States patent is hereby incorporated by reference into this specification.

By way of further illustration, one may use the telemetry system disclosed in U.S. Pat. No. 5,342,408 "Telemetry system for an implantable cardiac device"), the entire disclosure of which is herby incorporated by reference into this specification. This patent claims a device in which " . . . said circuit means including data generating means for generating data indicative of said monitored activity or therapeutic activity in accordance with received command transmissions; and telemetry means for communicating with a non-implanted external receiver and transmitter, said telemetry means including receiving means for receiving said command transmissions from said non-implanted external transmitter, said command transmissions conforming to a first protocol and said command transmissions being selectively transmitted at two or more rates in accordance with said first protocol; and transmitting means for transmitting information including said data to said non-implanted external receiver in accordance with a second protocol, said information transmissions being selectively transmitted at one or more rates in accordance with said second protocol, said first protocol being different from said second protocol. The entire disclosure of this United States patent is hereby incorporated by reference into this specification.

By way of further illustration, one may use the telemetry receiver disclosed in U.S. Pat. No. 5,466,246 ("Telemetry receiver for implantable device, incorporating digital signal processing"), the entire disclosure of which is hereby incorporated by reference into this specification. This patent claims an "apparatus for receiving a modulated data signal transmitted from an implantable device, wherein the modulated data signal is modulated by a digital or an analog data signal in any of a plurality of distinct modulation modes, the apparatus comprising: front-end receiving means for receiving the modulated data signal from the implantable device, the front-end receiving means including means for amplifying and anti alias filtering the received signal; analog-to-digital converter means for sampling the amplified modulated data signal to produce a sequence of digitized samples; and digital signal processing means for filtering the sequence of digitized samples using at least one of a plurality of bandpass filters and for demodulating the filtered sequence of digitized samples using at least one of a plurality of demodulators, including an amplitude demodulator, a frequency demodulator, and a phase demodulator, to produce a demodulated data signal."

Referring again to FIG. 9, a signal from the transmit coil of telemetry device 260 is received by an external monitoring device 273. One may use any of the external monitoring devices known to those skilled in the art. Thus, by way of illustration and not limitation, one may use system disclosed in U.S. Pat. No. 6,167,312 ("Telemetry system for implantable medical devices"), the entire disclosure of which is hereby incorporated by reference into this specification. This patent claims: "An external device for use in communication with an implantable medical device, comprising: a device housing; a device controller, mounted within the device housing; a spatially diverse antenna array mounted to the device housing; an RF transceiver operating at defined frequency, located within the device housing, coupled to the antenna array; means for encoding signals to be transmitted to the implantable device, coupled to an input of the transceiver; means for decoding signals received from the implantable device, coupled to an output of the transceiver; and means for displaying demodulated signal received from the implanted device, mounted to the device housing; wherein the antenna array comprises a first antenna permanently mounted to the device housing and a second antenna removably mounted to the device housing and locatable at a distance from the housing and means for coupling the removable antenna to the RF transceiver while the removable antenna is located at a distance from the device housing; and wherein the device controller includes means for selecting which of the two antennas in the antenna array is coupled to the transceiver.

Other external receiving/monitoring means may also be used. FIG. 10 is a schematic of a controller 264 for communicating with the opto-electronic circuit arrays 326, 328, 330, and 332 (see FIG. 8). Referring to FIG. 10, the controller 264, in the embodiment depicted, is affixed to the interior surface 226 of the particle analyzer 210. In another embodiment, not shown, the controller 264 is sealed within the outer casing 212 of particle analyzer 210, near the exterior surface of such particle analyzer 210.

Referring to FIG. 10, and in the preferred embodiment depicted therein, controller 264 is in the form of an electronic circuit module which has a substantially rectangular cross-sectional shape. In one embodiment, the controller 264 has a thickness of from about 0.01 to about 0.05 inches.

In the embodiment depicted in FIG. 10, various active devices are illustrated within dotted line 275. As will be apparent to those skilled in the art, other combinations of active devices also may be used. Regardless of the particular combination used, the controller 264 contains means for receiving optical signals (see, e.g., waveguide interface 277), means for signaling to driver circuitry 320 (see, e.g., VCSEL Control Interface 279), means for converting one or more optical signals into one or more electrical signals (see, e.g., Optical Electronic conversion device 281), means for integrating electronic signals in a parallel fashion through a parallel interface (see, e.g., Parallel Interface 283), and means for controlling one or more lasers and for integrating various signals from the photodetectors (see, e.g., microprocessor 285).

Figure 11:
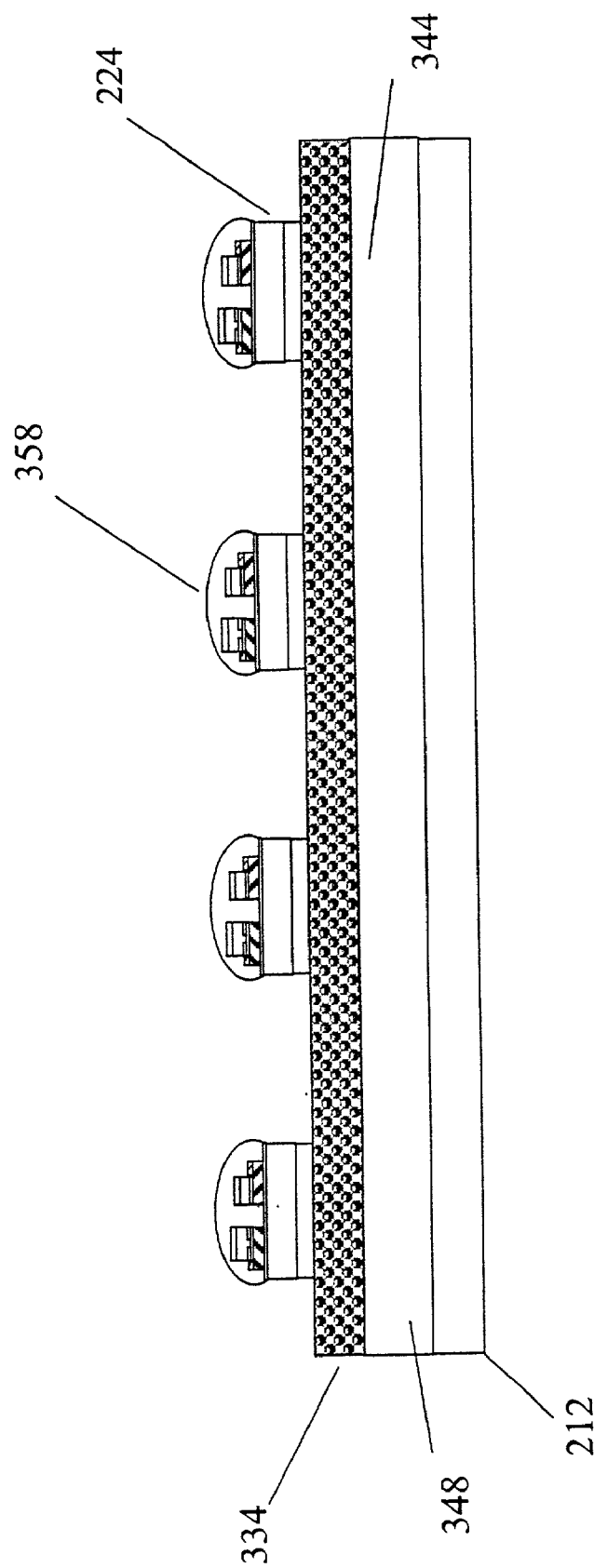
FIG. 11 is a schematic diagram of one preferred body of the particle analyzer sub-assembly, which comprises an opaque covering on a portion of the inner surface of the analyzer with additional underlying layers depicted.

Referring to FIG. 11, and in the preferred embodiment depicted therein, it will be seen that a transparent seal 358 is disposed over each optical assembly 224. One may use transparent sealing means known in the art. Thus, e.g., some of the materials which may be used, and means for using them to seal a device, are described in U.S. Pat. No. 5,556,421 ("implantable medical device with enclosed physiological parameter sensors or telemetry link"), the entire disclosure of which is hereby incorporated by reference into this specification. In the embodiment depicted in FIG. 11, the thickness of the transparent layer 358 is increased for illustration purposes only and layers are not drawn to scale. The actual thickness of the transparent layer 358 preferably has a transmissivity for electromagnetic energy as required by the particular sensor or communication mechanism employed in the implantable particle analyzer 210 (see FIG. 4). The transparent layer 358 preferably is constructed of a suitable material that conducts electromagnetic energy without excessive absorption or reflection, thereby allowing the embedded opto-electronic circuit arrays 326 et seq. to transmit and receive electromagnetic energy to and from a point external to the transparent layer 358. For many applications, the transparent layer 358 preferably is made of an epoxy resin or similar thermosetting polymer material which is formed in situ. In addition to epoxy, other material suitable for layer 358 include glass, plastics and elastomers (such as Dow Chemical's Pellethane) and ceramic materials (such as sapphire).

Figure 12:
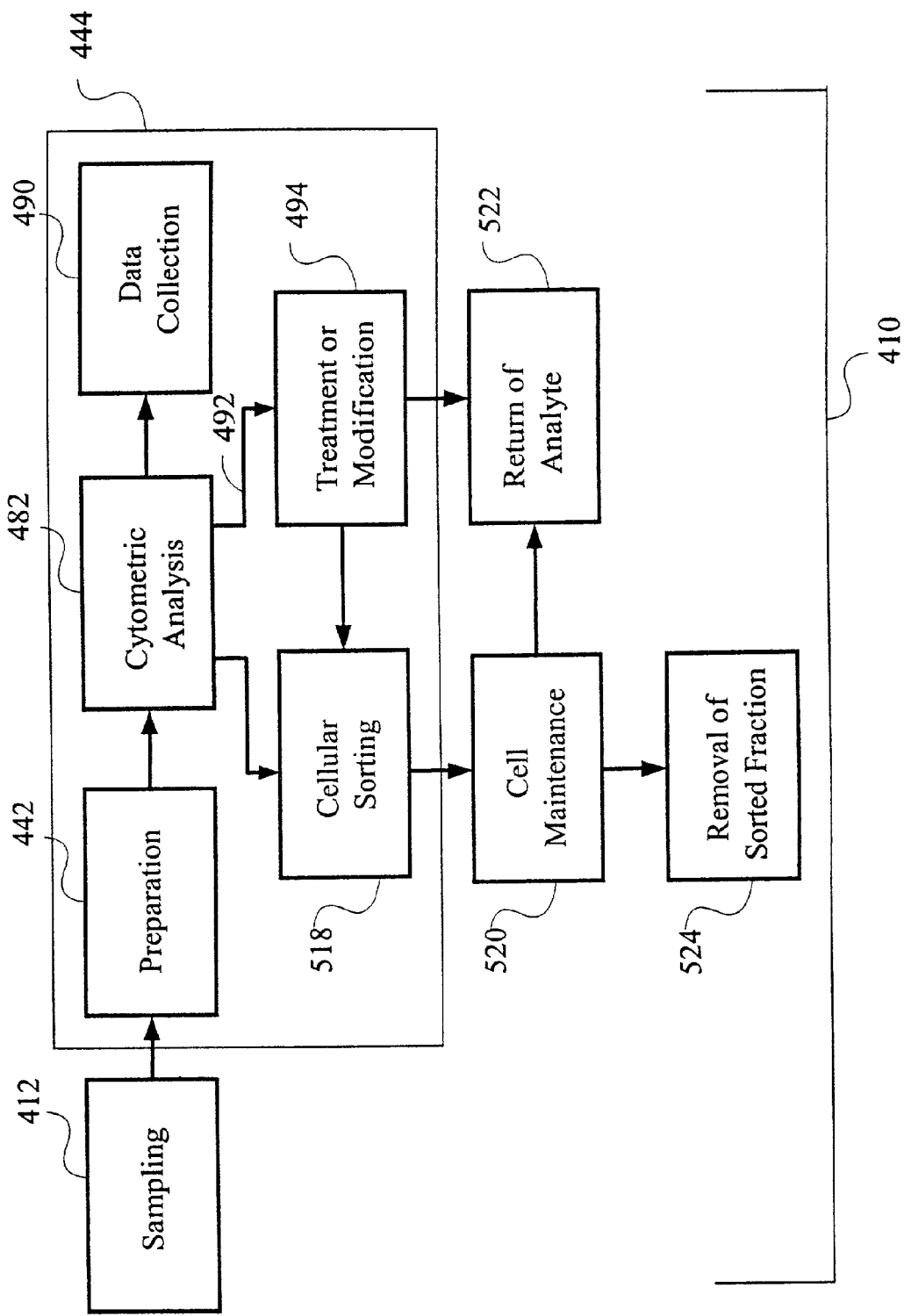
FIG. 12 is a flow diagram of one preferred process of the invention.

FIG. 12 is a flow diagram of one preferred process 410 for analyzing, treating, and maintaining certain bodily fluids. In step 412 of the process, the bodily fluids are sampled.

One may use any conventional means for sampling the body fluids. The body fluids which are typically sampled include, e.g., blood, lymph, spinal fluid, bone marrow, and the like.

In one embodiment, the body fluids are sampled by means of the sampling system descilbed in U.S. Pat. No. 6,159,164, the entire disclosure of which is hereby incorporated by reference into this specification. The system of this patent samples a body fluid through a tube attached to a patient's body; and the system is operable by a user having a hand, including a palm, a thumb, and at least a first finger and a second finger. The system comprises a fluid sampling site connected to the tube; means for receiving the tube; means for forming a chamber; means for selectively increasing the size of the chamber to a maximum volume and for decreasing the size of the chamber to a minimum volume, the means for increasing and decreasing the size of the chamber being operable by moving the first and second fingers or the thumb in a flexion movement toward the palm to achieve the maximum volume of the chamber, the means for increasing and decreasing the size of the chamber also being operable by moving the first and second fingers or the thumb in a flexion movement toward the palm to achieve the minimum volume of the chamber such that the same motion of the user's first and second fingers can selectively accomplish the maximum volume to aspirate fluid from the patient's body to the fluid sampling site or accomplish the minimum volume to expel the fluid into the patient's body.

Figure 13:
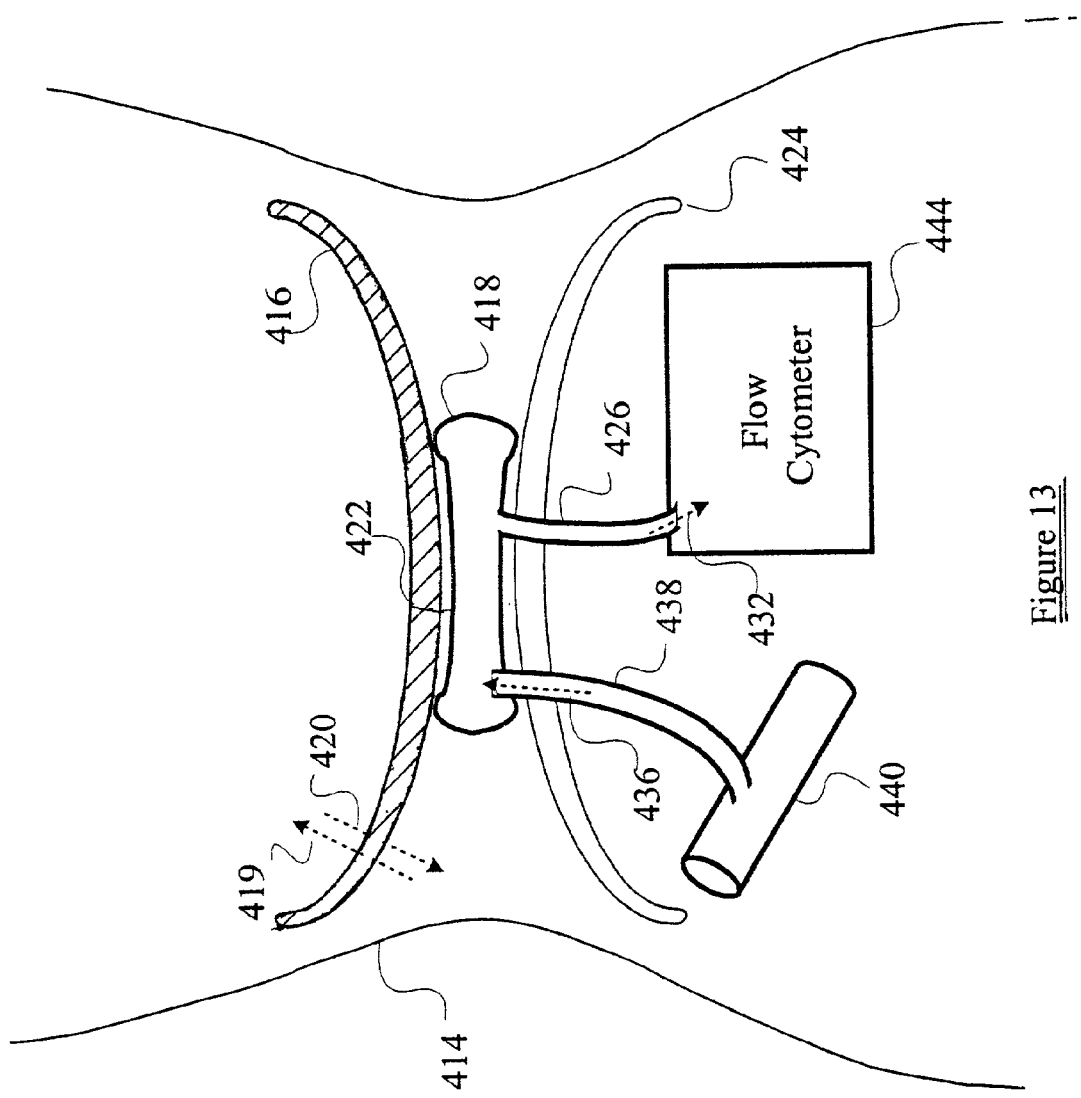
FIG. 13 is a schematic of one preferred sub-assembly of the invention, wherein the sub-assembly is comprised of a cell-sorter.

FIG. 13 indicates another sampling assembly, which may be used. Referring to FIG. 13, a female patient 414 has disposed within her body, beneath her diaphragm 416, a pump 418, which is actuated by the movement of diaphragm 416 in the direction of arrows 419 and 420.

The pump 418 has a deformable and elastic casing 422. When casing 422 is compressed between diaphragm 416 and abdominal wall 424, its interior volume will decrease, and fluid disposed within pump 418 will be discharged through line 426 to flow cytometer sub-assembly 444.

Figure 14C:
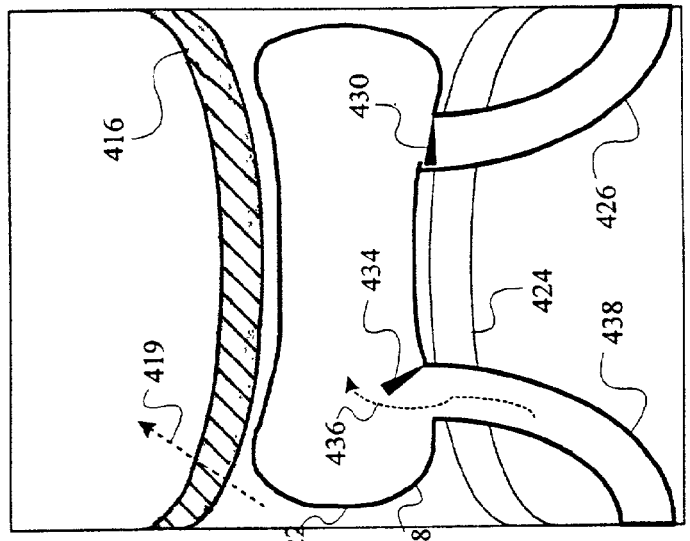
FIGS. 14A, 14B, and 14C schematically illustrate the actions of the pump of the sub-assembly depicted in FIG. 13.
Figure 14B:
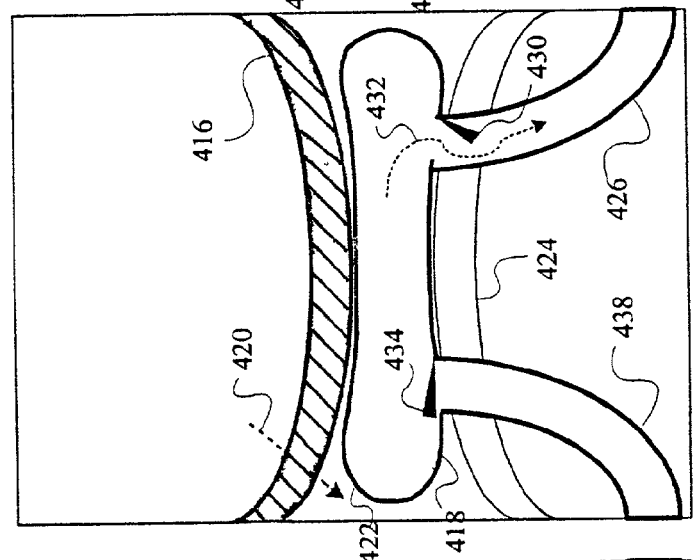
Figure 14A:
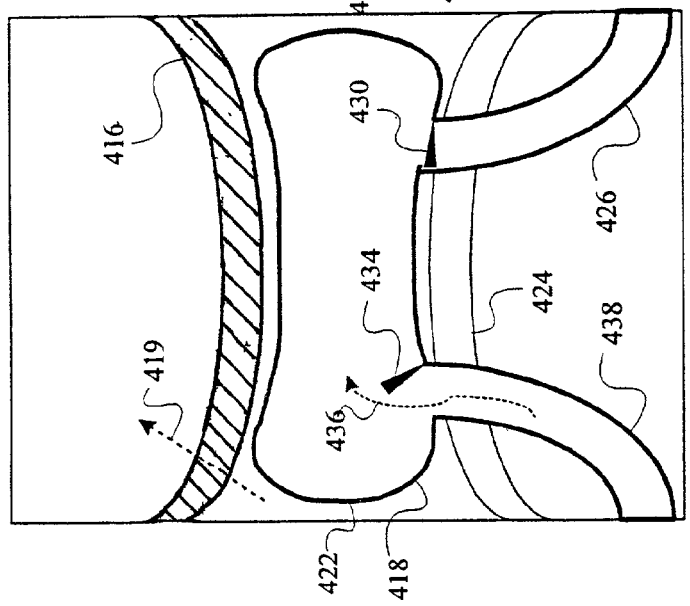

Referring now to FIGS. 13 and 14, the pump 418 comprises one way flow valve 430 (see FIGS. 14a–c), which allows flow in-the only in the direction of arrow 432; and it also comprises one way flow valve 434 (see FIGS. 14a–c), which allows flow only in the direction of arrow 436. Thus, when casing 422 is compressed, fluid may flow only through line 426; when the compressed casing 422 is allowed to expand to its original shape (when the diaphragm 416 relaxes), the fluid may flow only through line 438.

In one embodiment, the casing 422 is made from a flexible, elastic biocompatible material.

Although the pump 418 is shown disposed beneath the patient's diaphragm 416, it will be apparent that such pump 418 may be disposed beneath or nearby other parts of a body which expand and contract. Thus, by way of illustration and not limitation, the pump 418 may be positioned between lung and the ribcage, between muscle and bone, between a heart and a sternum, and the like.

Referring again to FIG. 13, it will be apparent that, every time the diaphragm 416 expands and thereafter contracts, fluid will be withdrawn from blood vessel via line 438 into pump 418; and the fluid within such pump 418 will be fed to the flow cytometer sub-assembly 444 via line 426 upon the next expansion of the diaphragm 416. This is one preferred means of sampling the blood in blood vessel 440, and it operates continuously with the movement of diaphragm 416.

FIGS. 14A, 14B, and 14C illustrate the operation of pump 418 in its intake phase (FIG. 14A), its expulsion phase (FIG. 14B), and its subsequent intake phase (FIG. 14C). The pump 418 is compressed when the diaphragm 416 moves in the direction of arrow 420; and it is allowed to return to its non-compressed state when the diaphragm 416 moves in the direction of arrow 419.

In another embodiment, not shown, the pump 418 is replaced by a piezoelectric assembly (not shown) which, upon pressure being applied to it, produces a difference of potential sufficient to actuate a pump to which it is electrically connected.

Referring again to FIG. 12, in step 442 of the process, the bodily fluid, which has been sampled, is then prepared for analysis. One may use any method for enumerating and distinguishing between fluid cell populations in a bodily sample. Thus, by way of illustration and not limitation, one may use the method described in U.S. Pat. No. 6,197,593, the entire disclosure of which is hereby incorporated by reference into this specification.

Figure 19:
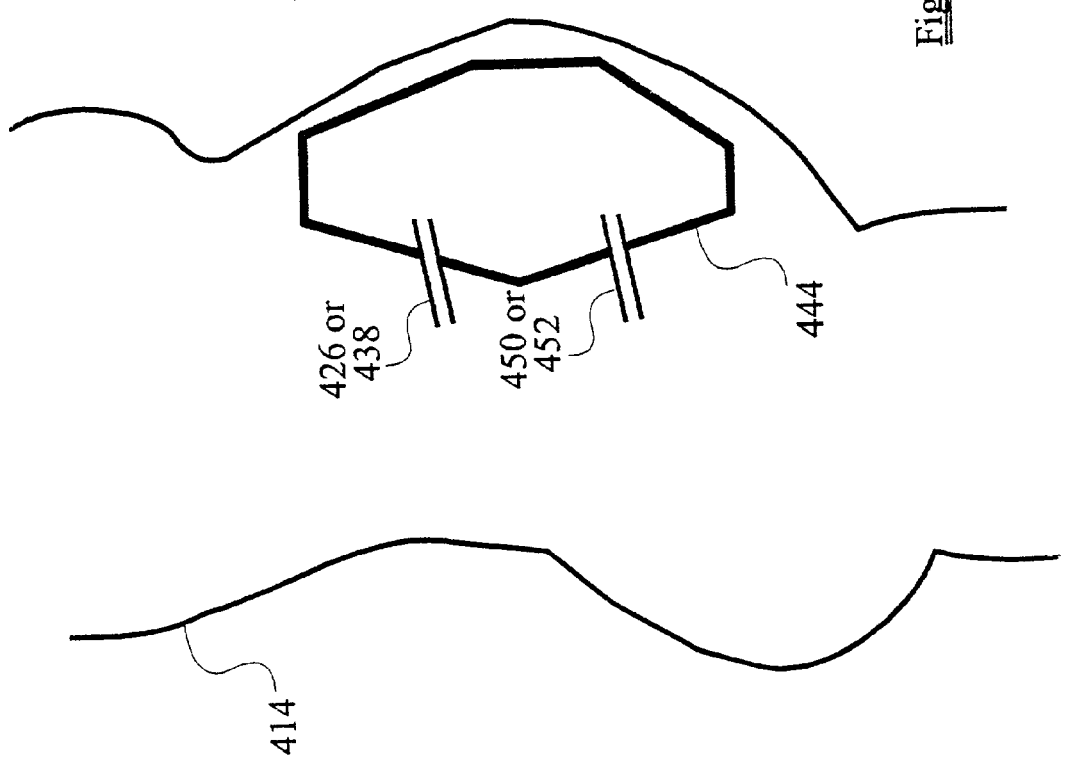
FIG. 19 is a schematic of the assembly in FIG. 1 disposed within a living body.

In the first step of the process of U.S. Pat. No. 6,197,593, a biological sample is contacted with two or more blood cell populations with a selective nucleic acid specific blocking agent to form a sample mixture. The sample mixture is then contacted with a cell membrane permeable, red-excited dye without significantly disrupting cellular integrity of the cells to form a dyed sample mixture. The dyed sample mixture is excited with light in a single red wavelength; and, thereafter, fluorescence emitted from different cell populations in the dyed sample mixture are measured, wherein the fluorescence emitted from one blood cell population is distinguishable from the fluorescence emitted from another blood cell population. Alternatively, or additionally, one may prepare the sampled fluid by the process depicted in FIG. 15. Referring to FIG. 19, it will be seen that a flow cytometer sub-assembly 444 is disposed in a patient's body 414. In the embodiment depicted in FIG. 191 the flow cytometer sub-assembly 444 is disposed beneath a patient's skin.

Figure 20:
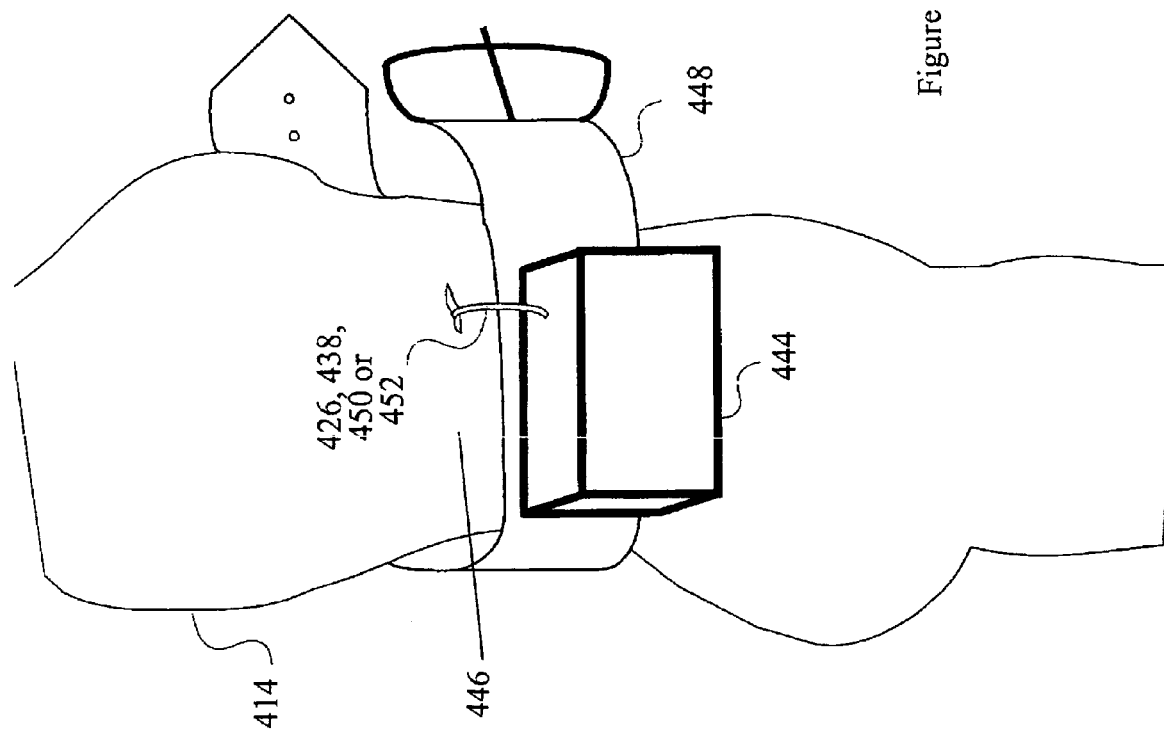
FIG. 20 is a schematic of the assembly in FIG. 1 disposed outside of a living body

The flow cytometer sub-assembly 444 may be disposed either within or without the patient's body. Thus, as is illustrated in FIG. 20, a flow cytometer sub-assembly 444 is disposed on top of skin 446 rather than underneath it. In this embodiment, cytometer sub-assembly 444 may be temporarily attached to skin 446 by conventional means such as, e.g., belt 448 extending around the torso (not shown) of the patient.

Figure 17:
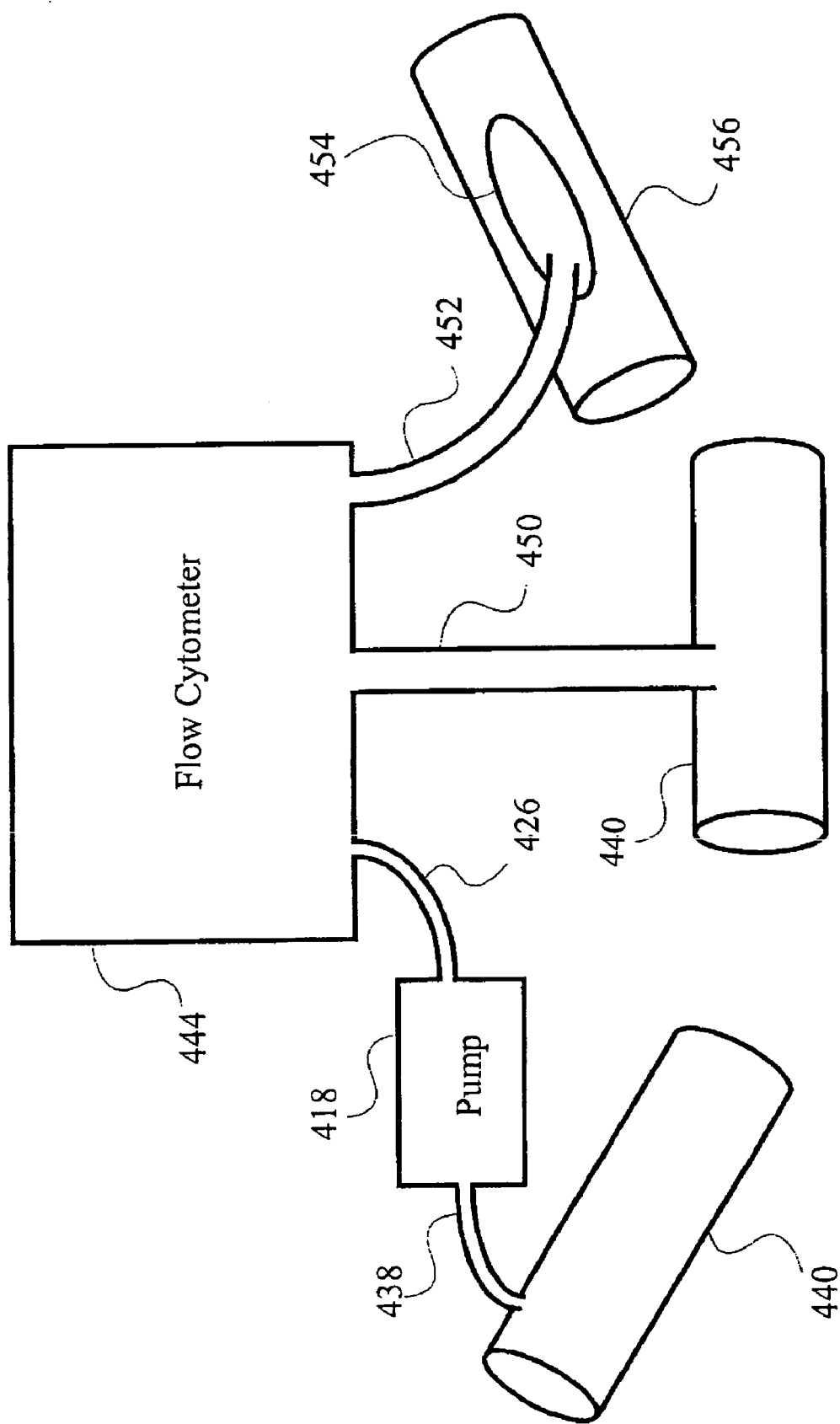
FIG. 17 is a schematic of one preferred means for maintaining a viable bodily fluid.
Figure 18:
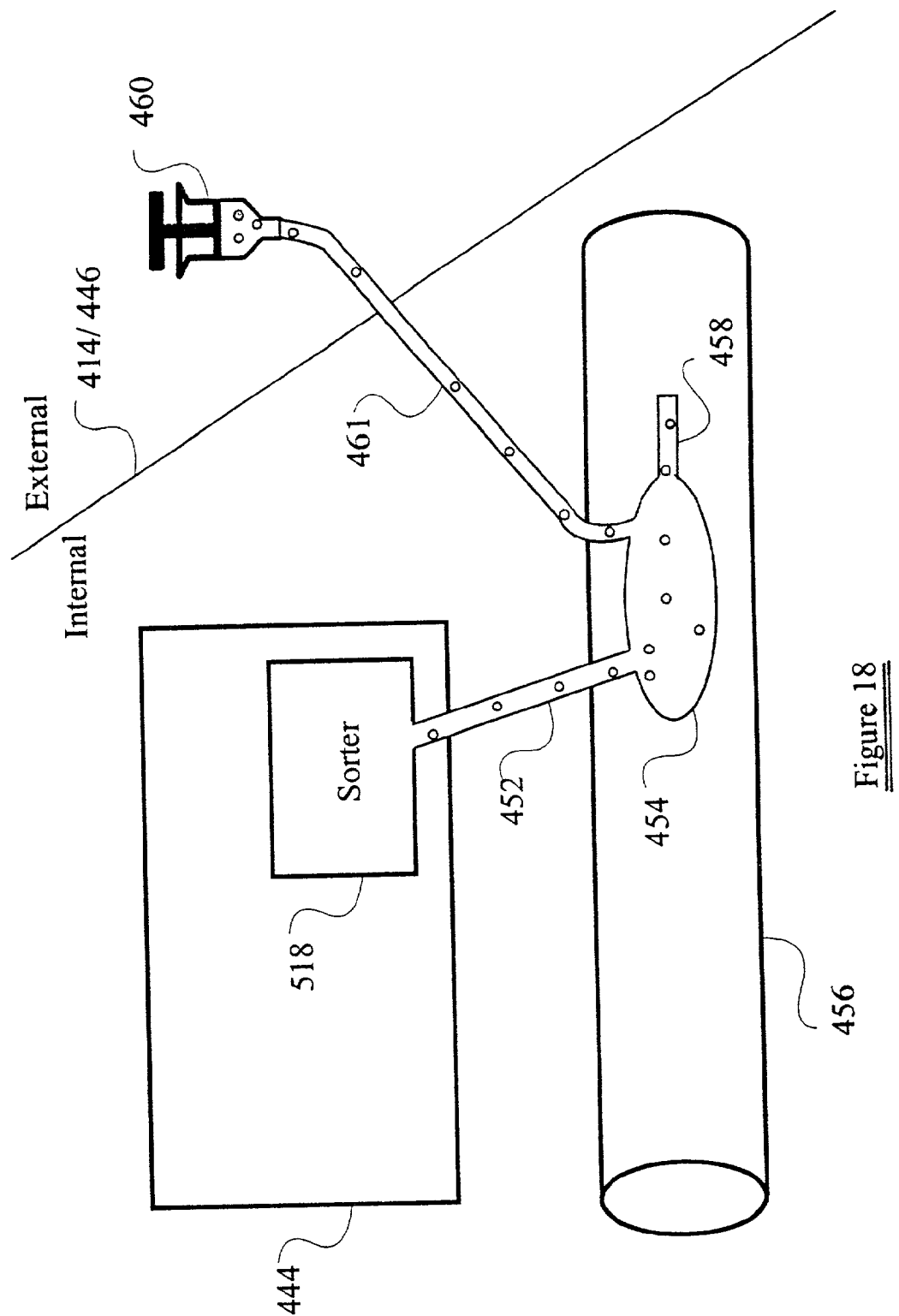
FIG. 18 is a schematic of another embodiment similar to those depicted in FIG. 17;17

In one preferred embodiment depicted in FIG. 17, bodily fluids, which have been analyzed by cytometer sub-assembly 444 may be fed via line 450 to blood vessel 440. Alternatively, or additionally, such analyzed bodily fluids may be ted via line 452 to reservoir 454, which in the embodiment depicted in FIGS. 17 and 18, is disposed in a blood vessel 456. One may withdraw fluid from reservoir 454 into blood vessel 456 by means of line 458. Alternatively, and referring to FIG. 18, one may withdraw fluid from reservoir 454 outside of the body by conventional means, such as syringe 460 attached to a catheter line 461. In either case, when the analyzed and/or treated fluid is within the reservoir 454, it is supplied with essential supplies for its survival. Thus, e.g., reservoir 454 may be surrounded by a membrane which facilitates the entry of essential supplies, such as glucose and oxygen. The membrane also allows the transfer of waste materials from it, such as lactate and carbon dioxide.

FIG. 17 is a schematic diagram of the flow cytometer sub-assembly 444 implanted within a patient's body. The flow cytometer sub-assembly 444 may be implanted within the patient's body by conventional means. Thus, by way of illustration and not limitation, one may implant the flow cytometer sub-assembly 444 by the method disclosed in U.S. Pat. No. 6,198,950, the entire disclosure of which is hereby incorporated by reference into this specification. In the process of such patent, the implantable device is implanted under the skin in such a manner that the cannula projects into a blood vessel.

Thus, by way of further illustration, one may use the implantation processes and/or techniques disclosed in U.S. Pat. Nos. 6,198,969, 6,198,971, 6,198,965, 6,198,952, and the like. The entire disclosure of each of these United States patents also is incorporated by reference into this specification.

Figure 15:
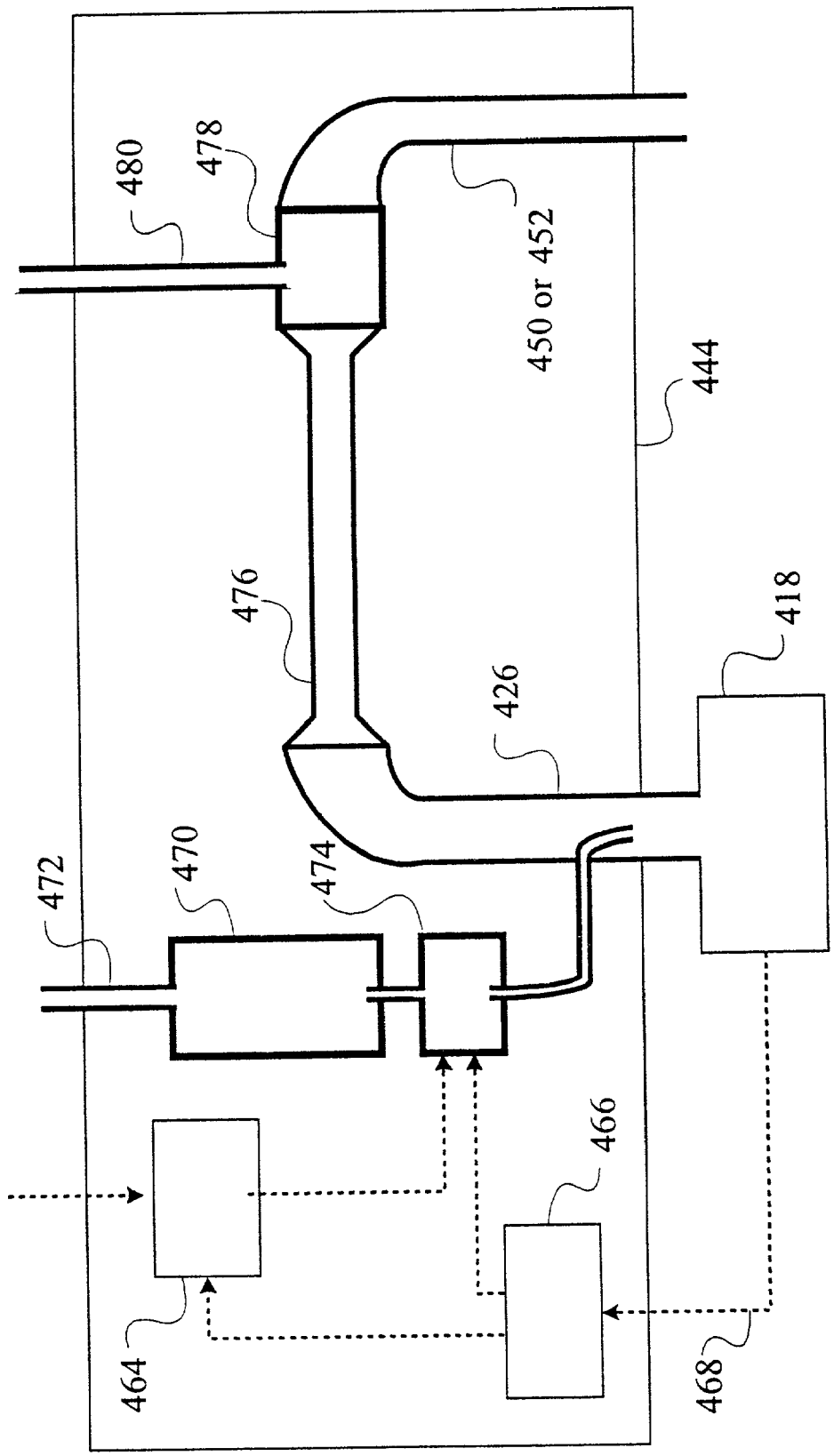
FIG. 15 is a schematic of the detection/treatment system of the cell sorter sub-assembly.

In the preferred embodiment depicted in FIG. 15, lines 426 and 450/452 are preferably cannulae. A controller 464 operatively connected to a power source 466 controls the administration of dye into the bodily fluid.

In one embodiment, depicted in FIG. 15, pump 418 provides input to power source 466. Thus, every output cycle of pump 418 provides some hydraulic pressure via line 468 to power source 466. This hydraulic pressure is converted into electrical power by conventional means such as, e.g., piezoelectric means.

In another embodiment, power source 466 is a battery. The battery may be rechargeable. Thus, in one aspect of this embodiment, the battery is recharged by electromagnetic radiation. The electromagnetic radiation may be transferred from a source disposed within the patient☐s body; or it may be transferred from a source external to the patient's body. Thus, e.g., an magnetic field may be produced by passing alternating current through a wire or coil, and this alternating magnetic field may be transmitted through a patient's skin into his body and coupled with an transducer, which produces alternating current from the alternating magnetic field.

In another embodiment, not shown, material and/or energy is fed to power source 466 via a line (not shown), and this material and/or energy is adapted to furnish power to power source 466. Thus, e.g., the material charged to power source 466 may undergo and/or facilitate a reaction which produces energy consumed by power source 466.

Referring again to FIG. 15, the appropriate dye(s) or other markers are fed to dye reservoir 470 by line 472 and, in response to one or more signals from controller 464, feeds such dye(s) into injector 474 and thence into line 426, where the dye(s) mix with the fluid disposed within such line 426 and selectively mark them. The selectively marked bodily fluid(s) are then funneled into the flow chamber 476 of the cytometer sub-assembly 444, wherein they are subjected to analysis by conventional optical means.

After the marked bodily fluid has been analyzed and, optionally, treated, and prior to the time it is returned via line 450 or 452 to either the body or to a reservoir, the marker (dye) may be removed from the fluid by conventional means. Thus, by way of illustration and not limitation, the marker may be removed by means of an adsorption column 478 and/or by other adsorption means. Thus, e.g., the dye may be removed by other means, including chemical means. By way of illustration and not limitation, Processes for stripping dyes from or decolorizing various materials are known in the art. For example, U.S. Pat. No. 4,227,881 discloses a process for stripping dyes from textile fabric which includes heating an aqueous solution of an ammonium salt, a sulfite salt and an organic sulfonate to at least 140.degree. F. (60.degree. C.) and adding the dyed fabric to the heated solution while maintaining the temperature of the solution. U.S. Pat. No. 4,783,193 discloses a process for stripping color from synthetic polymer products by contacting the colored polymer with a chemical system.

It will be apparent that one can use one of several different physical and/or chemical means of removing the dye/marker from the bodily fluid; the aforementioned description is illustrative and not limitative. Regardless of which means are used, a purified bodily fluid is returned via line 450/452 to either the body or a reservoir.

During the purification process, additional material needed for such process may be charged via line 480, and/or dye and/or other waste material may be removed via line 480.

Referring again to FIG. 15, the dye reservoir 470 may contain one or more markers, and/or it may contain diluent to preferably dilute the bodily fluids so that preferably only one cell passes by any particular point in flow chamber 476 at any one time. As will be apparent, this laminar flow condition facilitates the analyses of the bodily fluid by optical means.

Referring again to FIG. 12, in step 482 of the process the marked bodily fluid is analyzed. One may conduct, e.g., flow cytometric analyses in accordance with the procedures described in the patents listed elsewhere in this specification; and one may use the devices disclosed in such patents for such analyses.

Figure 16:
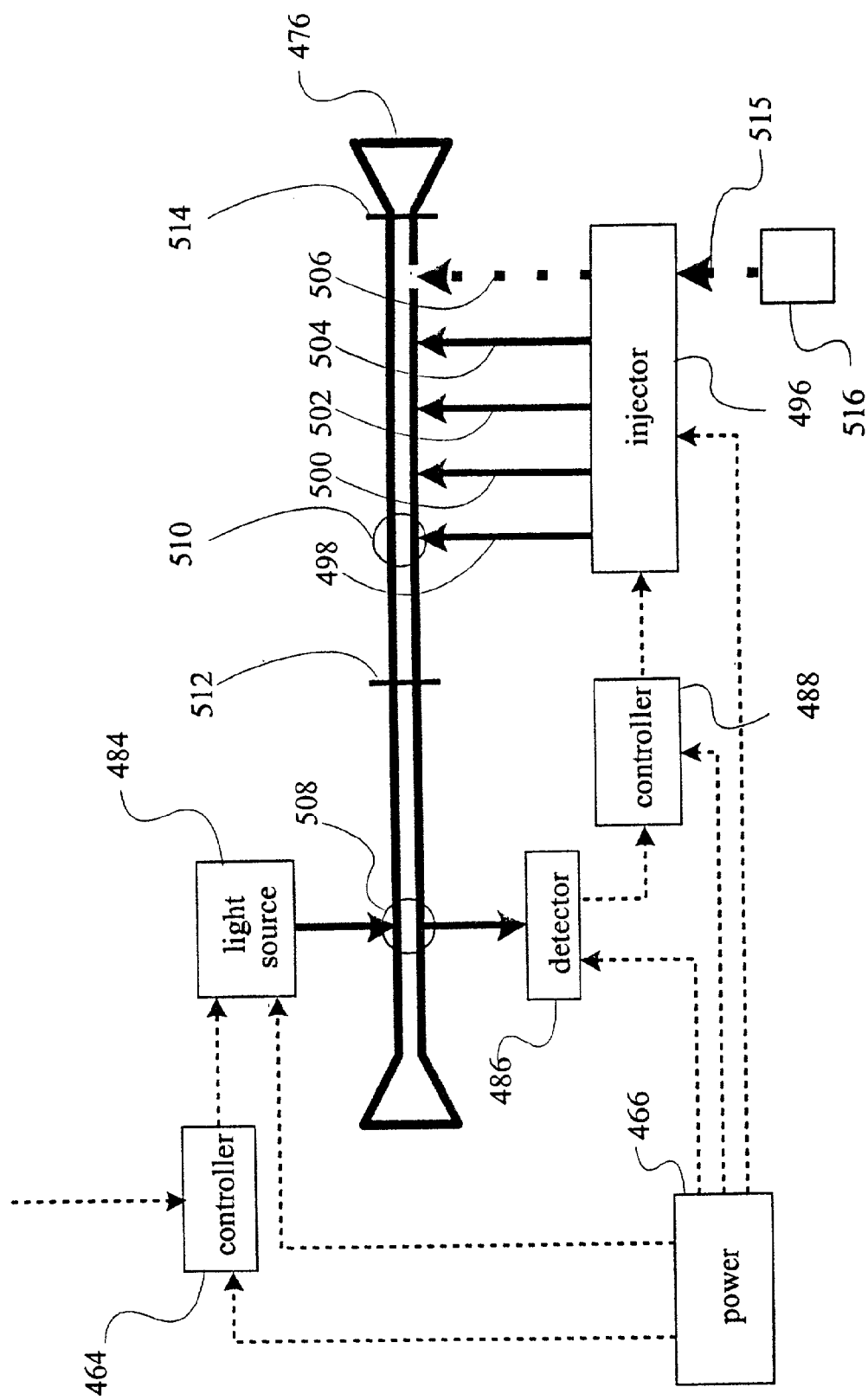
FIG. 16 is a schematic of the assembly of FIG. 1 in relation to the location of bodily fluids.

One such analytical device is illustrated schematically in FIG. 16. For the sake of simplicity of representation, unnecessary detail has been omitted from FIG. 16, Referring to FIG. 16, and in the embodiment depicted therein, a light source 484 is caused to focus on flow chamber 476. The amount of light transmitted through flow chamber 476 will vary with the properties of the bodily fluid within such chamber; see, e.g., U.S. Pat. Nos. 6,197,756, 6,197,593, 6,197,583, 6,197,582, 6,197,568, 6,197,540, and the like. The entire disclosure of each of these United States patents is hereby incorporated by reference into this specification.

The light transmitted through flow chamber 476 is detected by detector 486 which may, e.g., be a photodetector. Data is fed from detector 486 to controller 488.

Controller 488 is equipped with a database indicating the properties of normal bodily fluids. The property of any particular bodily fluid being analyzed can be compared with this database to determine whether they correlate. A lack of correlation may indicate a disease state, which can be thereafter treated by the flow cytometer sub-assembly 444 (see FIGS. 13 and 17).

Referring again to FIG. 12, in step 490 data is collected from the analysis conducted in controller 488 in FIG. 16. Historical data may also be fed to the data collection device, either before, during, or after the analysis 482 of the bodily fluid. The collection of data in step 490, and its use, may be done in accordance with U.S. Pat. No. 6,197,593, the entire disclosure of which is hereby incorporated by reference into this specification.

Data from data collection step 490 may be added to from external sources. Alternatively, data from data collection step 490 may be exported to one or more external devices.

In one embodiment, not shown, when analysis step 482 and data collection step 490 indicate the presence of a dangerous abnormal condition within the bodily fluid, an external alarm is activated to warn the patient.

When analysis 482 of the bodily fluid indicates that it is abnormal, the bodily fluid may be charged via line 492 to treatment step 494. As is indicated in FIG. 16, this treatment step 494 may occur in line within the flow chamber 476.

Referring again to FIG. 16, injector 496 is operatively connected to both detector 486 and controller 488 and, in response to signals there-from, feeds energy and/or material to the bodily fluid to treat it.

One may feed radiation 498 to the bodily fluid to treat it. Thus, e.g., one may cause ultraviolet radiation to impact flow chamber 476 and to kill cancerous cell(s) disposed within such flow chamber 476. Thus, e.g., one may use electrical discharge 500 by means such as, e.g., electroporation. Thus, e.g., one may use magnetic fields 502. Thus, e.g., one may use sound particles and rays 504. Alternatively, or additionally, one may feed material via line 506 into flow chamber 476, which is adapted to kill or modify the abnormal cell(s).

One may use any of the materials commonly used to kill or modify cells. Thus, by way of illustration and not limitation, one may use gene vectors, viral particles, antibodies, chemotherapeutic agents, etc. Thus, e.g., one may do selective gene therapy on any particular cell.

To the extent, if any, there is a need to replenish material within injector 496, such material may be fed to injector 496 via line 515 from reservoir 516.

When it is desired to cause a particular cell to remain at a particular location for any period of time, the controller 464 can cause the close valves 512 and 514 so that fluid disposed between such valves cannot flow.

Because the flow cytometer sub-assembly 444 (see FIGS. 13, 15, and 17) is capable of detecting one cell at a time, any abnormal cell detected at point 508 may be treated at point 510, e.g., the controller 488 determining precisely where such particular cell is at any point in time.

Referring again to FIG. 12, if the cells analyzed in step 482 are normal, they may be sorted in sorting step 518. In this sorting step, one may selectively segregate and collect certain cells within the bodily fluid. One may use conventional flow cytometer sorters in this step; see, e.g., U.S. Pat. Nos. 5,985,216 and 5,998,212, the entire disclosure of each of which is hereby incorporated by reference into this specification.

In one embodiment, stem cells are sorted from the bodily fluid. The identification and separation of such stem cells may be conducted by conventional means such as, e.g., the means disclosed in U.S. Pat. No. 5,665,557, the entire disclosure of which is hereby incorporated by reference into this specification. In the process of this patent, for epitope mapping studies, quintuplicate aliquots of KG1a cells (0.5–1.times.10.sup.6/analysis) were incubated on ice with either 5 μl 8A3, 7D1, 7C5 or 8A1. 2 μl biotinylated conjugates of 8A3, 7D1, 7C5 or 8A1 were then added to each of the 4 sets of the above samples (i.e. 16 samples total for this experiment) for a further 30 min on ice. Cells were then washed twice in cold phosphate buffered saline by centrifugation and incubated with cytochrome-conjugated streptavidin for a final 30 min on ice. Stained cells were then analyzed by flow cytometry using a FACScan (Becton Dickinson Instrument Systems (BDIS).

The stem cells sorted in step 518 may be collected and thereafter used for many different purposes.

Referring again to FIG. 12, means for maintaining bodily fluid (and/or a portion thereof) is maintained in step 520. Referring to FIG. 18, some or all of the cells which have been sorted in step 518 of FIG. 12 may be passed via line 452 to reservoir 454. In one embodiment, not shown, sorting step 518 is bypassed and bodily fluid is directly passed into reservoir 454.

In the embodiment depicted in FIG. 17, reservoir 454 is disposed within blood vessel 456. In another embodiment, not shown, reservoir 454 may be disposed adjacent to a blood vessel, and/or be disposed adjacent to the intestines.

As is illustrated in FIG. 12, the cells or bodily fluid treated in step 494 may be returned to the body in step 522; see, e.g., line 450 of FIG. 17, which facilitates the return of such material to blood vessel 440. Alternatively, after the bodily fluid(s) or portion(s) thereof are treated in step 494, they may thereafter be sorted in step 518, maintained in step 520, and thereafter returned in step 522 via line 458 (see, e.g., FIG. 18).

Instead of returning some or all of the material being maintained in step 520, one may remove some or all of such material in step 522 by means, e.g., of syringe 460 and line 461; see, e.g., FIG. 18.

The flow cytometer sub-assembly 444 preferably has a weight of less than 6 pounds and, more preferably, weighs less than about 3 pounds. In one embodiment, the flow cytometer sub-assembly 444 is made from miniaturized components and weighs less than about 2 pounds.

Figure 21:
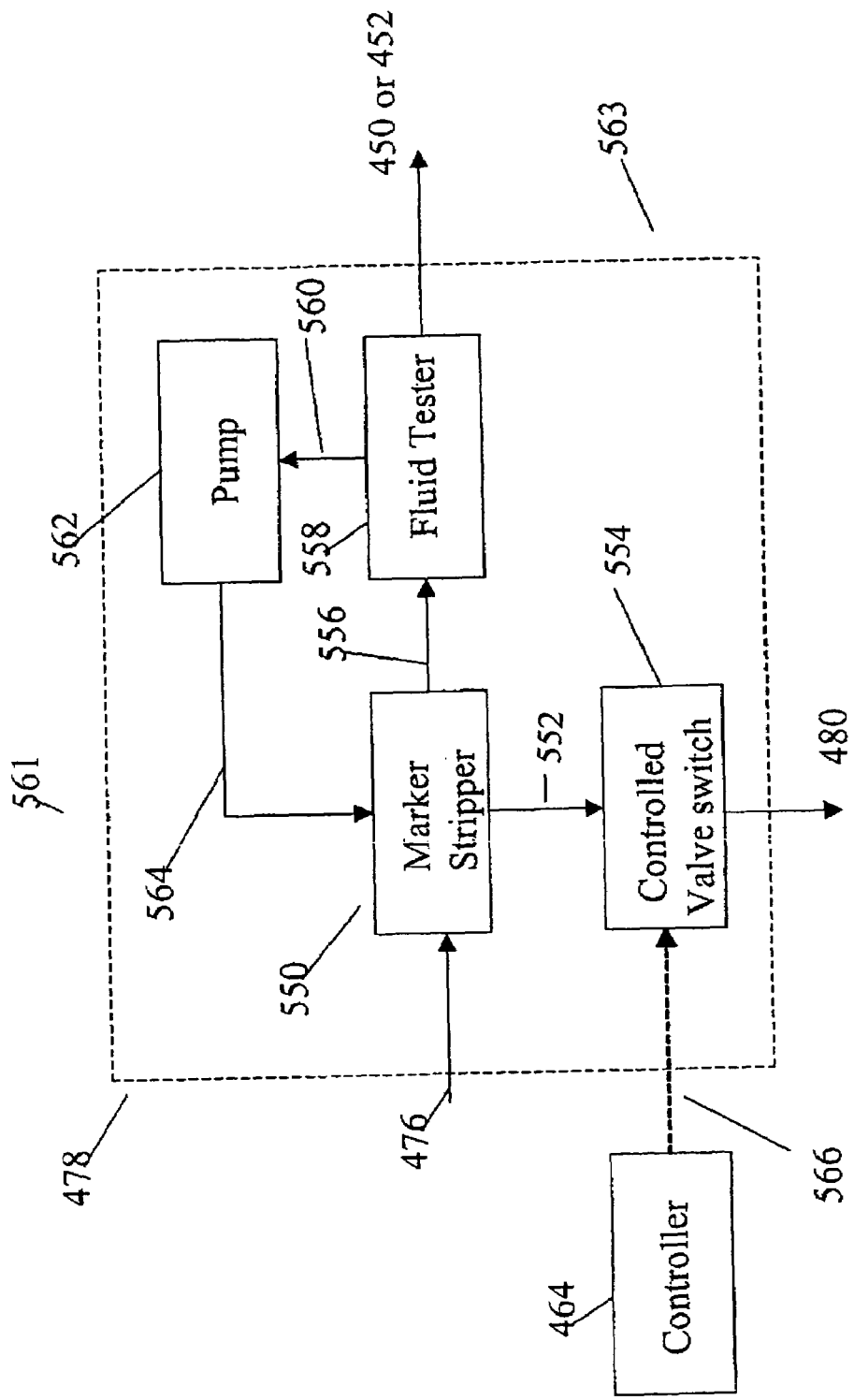
FIG. 21 is a block diagram of another preferred process of this invention.

FIG. 21 is a block diagram of a preferred process 561 which utilizes adsorption column 478 (see FIG. 15). In the first step of this process, the output of flow cytometer sub-assembly 444 is fed through flow chamber 476 (see FIG. 15) to marker/stripper 550, wherein the marker is removed from the cellular material flowing through flow chamber 476. As will be apparent, the marker had first been affixed to such cellular material with injector 474 (see FIG. 15); this marker is discussed elsewhere in this specification.

Referring again to FIG. 21, and in an additional embodiment of the flow cytometer or particle analyzer sub-assembly, a bodily fluid (not shown) is flowing in through flow chamber 476. In one embodiment, the bodily fluid is blood, and it is caused to flow by the action of a heart. In another embodiment, the bodily fluid may be a non-hematologic fluid such as, e.g., lymph, urine, cerebrospinal fluid, and the like. In another embodiment, the bodily fluid is comprised of red blood cells and/or leukocytes and/or neutrophils and/or other cells or cellular material. Each of these components will have a different optical response to a specified optical input.

The cells of the bodily fluid preferably have either endogenous optical properties, and/or they are labeled to provide optical properties. Thus, e.g., the cells may be labeled with flourescently-conjugated antibodies. Thus, e.g., in one embodiment the flow cytometer or particle analyzer sub-assembly will utilize either injected fluorescent contrast or emitted light energies intrinsic to specific cells themselves. As is known to those skilled in the art, antibodies may be conjugated with polymeric dyes with fluorescent emission moieties such as aminostyryl pyridinium (see, e.g., U.S. Pat. No. 5,994,143, the entire disclosure of which is hereby incorporated by reference into this specification).

Referring again to FIG. 21, and in the preferred embodiment depicted therein, the markers or markers are removed from the bodily fluid in marker/stripper 550. One may use conventional means from removing the marker(s) from the bodily fluid. Thus, by way of illustration and not limitation, the marker may be removed by means of an adsorption column 478 and/or by other adsorption means. Thus, e.g., the dye may be removed by other means, including chemical means. By way of illustration and not limitation, processes for stripping dyes or decolorizing various materials are known in the art. For example, U.S. Pat. No. 4,227,881 discloses a process for stripping dyes from textile fabric which includes heating an aqueous solution of an ammonium salt, a sulfite salt and an organic sulfonate to at least 140 degree F. (60 degree C.) and adding the dyed fabric to the heated solution while maintaining the temperature of the solution. U.S. Pat. No. 4,783,193 discloses a process for stripping color from synthetic polymer products by contacting the colored polymer with a chemical system.

In one embodiment, dye separators are used in maker/stripper 550, and these dye separators may require additional plasma fluid which may be obtained from a plasma reservoir (not shown) which is connected to the dye separators.

After the marker/stripper has removed the marker(s) or otherwise rendered the fluid harmless, the removed marker(s)/dye(s) are fed via line 552 to a controlled switch valve 554, which can feed the marker(s)/dye(s) to one or more different locations, depending upon the nature of the marker(s)/dye(s).

Thus, e.g., in one embodiment, the dyes are fed via line 480 to dye reservoir 470 (see FIG. 15). Thus, e.g., in another embodiment (not shown), the dye(s)/marker(s) waste material is fed to another reservoir/holding tank (not shown), to be disposed of. In another embodiment, not shown, the dye(s)/marker(s) may be fed to the patient's bladder and/or gastrointestinal tract, depending upon the toxicity and/or degradability of the dye(s)/marker(s). The controller 464, which includes one or more suitable sensors (see FIG. 15), controls to which destination(s) the dye(s)/marker(s) are to be sent.

Referring again to FIG. 21, the purified body fluid is fed via line 556 to a fluid tester 558, which determines the degree of purity of the body fluid. If tester 558 determines that the body fluid is not purified enough, it recycles the impure fluid via line 560 to pump 562 and thence via line 564 back into marker/stripper 550. If the tester 558 determines that the body fluid is adequately purified, it is fed via lines 450/452 back into the organism (see FIG. 15).

Referring again to FIG. 21, and in the preferred embodiment depicted therein, a hermetic enclosure 563 is disposed around flow cytometer sub-assembly 444 (see FIG. 13) to isolate the flow cytometer sub-assembly from any living organism in which it might be implanted.

Figure 22:
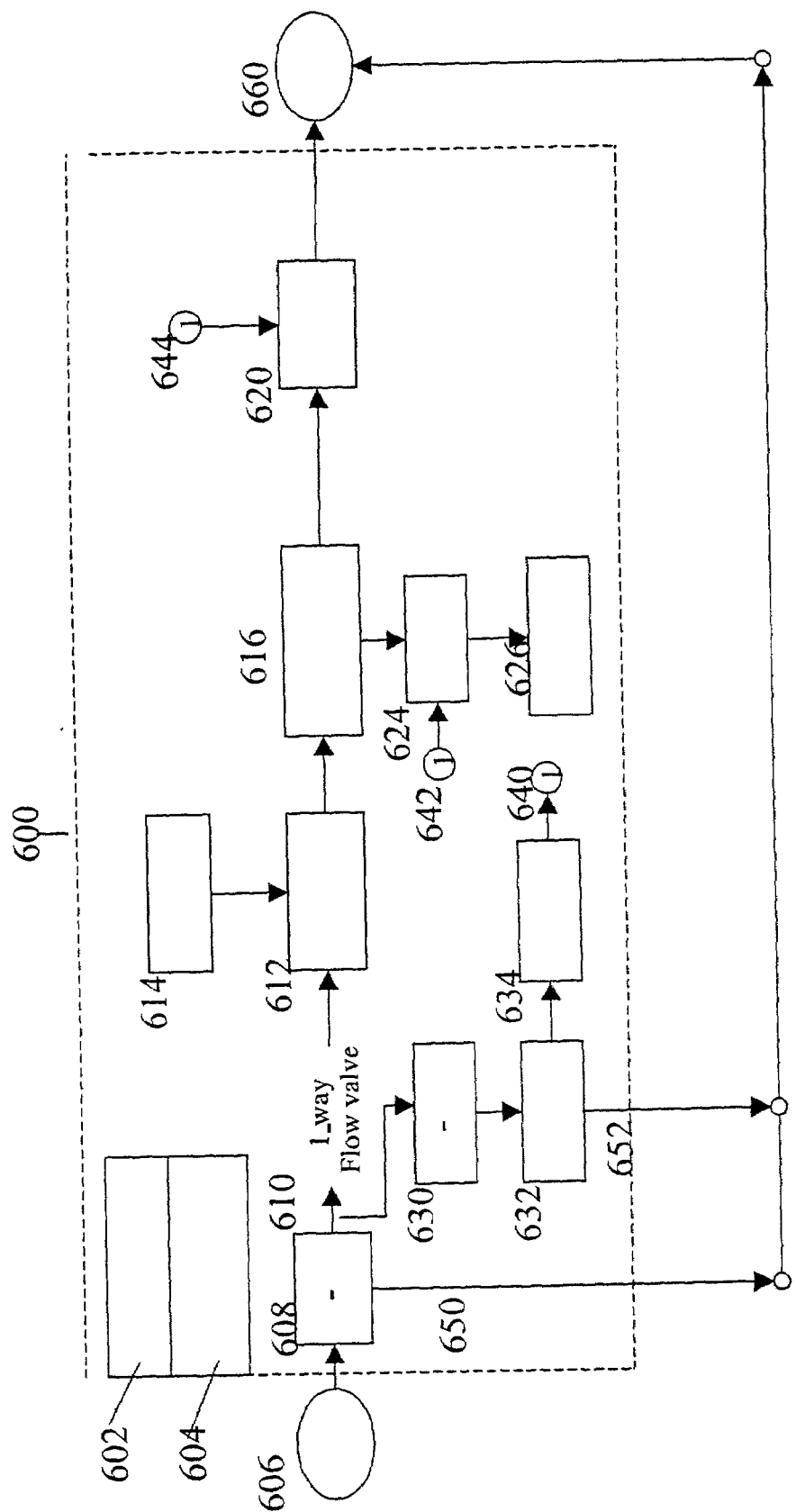
FIG. 22 is a block diagram of yet another preferred sub-process of the invention.

FIG. 22 is a flow diagram of another preferred process of the invention. Referring to FIG. 22, and in the preferred embodiment depicted therein, in step 606 a blood stream is being diverted into a flow cytometer sub-assembly 600. Flow cytometer sub-assembly 600 is comprised of a controller/processor 602 which preferably comprises a built-in programmable logic unit (PLU) and read only memory (RAM)/read and write memory (ROM) library interface. The flow cytometer sub-assembly 600 also comprises communications means 604, which preferably, is telemetry communications means.

In one embodiment, the controller 602 is preferably so constructed as to control all adjustable parameters of all adjustable sub-components of flow cytometer sub-assembly 600. The telemetry communication means 604 is preferably so constructed as to enable the controller/processing unit 602 to receive and analyze (via the programmable logic unit) data information from all the sub-components of the flow cytometer sub-assembly 600 particle analyzer as well as to transmit action adjustment comments to said sub-components based on said analysis of sub-component's sensed or status data. Additionally, communications (telemetry) means 604 may optionally consist of means for communicating with an external programmer, enabling the controller/processor 602's programming of the programmable logic unit (PLU) to be modified. Additionally, the communication telemetry means 604 preferably has the ability to transmit information received from all the sub-components, raw and/or analyzed results performed by the programmable logic unit to an external programmer.

Referring again to FIG. 22, and in step 608 thereof, the bodily fluid stream 606 enters a bypass valve 608 which optionally may allow the bodily fluid stream 606 to continue passing through the cytometer sub-assembly 600 and/or may be set, via the controller 602, to divert the bodily fluid stream 606 via channel 650 around the flow cytometer sub-assembly 600 and back into the primary path of the bodily fluid stream 660.

After passing through the bypass valve 608, the blood stream 606 may enter one-way flow valve 610 and/or one-way flow valve 630. These one way flow valves 610/630 ensure that no fluids nor any chemical additives dissolved in the fluids nor any foreign particles may move upstream of the flow valves 610 and 630, either by diffusion or by any other means.

In step 612 of FIG. 22, the blood stream fluid is mixed with marker(s)/dye(s) from dye reservoir 614. Dye reservoir 614 may consist of several dyes either in individual chambers or mixed together into a single chamber. Alternatively, dye reservoir 614 may consist of a single dye.

The control of the dye(s) injection into the mixing chamber 612 is effected by controller 602. Additionally, the dye reservoir contents may be monitored by said controller 602. If the reservoir 614 is empty of a dye, the patient or external programmer may be notified by communication means 604.

Referring again to FIG. 22, the mixed blood fluid and dye enter the detection and/or sorting sub-component 616 (see FIG. 15 and, in particular, flow chamber 476; also see FIG. 16 and flow chamber 476). If the blood is to be sorted, the sorted fluid is channeled to a dye separator 624 and then stored into sorted reservoir 426 for future extraction and/or other utilization. That portion of the blood fluid and dye marker mix which is not sorted is preferably fed to dye separator 624.

The functionality of the dye separators 620, 624 may require additional plasma fluid which may be obtained from plasma reservoir 634 which is connected to the dye separators 620, 624, through channels 640, 644, 642.

After the dye separator 620 has removed or otherwise rendered the fluid harmless, the fluid is returned to the blood stream 660.

When the blood passes through the by-pass valve 608, it may enter the one-way flow valve 630. Whether the blood flow leaving the by-pass valve 608 enters the one-way flow valve 610 or 630 or both is determined and directed by the controller 602.

On passing through the one-way valve 630, the blood enters a plasma fluid separator 632. Said plasma separator 632 filters and directs a portion of the plasma fluid into plasma reservoir 634 for latter use, as described above. That portion of the fluid which is not diverted to the plasma reservoir 634 is returned to the blood stream 660 through channel 652.

Figure 23:
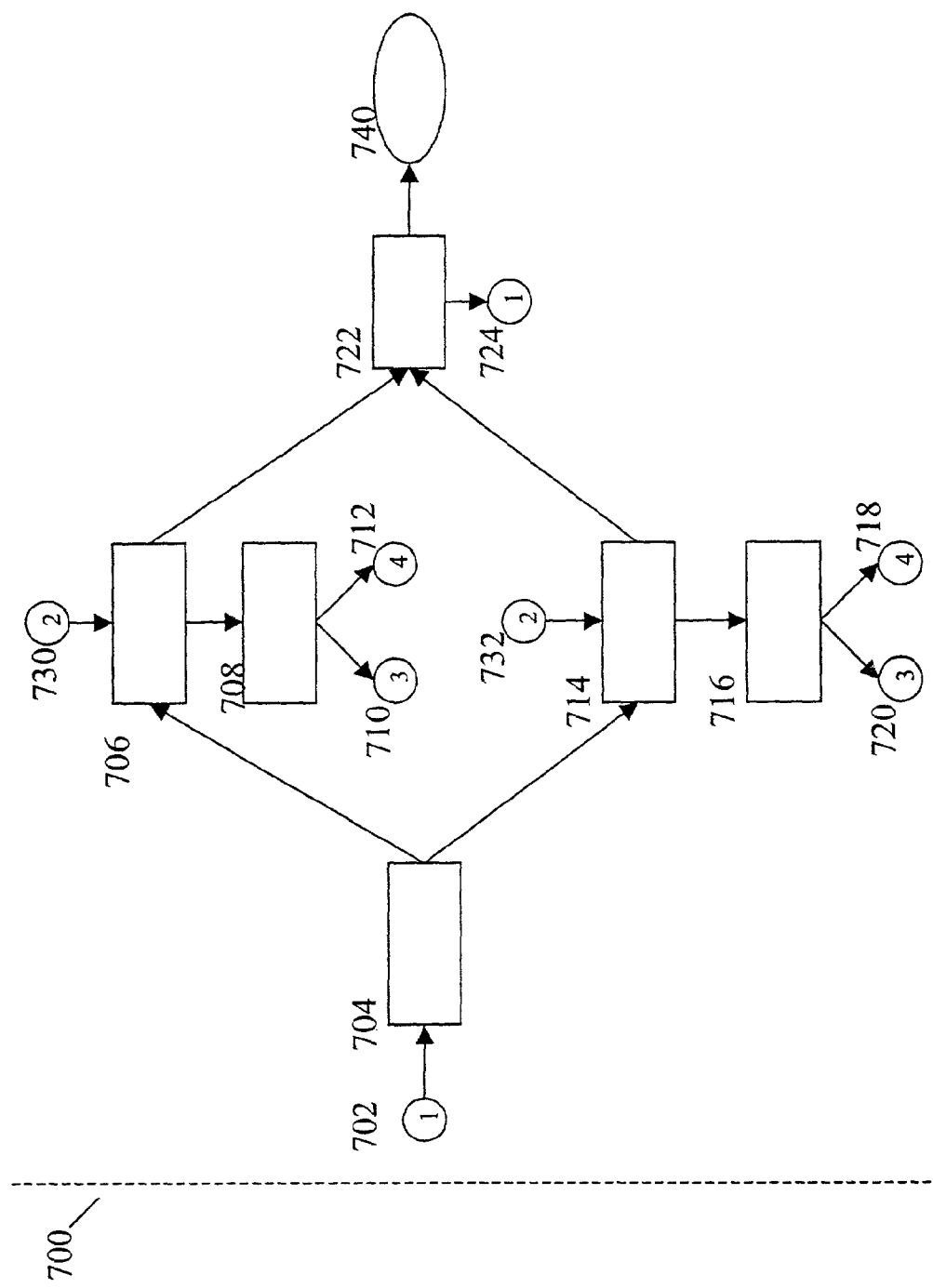
FIG. 23 is a block diagram of one preferred marker remover used in the sub-process of FIG. 22.

FIG. 23 is a block diagram of one preferred dye separation means which may be used in the process of FIG. 22. Referring to FIG. 23, and in the preferred embodiment depicted therein, dye separator 700 is illustrated. A blood/dye mixture enters the dye stripper 700 through connector 702 and passes into a control valve 704. The control valve 704 may direct the blood/dye mix to either dye stripper 706 or dye stripper 714. This allows one of the dye separators 706, 714 to process the fluid while the other dye separator is performing an alternate function, e.g. self diagnostics, and/or cleaning of filters and/or other maintenance functions. The control valve 704 as well as the dye strippers 706, 714 are controlled by the controller 602.

In the preferred embodiment depicted, the blood fluid/dye mix, e.g., is directed to dye stripper 706. The waste material, dye, or other stripped or filtered waste is directed to control valve 708, which may direct the stripped dye via channel 710 back to the dye reservoir 614 of FIG. 22, and/or may direct said material, e.g. to the bladder or other locations via channel 712. The blood fluid, which has been stripped of dye material, is passed from the dye stripper 706 to tester 722, which is used to verify that all the dye has been remove from the blood fluid. If the tester determines that the dye has not been sufficiently removed from the blood fluid, the blood fluid is directed back into the dye separator 700 via connections 724 and 702. Alternatively, if the tester 722 determines that the blood fluid is safe to return to the blood stream, then the blood fluid is passed to the blood stream 740.

The controller 704 may direct the blood/dye mix to enter dye stripper 714 rather than dye stripper 706. The functionality of sub-components 714, 716, 718, 720, 732 are the same as described for sub-components 706, 708, 712, 710, 730 respectively.

The dye strippers 706, 714 of FIG. 23 may be placed into a diagnostic and cleaning mode. In this mode, filters and/or surfaces, not shown, of the dye strippers 706, 714, may be cleansed by a variety of methods including, but not limited to, chemical means, electromagnetic means, heat, mechanical means, cross-fluid flow, back-fluid flow, or other means. Such cleaning methods may require additional fluids. This is provided for by the plasma reservoir 634 of FIG. 22 which is connected to the dye stripper 706, 714 of FIG. 23, via connections 730, 732, respectively, of FIG. 22.

Implantable Cellular Detection and Ablation Device

Figure 24:
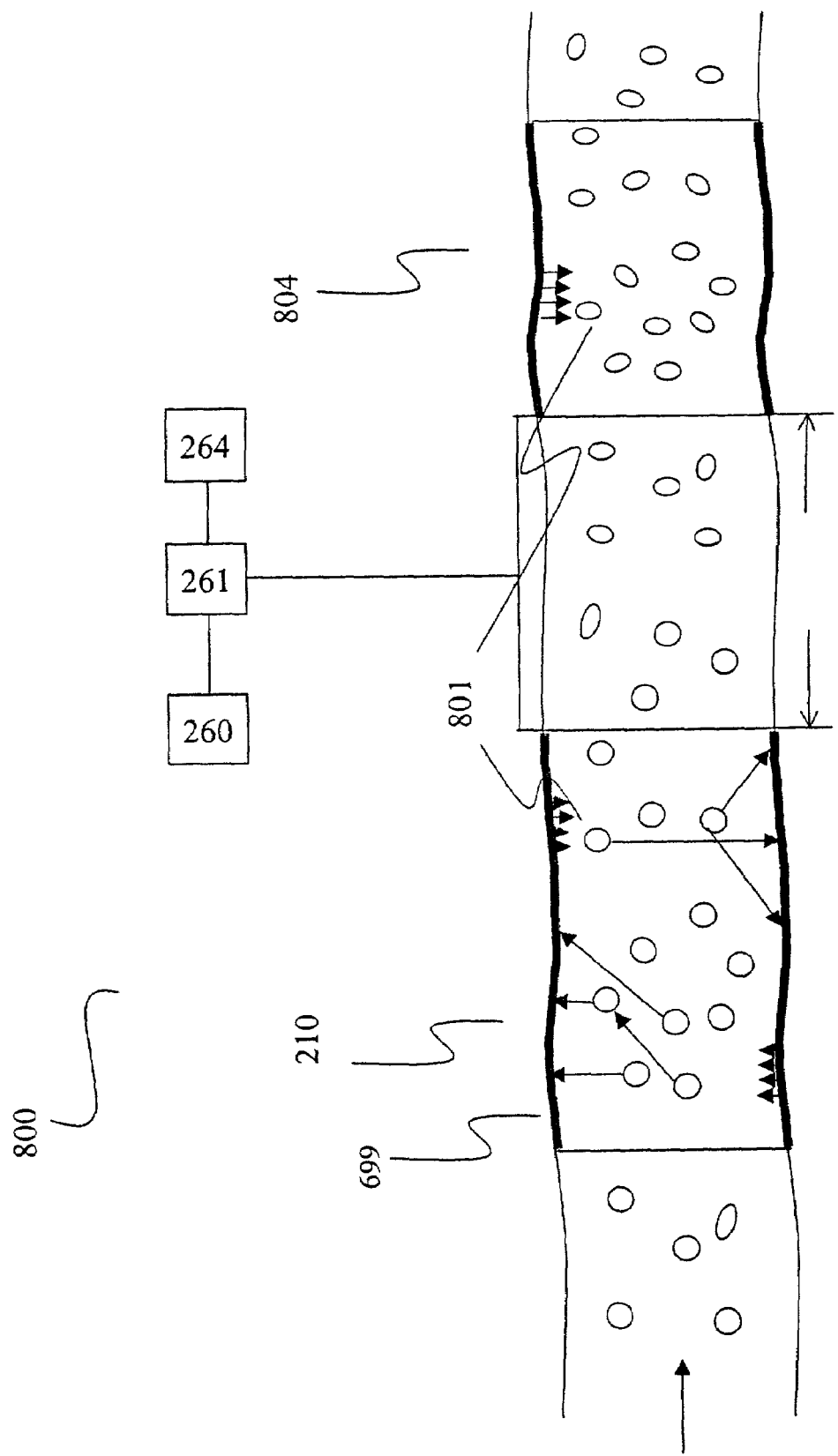
FIG. 24 is a schematic of a separate process of the invention, provided for the treatment of diseased circulating cells.

In a separate embodiment of the invention, illustrated in FIG. 24, an apparatus 800 is provided for the treatment of diseased circulating cell(s) 801. Device 800 is comprised of an additional apparatus that is preferably combined with the stent device 210 described elsewhere in this specification (see FIG. 5).

Referring again to FIG. 24, the device 800, in one embodiment, has the capability of ablating free flowing metastatic cell(s) 801 via a one or more lasers 806 or via photodynamic therapy. As will be apparent, for the sake of simplicity of representation, only one cell 801 is depicted in FIG. 24, only one laser is often referred to, only two optical emitters 230 are shown, and only two detectors 232 are shown. However, in most of the preferred embodiments, a multiplicity of such cells 801. In most of the preferred embodiments, a multiplicity of emitters 230 are used, some of which emit energy that is later sensed in one or more detectors, and others of which emit energy used to ablate one or more of the cells 801.

Referring again to FIG. 24, and in one preferred embodiment, is a preferred separation distance 805 between detection apparatus 210 and the treatment device 804 in order to coordinate the timing between the devices. In another embodiment, not shown, the detection apparatus 210 and the treatment device 804 are part of the same stent configuration and are not separated from each other. In the first such embodiment, the distance 805 preferably is from about 100 microns to 2 millimeters.

Referring again to FIG. 24, the first device 210 is preferably responsible for detection of metastatic or diseased cell(s) 801, and the second device 804 will be responsible for cellular ablation of such cell(s) 801. Detection apparatus 210 is described elsewhere in this specification by reference to FIG. 4. Device 804 will be described later in this specification.

Figure 25:
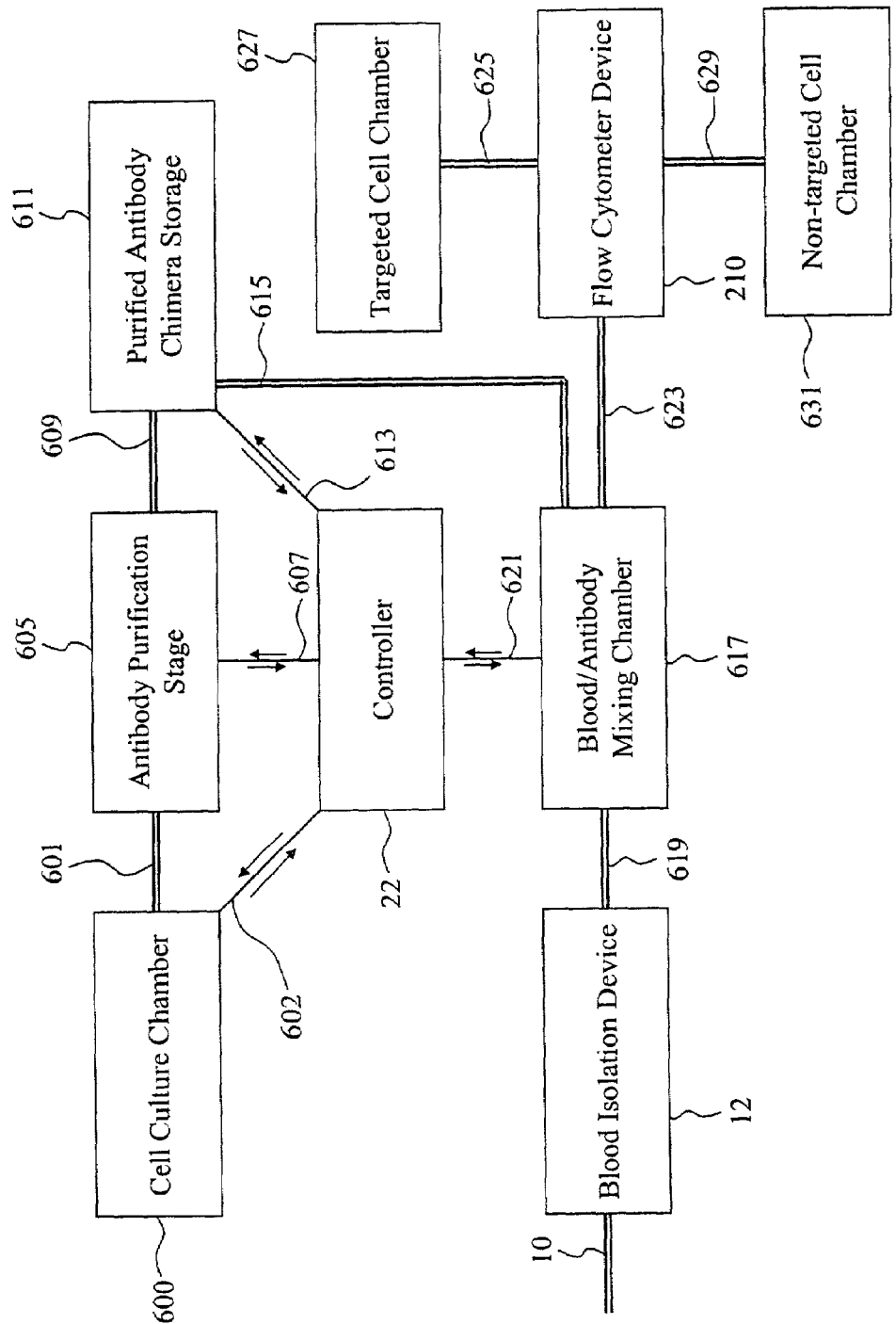
FIG. 25 is a block diagram of preferred process of the invention.

Referring to FIG. 25, and in the embodiment depicted, it is preferred to use fluorescent compound-conjugated antibodies. As is known to those skilled in the art, these antibodies are commonly used for detection of specific components of a fluid in flow cytometry, as they are highly specific for the antigen (the component of interest) against which the antibody has been raised. A chemical reaction is used to covalently bind the fluorophore to the purified antibody, after which the excess unbound fluorophore is washed away. The conditions used for this fluorophore-antibody conjugation usually do not coincide with cellular viability. In addition, the fluorophore used is usually a non-biological compound, which could be toxic to cells and organisms in the concentrated quantities needed for the conjugation reaction. This drawback can be circumvented using a protein fluorophore, such as green fluorescent protein (GFP) or luciferase, which is non-toxic to cells and organisms.

GFP, its color variants, and luciferase are fluorescent proteins which can be used to create fluorescent chimeras of any cloned protein. GFP has been in widespread use as a marker of proteins in living cells and animals for some time, as it appears to have no toxic effects on the cell or organism expressing it. Antibodies have been manipulated to create fluorescent GFP chimeras. Thus the use of GFP antibodies in an implantable system in humans is a preferred method since the antibody is produced with the fluorophore already attached and no additional purification or chemical steps are necessary. The GFP antibodies are produced by the cell lines in cell culture chamber 600. Reference may be had to, e.g., U.S. Pat. No. 5,491,084 ("Uses of green-fluorescent protein"). As is disclosed in this patent, " . . . this invention provides a method for localizing a protein of interest in a cell which comprises: a) introducing into a cell a DNA molecule having DNA sequence encoding the protein of interest linked to DNA sequence encoding a green-fluorescent protein such that the protein produced by the DNA molecule will have the protein of interest fused to the green-fluorescent protein; b) culturing the cell in conditions permitting expression of the fused protein; and c) detecting the location of the green-fluorescent protein in the cell, thereby localizing a protein of interest in a cell." The patent also describes a method wherein " . . . the cells are selected from a group consisting essentially of bacterial cells, yeast cells, fungal cells, insect cells, nematode cells, plant or animal cells. Suitable animal cells include, but are not limited to Vero cells, HeLa cells, Cos cells, CV1 cells and various primary mammalian cells."

In the process of this application, and referring again to FIG. 25, the cell culture (not shown) disposed within cell culture chamber 600 may be maintained in a conventional manner for an extended period of time in a range from about 1 hour to 6 months; this may be done by maintaining the proper balance of nutrients, analytes and growth factors.

It is to be understood that the such cell culture chamber 600 (and the cell culture therein) may also be disposed externally to the body, in which case the antibody production will take place ex vivo. With regard to such cell culture and cell culture chamber 600, reference may be had, e.g., to U.S. Pat. No. 6,315,994 ("Medium and matrix for long-term proliferation of cells") that discloses and claims "A method for increasing insulin production in a transplant, said method comprising: providing pancreatic tissue comprising islet cells and at least about 30% by volume acinar cells; encapsulating the pancreatic tissue in a matrix comprising gelatin and an effective amount of polar amino acids to form a transplant, said polar amino acids selected from the group consisting of arginine, lysine, histidine, glutamic acid, and aspartic acid; and introducing the transplant into a host organism." The entire disclosure of this United States patent is hereby incorporated by reference into this specification.

In another embodiment, the cellular storage within chamber 600 can be performed using the technique described in U.S. Pat. No. 6,008,010 ("Method and apparatus for holding cells"). In this patent there is described an apparatus for holding cells. As is disclosed in this patent the " . . . apparatus comprises a mechanism for incubating cells having a dynamically controlled closed environment in which the cells are grown, which are maintained in a desired condition and in which cells can be examined while the environment is dynamically controlled and maintained in the desired condition. The apparatus also comprises a mechanism for determining the state of the cells. The determining mechanism is in communication with the incubating mechanism. The present invention pertains to a method for holding cells. The method comprises the steps of incubating the cells in a dynamically controlled closed environment, which is maintained in a desired condition and in which the cells can be examined while the environment is dynamically controlled and maintained in the desired condition. Additionally, there is the step of determining the state of the cells." The entire disclosure of this United States patent is hereby incorporated by reference into this specification.

Referring again to FIG. 25, and in one embodiment, the communications line 602 (which may be an optical communications line, and/or a radio frequency communications line) connects the cell culture (not shown) and culture chamber 600 to the controller 22 to maintain the homeostatic environment. The chimeric antibodies (not shown) are passed through fluid conduit 601 to the antibody purification system 605. Communications line 607 (which may be an optical communications line, and/or a radio frequency communications line) connects the antibody purification stage 605 to the controller 22. Fluid conduit 609 connects the antibody purification system 605 to the purified antibody chimera storage device 611. Communications line 613 (which may be an optical communications line, and/or a radio frequency communications line) connects the purified antibody chimera storage device 611 to the controller 22 to maintain homeostatic conditions. Fluid conduit 615 carries the chimera antibodies from the purified antibody chimera storage 611 to the blood/antibody mixing chamber 617. In this chamber the chimera antibodies are mixed and incubated with the blood sample, supplied by line 619 from the blood pool 12, to bind to the specified antigen. Communication line 621 connects the blood/antibody mixing chamber 617 to the controller 22, to monitor the antibody incubation stage.

In the process depicted in FIG. 25, fluid flows may be effected by conventional means. Thus, e.g., one may use any of the implantable pumps and/or fluid delivery devices known to those skilled in the art. Thus, by way of illustration and not limitation, one may use the implantable medical delivery system described in an article by Li Cao et al. entitled "Design and simulation of an implantable medical drug delivery system using microelectromechanical systems technology," (Sensors and Actuators A 94[2001], pages 117–125). Thus, e.g., one may use the microvalves described in an article by Po Ki Yuen et al. entitled "Semi-disposable microvalves for use with microfabricated devices or microchips," (J. Micromech. Microeng. 10 [2000], pages 401–409). Thus, e.g., one may use one or more of the micropumps disclosed in an article by Shulin Zeng et al. entitled "Fabrication and characterization of electoosmotic micropumps" (Sensors and Actuators B 79 [2001], pages 107–114).

In one embodiment, the implantable fluid delivery device of U.S. Pat. No. 6,149,870 ("Apparatus for in situ concentration and/or dilution of materials in microfluidic systems") is used. This patent claims "A microfluidic system for diluting a material in a microfluidic device, the system comprising: a microfluidic device having at least a first main channel disposed therein, said main channel having at least one microscale cross-sectional dimension; at least a first source of said material in fluid communication with said main channel at a first point along a length of said main channel; at least a first diluent source in fluid communication with said main channel at a second point along said length of said main channel; at least a first reservoir in fluid communication with said main channel at a third point along said length of said main channel; and a fluid direction system for delivering diluent and material to said main channel, and combining said diluent with said material to form first diluted material, and for transporting a portion of said first diluted material along said main channel." The entire disclosure of this United States patent is hereby incorporated by reference into this specification.

By way of further illustration, one may use the fluid-delivery device described in U.S. Pat. No. 6,123,861, the entire disclosure of which is hereby incorporated by reference into this specification.

Referring again to FIG. 25, fluid conduit 623 sends the chimera/antigen complex from blood/antibody mixing chamber 617 to the particle analyzer 210, in which one may identify and isolate the antigen (cell) of interest. The chimeric GFP/antibody complexes are often capable of recognizing substantially any protein moieties and, thus, may also be used for the detection of enzymatic activity; alternatively, or additionally, one also may use labeled oligonucleotides for labeling of nucleic acids within a cell or extracellularly. Reference may be had, e.g., to U.S. Pat. No. 6,261,791(" Method for diagnosing cancer using specific PSCA antibodies"). Reference also may be had to U.S. Pat. No. 6,329,179 ("Method enabling use of extracellular RNA extracted from plasma or serum to detect, monitor or evaluate cancer"). This United States patent relates to the use of tumor-derived or associated extracellular ribonucleic acid (RNA) found circulating in the plasma or serum fraction of blood for the detection, monitoring, or evaluation of cancer or premalignant conditions. Extracellular RNA may circulate as non-bound RNA, protein-bound RNA, lipid-RNA complexes, lipoprotein (proteolipid)—RNA complexes, protein-RNA complexes including within or in association with ribonucleoprotein complexes, nucleosomes, or within apoptotic bodies. Any intracellular RNA found in plasma or serum can additionally be detected by this invention. Specifically, this patent enables the extraction of circulating RNA from plasma or serum and utilizes nucleic acid amplification assays for the identification, detection, inference, monitoring, or evaluation of any neoplasm, benign, premalignant, or malignant, in humans or other animals, which might be associated with that RNA. Further, this process of this patent allows the qualitative or quantitative detection of tumor-derived or associated extracellular RNA circulating in the plasma or serum of humans or animals with or without any prior knowledge of the presence of cancer or premalignant tissue; and it may be used in the process of the instant invention.

By way of further illustration, one may also use the process disclosed in U.S. Pat. No. 6,235,486 ("Method for detection of breast cancer"), in which breast cancer is detected by determining the presence of hK2 polypeptide or hK2 RNA in a physiological sample.

By way of yet further illustration, one may use the process disclosed in U.S. Pat. No. 6,355,444 ("Carcinoma associated antigen (SK1) monoclonal antibodies against SK1, methods of producing these antibodies and uses therefore"). This patent discusses carcinoma associated antigen (SK1) and monoclonal antibodies and methods for detecting and ameliorating malignant disease. The monoclonal antibodies discussed in this patent are specifically reactive with epitopes present on SK1.

The entire disclosure of each of these United States patents is hereby incorporated by reference into this specification.

It will apparent that the aforementioned antibodies and nucleic acids, as well as many others not specifically described, may readily be used in one or more of the steps depicted in FIG. 25. Other suitable uses for these reagents and analytes will be apparent to those skilled in the art.

The cells that are labeled by one or more of the steps depicted in FIG. 25 may then be detected and ablated by the device 800 depicted in FIG. 24.

Referring again to FIG. 24, and in one aspect of the embodiment depicted therein, the spatial location of one or more of the labeled cells 801 is estimated using a three-dimensional multivariate non-linear analysis specifying the location and trajectory of the identified cell(s) that preferably is coded into a microprocessor design such as, e.g., microprocessor 264 of the particle analyzer 210 (see FIG. 10).

As is known to those skilled in the art, flowing bodily fluid is generally a non-newtonian fluid when in situ; the flow stream is not linear. The flow characteristics of the bodily fluid are highly dependent on the radius of the vessel through which the fluid flows. The flow characteristics also are dependent upon, e.g., the diameter 216 of the stent/particle analyzer 210 (see FIG. 4).

One means of making the aforementioned estimation is illustrated in FIGS. 26 through 33. As is illustrated in these Figures, there is depicted a three-dimensional schematic view of the placement of one or more cells and/or a stent/particle analyzer within a spherical coordinate system 807. Such spherical coordinate system 807 can be disposed within the lumen of one or more vessels carrying bodily fluid; and it may be disposed in vivo or ex vivo.

Figure 26:
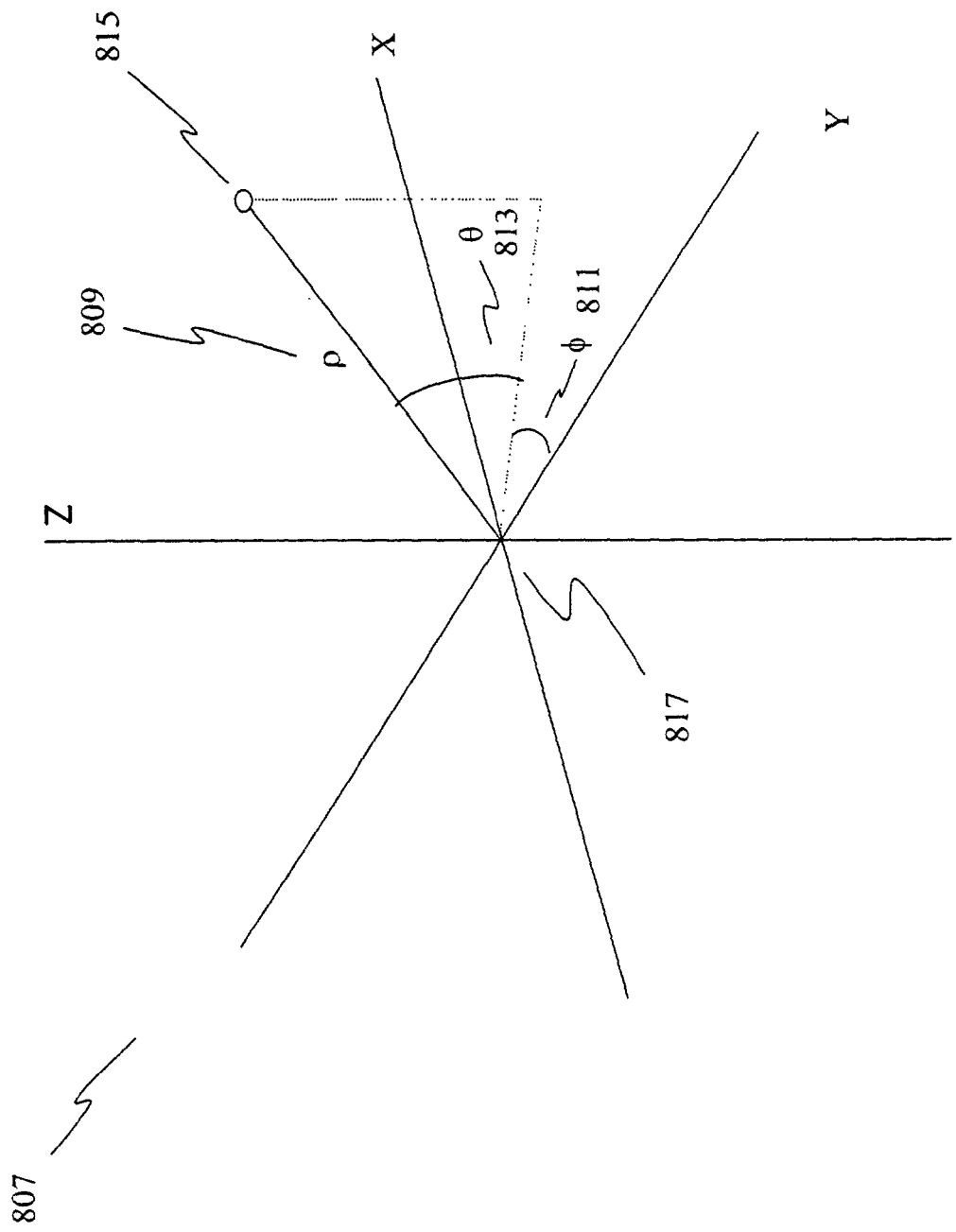

Referring again to FIGS. 26 to 33, and in the preferred embodiment depicted therein, a spherical coordinate system 807 is established with the length vector $\rho$ 809 (units of microns) and angles $\theta$ 811 (units of radians) and $\phi$ 813 (units of radians). The coordinate system is shown in FIG. 26 with reference to a cell 815 and not the stent device. The origin of this coordinate system 807 is located at point 817. The location and the angles relative to scattered emissions from the cell, of the sensor/emitter unit 224 (see FIG. 4) is also located at the origin at point 817. It is to be understood that the coordinate system 807 displayed is a simplified representation to describe the pertinent parameters for spatial location estimation of a labeled cell. It is not limited to a single cell or a single coordinate system.

The combination and analyses of cell sets of data from different coordinate systems will be computationally expensive. Development of microprocessor algorithms for three dimensional object recognition and velocity estimations have been utilized in other fields other than flow cytometry or biological particle flow analysis. In guided missile and satellite detection systems, interpretation of pertinent target information is required for detection. The coordinate system of the target is not only required but also of the transmit/receive component of the detection system; this becomes computationally expensive. Data matching algorithms and cross-correlation analysis for related data sets have been created in a number of fields. In particular, reference may be had to the use of such algorithms in the field of defense radar systems; see, e.g., U.S. Pat. No. 6,239,740 ("Efficient data association with multivariate Gaussian distributed states"), the entire disclosure of which is hereby incorporated by reference into this specification. In this patent " . . . a method is claimed which correlates a plurality of objects comprising scanning said plurality of objects; producing at a first time a set of multi-dimensional data vectors, each of whose members corresponds to a corresponding one of said plurality of objects, each element of each of said members a corresponding to a physical property of said corresponding one of said plurality of objects at said first time; producing at a second time a second set of multi-dimensional data vectors, each of whose members corresponds to one of said plurality of objects, each element of each of said members corresponding to a physical property of said corresponding one of said plurality of objects at said second time; wherein the uncertainty if each element if each said data vector is Gaussian and thus has respective covariance matrices; determining which vector pairs satisfy the gating criterion."

Figure 31:
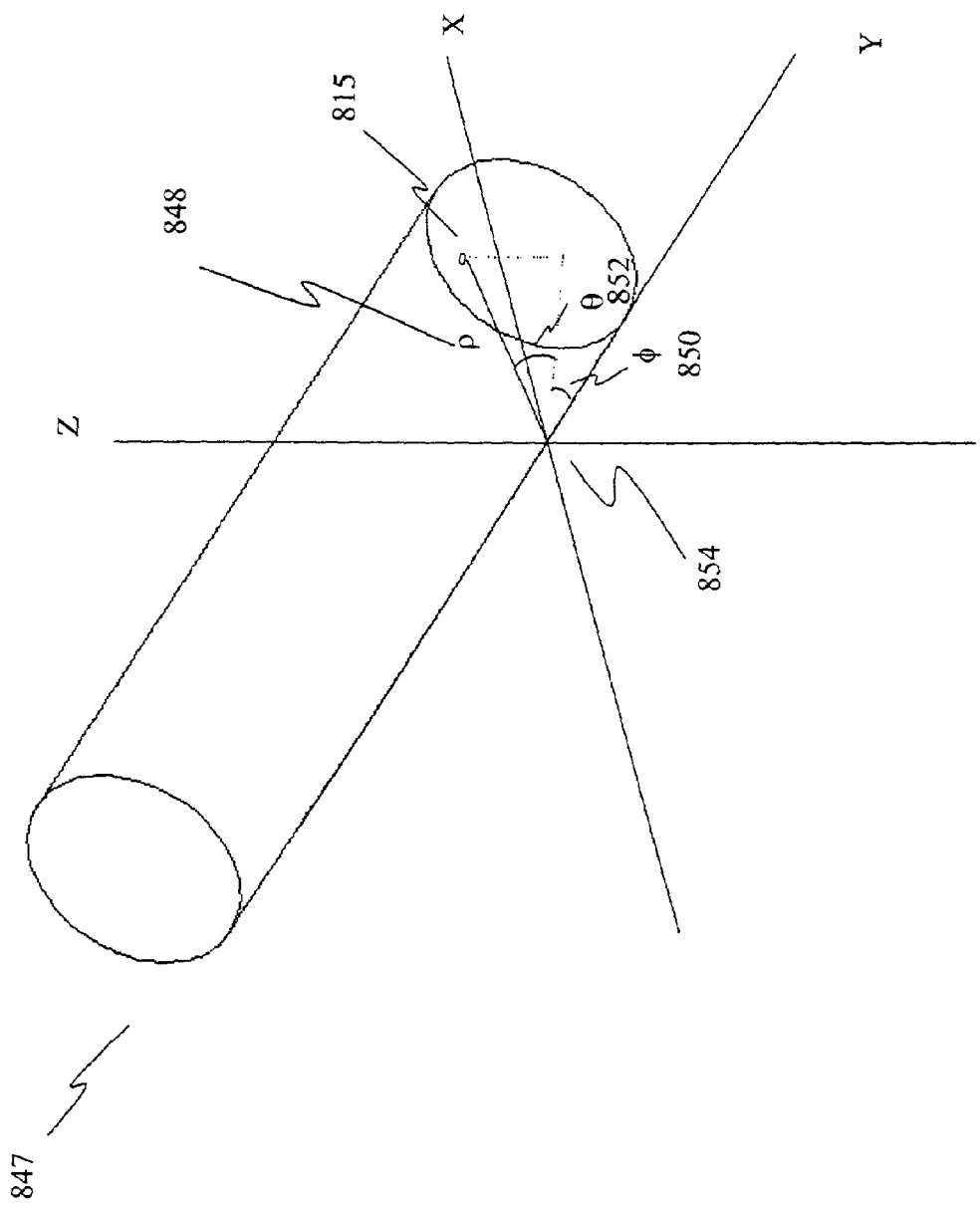

As will be apparent, and referring to FIGS. 27 through 32, the application of these types of detection algorithms may be utilized in the detection of an in vivo labeled cell 815. The coordinate systems in FIGS. 27 through 31 can each be described and are then depicted as different parameters on the same coordinate system. These different parameter sets are identified as parameter sets 811(FIG. 27), 821 (FIG. 28), 831 (FIG. 29), 839 (FIG. 30), and 847 (FIG. 31).

Figure 27:
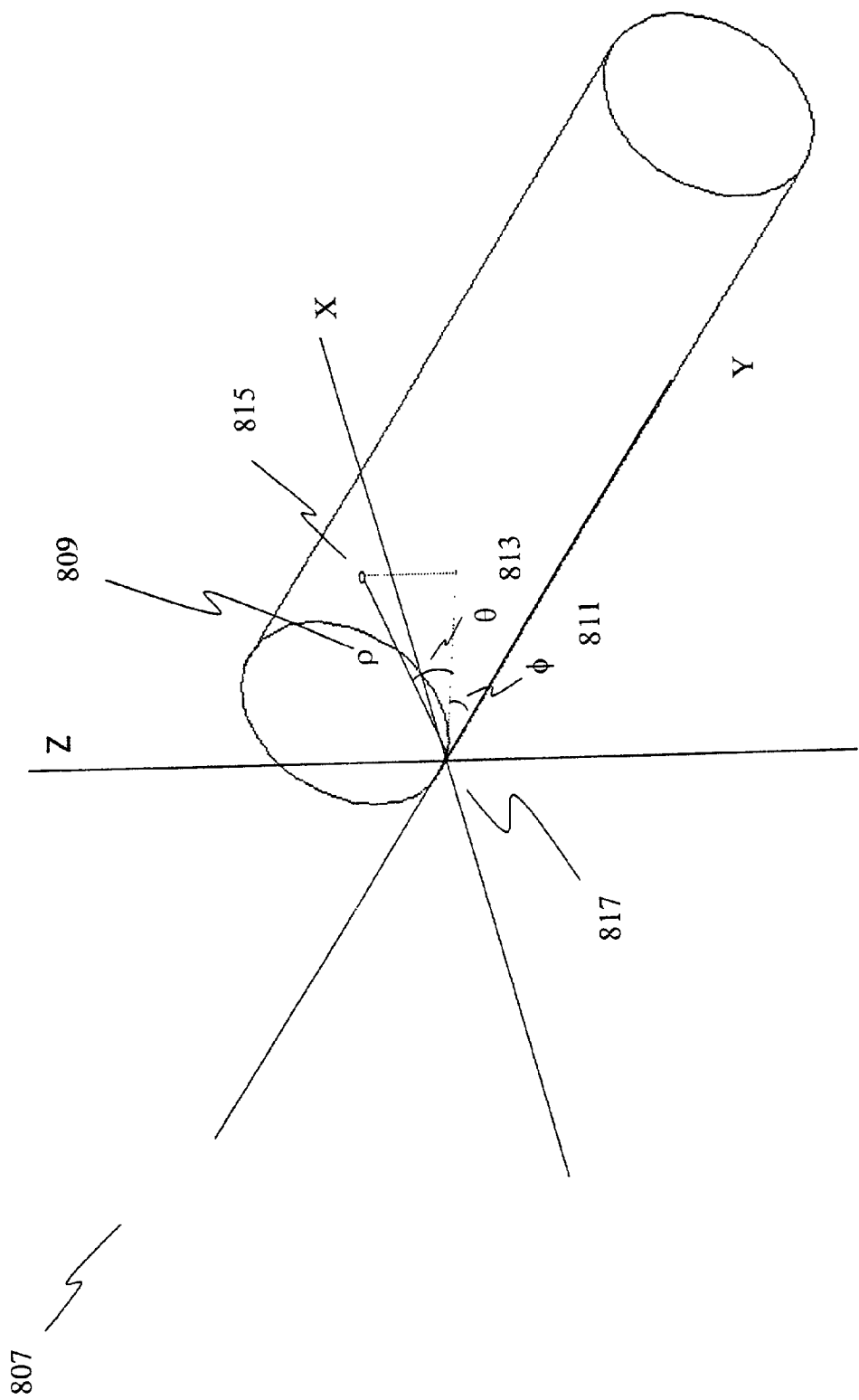
Figure 28:
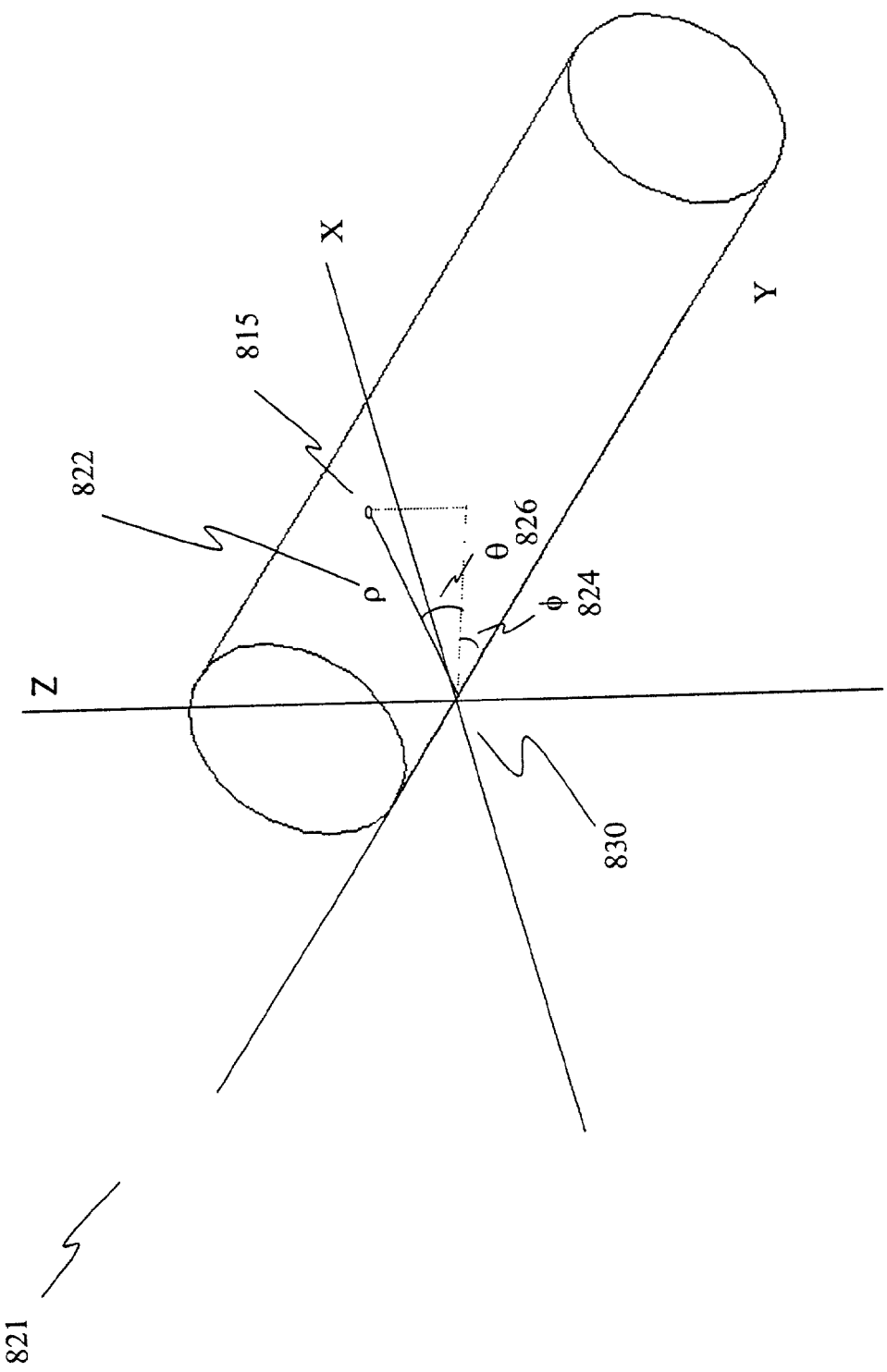
Figure 29:
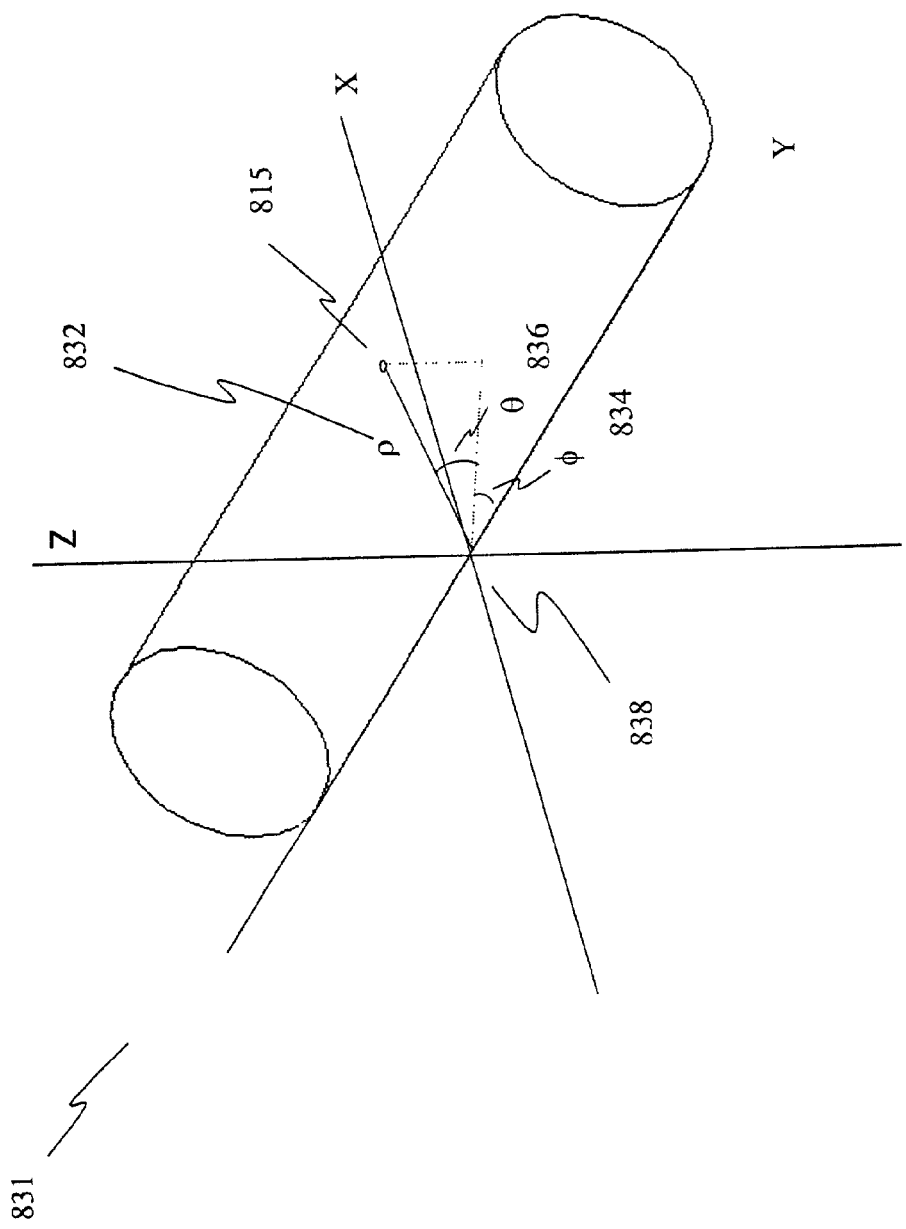
Figure 30:
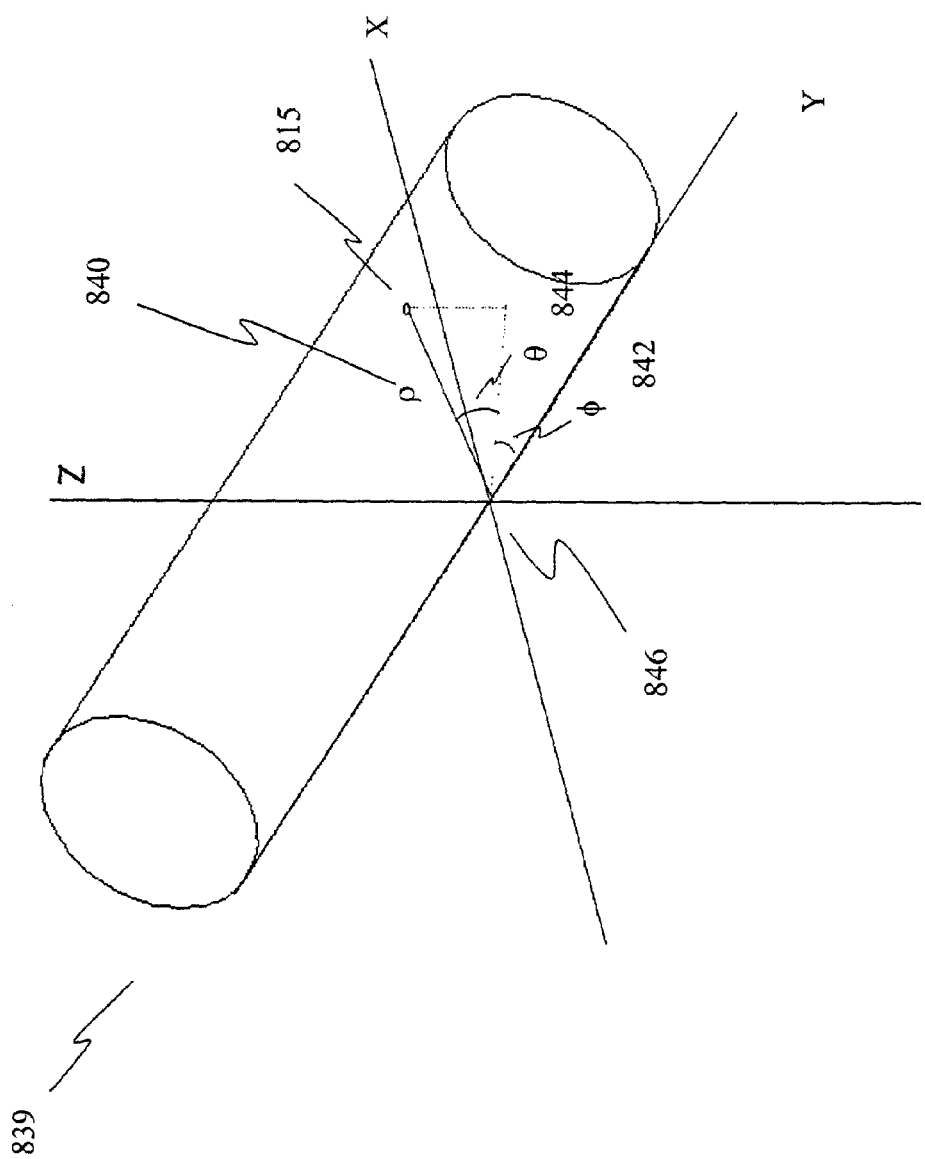
Figure 32:
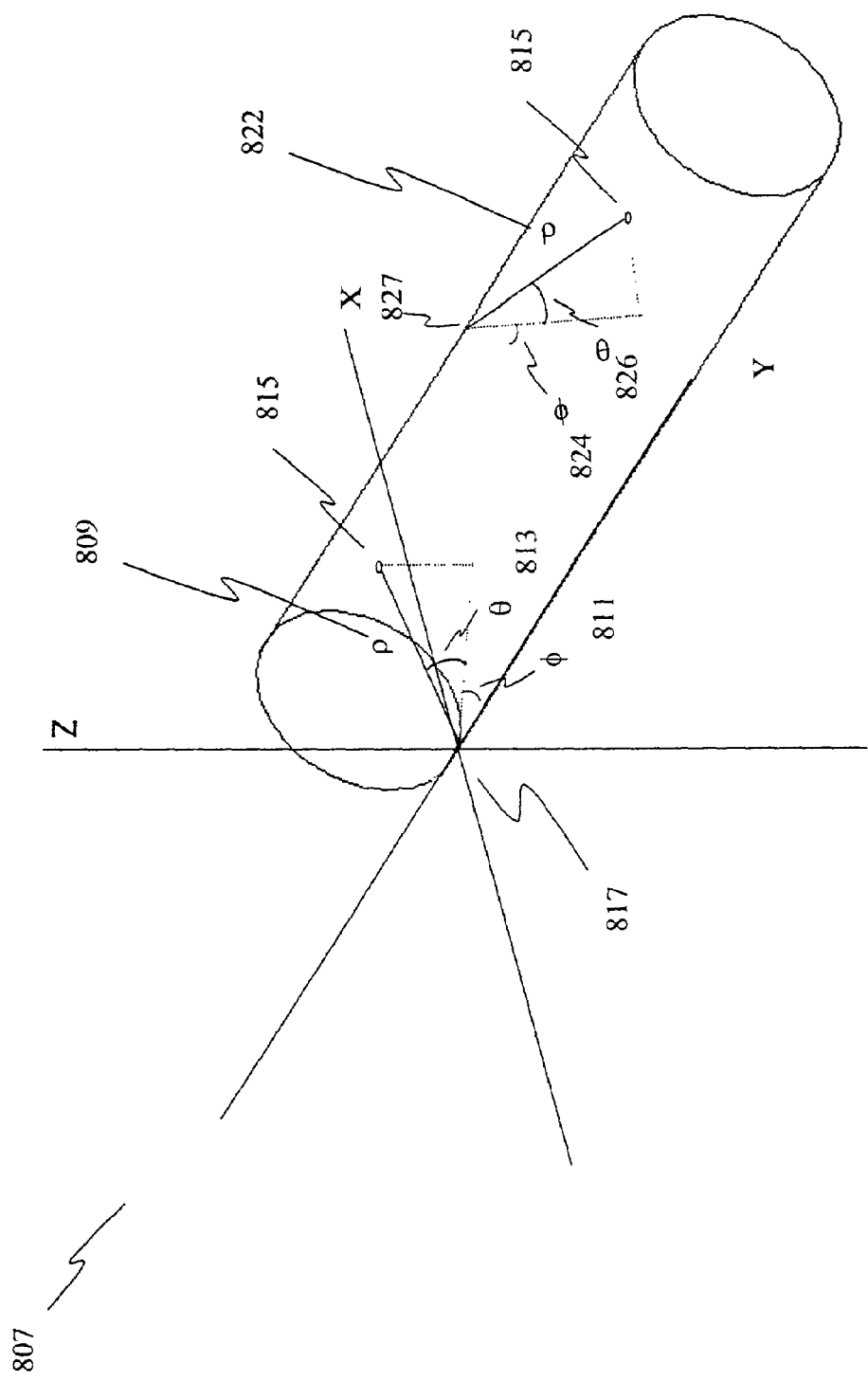
Figure 32A:
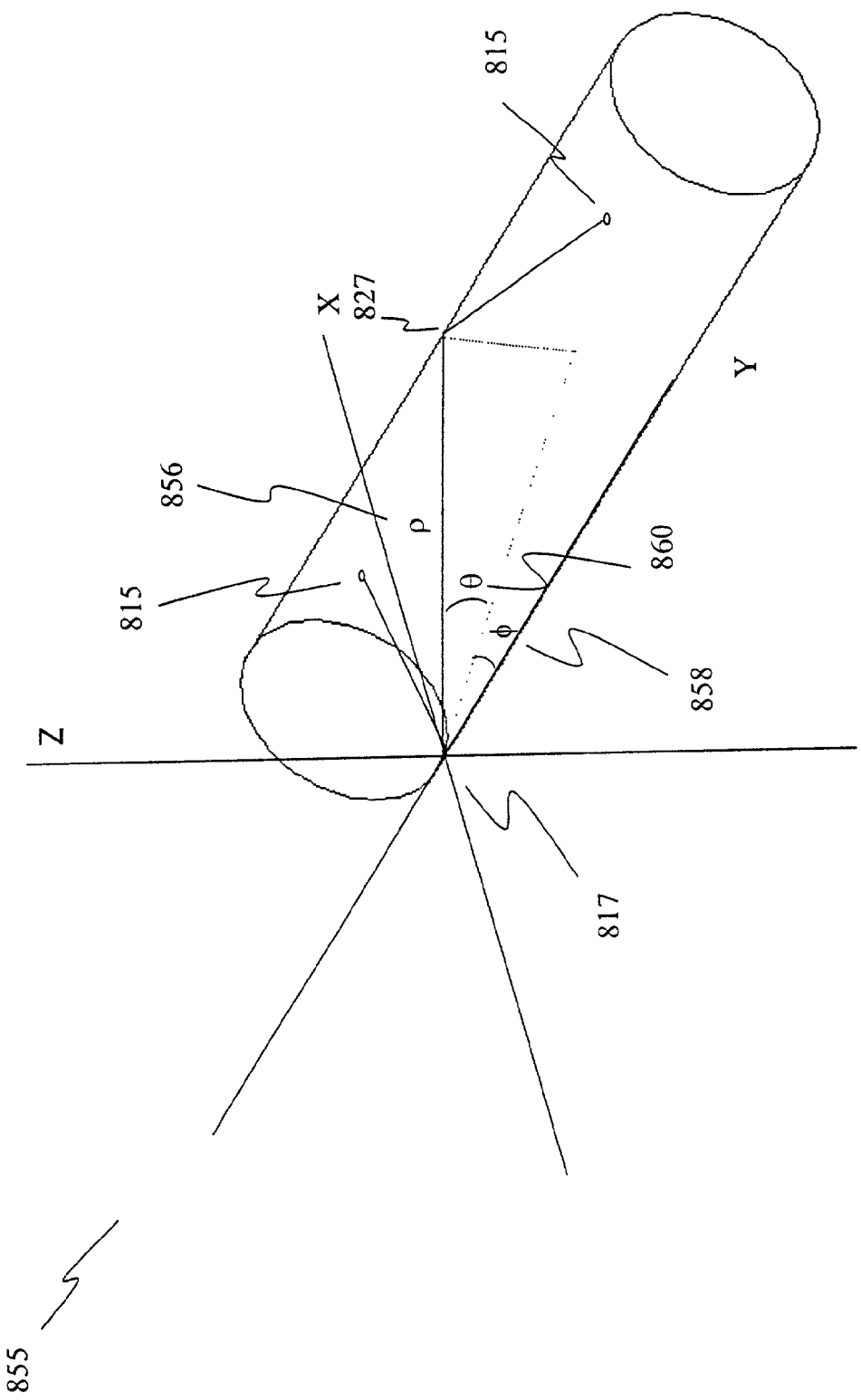

FIG. 32 is a depiction of one possible combination of parameter set 811 and parameter set 821 within a single coordinate system 807; these are also shown in FIGS. 27 and 28, respectively. It is seen that the location of the origins 817 and 827 are on opposing faces of the particle analyzer device. For reinforcement, the origins 807 and 817 are the spatial locations of two separate photodetector/emitter elements 224 (see FIG. 4). The relative location of the elements located at points 817 and 827 with respect to one another may be programmed into the code of the microprocessor. The three dimensional spatial location of all such elements located in the stent device relative to one another is embedded in the microprocessor code. Due to the flexibility of the implantable stent, variations in the initial cylindrical form of the device may take place. Thus, in one embodiment, mechanical stress/strain sensors 699 (see FIG. 24) are placed on the inner surface of the device so that they do not interfere with other functional capabilities of the device. These sensors allow for displacement and deformation estimations of the shape of the stent; the stress/strain relationships sensed enable the estimations of displacement deformation.

One preferred process for utilizing the data from the emitter/detectors 224 (see FIG. 4), and/or the sensors 699, is depicted in FIG. 34.

Referring to FIG. 34, and in step 900, a labeled cell 801 (see FIG. 24) is released from the source of the label (see element 627 in FIG. 25) and/or injected into the individual; the labeled cell enters the stent 210 (see FIG. 24).

In step 902, electromagnetic energy is emitted from emitters 230 of, e.g., stent 210 (see FIG. 5). In one embodiment, the energy is emitted for specified time period(s) only when analyses are desired. In this embodiment, the use of such discontinuous analysis or analyses increases and extends the longevity of the implantable power source(s) required for proper device function.

Any paradigm of pulses and/or time period(s) for pulsing of the emitters 230 may be used as long as it results in an efficient spatial and velocity estimation of the labeled cell(s).

In step 904, which may occur simultaneously with step 902 or thereafter, in one embodiment the labeled cell 801 (see FIG. 24) enters the lumen of the stent 210, whereby electromagnetic energy of a specified wavelength and amplitude is absorbed, scattered, transmitted and/or reflected. The electromagnetic energy so absorbed, scattered, transmitted and/or reflected may be the same energy amplitude and/or wavelength as that emitted by emitters 230; reference may be had, e.g., to FIG. 24. Alternatively, or additionally, the electromagnetic energy so absorbed, scattered, transmitted and/or reflected may have a different amplitude and/or wavelength than the energy emitted; this is one of the preferred embodiments.

As will be apparent, combinations of energies may be emitted and/or absorbed, transmitted and/or scattered and/or reflected, depending upon the circumstances.

For the purposes of illustration and discussion, and for simplicity of representation, the state analysis described hereinafter (see 34) is reduced to represent detection parameters from two photodetector/emitter elements 224. Thus, and referring to FIG. 34, it will be seen that one photodetector 232 (see FIG. 5) will detect the energy which is absorbed, scattered, transmitted and/or reflected from a labeled cell 801. This energy detection by such photodetector 232 in step 906 (see FIG. 34) is the first event with which the preferred algorithm is concerned.

In step 908, a second photodetector 232 detects energy, which is absorbed, scattered, transmitted and/or reflected from a second emission impacting the same labeled cell 801 that was also involved in step 906.

The first emission detected occurs at a time $t_0$, (step 906, FIG. 34) and the second emission detected occurs at a time $t_1$ (step 908, FIG. 34). At time $t_0$, there is the initiation of the algorithm where the first photodetector located at position 817 detects a signal from the labeled cell (refer to FIG. 33). This state, S0, is a function of the four variables ($t_0$, $\rho_0$, $\theta_0$, and $\phi_0$) which represent the spherical coordinates of the labeled cell at the specified time. The detection of a signal from the labeled cell by a second photodetector occurs at a second time, $t_1$, defined by a second state, S1. Where S1 is a function of the original state, S0, and seven additional variables, $t_1$, $\rho_1$, $\theta_1$, $\phi_1$, $\rho_c$, $\theta_c$, and $\phi_c$; the variables $\rho_1$, $\theta_1$, and $\phi_1$ are the spherical coordinates of the labeled cell at time t1 and the variables $\rho_c$, $\theta_c$, and $\phi_c$ represent the spherical coordinates defining the relative spatial relationship of the said first photodetector at location 817, and the said second photodetector at location 827 (refer to FIG. 33). The current state of the labeled cell is defined by a variable, c, and the relative spatial position of the first and second photodetector is defined by the variable, r; and the equations of state flow can be represented as the following:

$S0: c(t_0, \rho_0, \theta_0, \phi_0)$ $S1: S0 + c(t_1, \rho_1, \theta_1, \phi_1) + r(\rho_m, \theta_m, \phi_m)$ $S2: S1 + c(t_2, \rho_2, \theta_2, \phi_2) + r(\rho_m, \theta_m, \phi_m)$

...

$Sn: Sn-1 + c(t_n, \rho_n, \theta_n, \phi_n) + r(\rho_m, \theta_m, \phi_m)$ where the final state of the spatial location, Sn, occurs at time $t_n$ and is a function of Sn−1, $t_n$, $\rho_n$, $\theta_n$, $\phi_n$, $\rho_c$, $\theta_c$, and $\phi_c$. The subscript m is the combination of the state Sn and Sn−1 as it is seen in every state. This representation is for an individual set of photodetectors represented by a vector of states with length n+1. A matrix of size, m×n, can then be created representing a multiplicity of photodetectors for each n representing additional signals acquired from additional photodetectors, and their relative position to the photodetector in the initial state, at the same time point.

In a preferred embodiment, an array, of size a, of matrices sized m×n, can be created where each element of the array preferably represents the condition of photodetectors detecting energy of different wavelengths.

The values of relative positions and times between each signal detection are used to calculate the current trajectory and velocity. The final output of the algorithm is an estimate of a future location and time of arrival of the labeled cell 801 which the processor 261 utilizes to signal an ablative laser from the laser ablation section 804 of the device 800 (see FIG. 24).

Referring again to FIG. 25, and in the embodiment depicted therein, the identified cells of interest are shunted to line 625 to targeted cell isolation chamber 627 for storage. The cells that do not contain the antigen of interest are shunted through line 629 to non-targeted cell chamber 631 for holding.

One may kill specified cells by conventional means. Thus, e.g., one may kill circulating cancer cells by photodynamic therapy. The killing of cancerous cells via photodynamic therapy PDT) is well known to those in the art as described in U.S. Pat. No. 6,071,944 ("Method of treatment of pigmented cancer cells utilizing photodynamic therapy") and in U.S. Pat. No. 6,152,951 ("Method of treating cancer") there is described a method of treating cancer comprising injecting a photosensitizer into a part of a body affected with cancer, and providing a cancer therapeutic instrument comprising a source of laser light. Thus, e.g., in one aspect of this embodiment, a photosensitizing agent is injected into bodily fluid (such as, e.g., the bloodstream) and caused to selectively incorporate into circulating cancerous cells; the photosensitizers agent is so selected that it is activated by radiation at a specific wavelength from laser device 804, whereby the activation of such photosensitizing agent results in cellular death of the cancer cells.

In an additional embodiment, the device 804 of this invention is used to treat atherosclerotic plaques; see, e.g., U.S. Pat. No. 6,228,109 ("Methods for treating atherosclerosis and vulnerable plaques"), the entire disclosure of which is hereby incorporated by reference into this specification. This patent describes and claims: "A method using an ablation apparatus for treating tissues or atherosclerosis on a patient having a pre-implanted medical stent, the method including applying RF energy to the tissue lesion site underlying the stent for therapeutic purposes at different energy levels, different post-procedure times, and different modes of energy delivery." When this patented process is used in conjunction with the current invention, the implantable stent 210 (see FIG. 4) has the capability of reversing the laser out put of the emitting devices 230 (see FIGS. 5 and 7) directed at the surface of the vessel wall (see FIG. 5). The emissions from devices 230, in conjunction with the detectors 232, are preferably used for: (1) the analysis of stenosis, plaque formation, and endothelial cell proliferation, and (2) the ablation of the stenosis, plaque formation, and endothelial cells.

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

We claim:

1. A process for identifying cancerous and/or metastatic cells of a living organism, comprising the steps of:
   feeding a fluid stream comprising said cancerous and/or metastatic cells, to a first assembly comprising a reservoir, wherein said reservoir contains markers capable of labeling the cancerous and/or metastatic cells;
   labeling at least a portion of said cells with said markers so as to produce labeled cells;
   feeding said fluid stream comprising said labeled cells to a second assembly comprising a particle analyzer, wherein said particle analyzer comprises a stent, wherein a plurality of optical assemblies capable of emitting and detecting radiation are disposed on the inner surface of said stent; then
   detecting said labeled cancerous and/or metastatic cells with said particle analyzer.

2. The process as recited in claim 1 further comprising the step of estimating the positions of said labeled cells in or downstream from the stent by means of a three-dimensional, multivariate particle velocity and location estimation algorithm.

3. The process as recited in claim 1, wherein said particle analyzer further comprises a flow cytometer.

4. The process as recited in claim 1, further comprising the step of stripping said markers from the labeled cells within the fluid stream after exiting the particle analyzer, so as to produce a purified fluid stream.

5. The process as recited in claim 1, wherein said marker is a non-toxic fluorescent marker.

6. The process as recited in claim 5, wherein said marker is green fluorescent protein.

7. The process as recited in claim 1, wherein said first and second assemblies are implanted within said living organism.

8. A process for identifying and treating cancerous and/or metastatic cells of a living organism, comprising conducting the process of claim 1, and further comprising ablating said labeled cells, which have been detected by the particle analyzer, with an ablation device.

9. The process as recited in claim 8, wherein the ablation device is positioned downstream from the particle analyzer.

10. The process as recited in claim 9, wherein the distance between the particle analyzer and the ablation device is from about 100 microns to 2 millimeters.

11. The process of claim 8, wherein the ablation device is a part of the stent of the particle analyzer.

12. The process as recited in claim 8, wherein the ablation device comprises a plurality of lasers.

* * * * *